United States Patent
Park et al.

(10) Patent No.: US 9,530,971 B1
(45) Date of Patent: Dec. 27, 2016

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicants: DUK SAN NEOLUX CO., LTD., Cheonan-si, Chungcheongnam-do (KR); SAMSUNG DISPLAY CO., LTD., Yongin-si, Gyeonggi-do (KR)

(72) Inventors: Junghwan Park, Hwaseong-si (KR); Sunhee Lee, Hwaseong-si (KR); Soungyun Mun, Cheonan-si (KR); Bumsung Lee, Hwaseong-si (KR); Jungwook Lee, Gunsan-si (KR); Mikyung Kim, Yongin-si (KR); Kwanhee Lee, Yongin-si (KR)

(73) Assignees: DUK SAN NEOLUX CO., LTD., Cheonan-si (KR); SAMSUNG DISPLAY CO., LTD., Yongin-si (KR)

( * ) Notice: Subject to any disclaimer, the term of this patent is extended or adjusted under 35 U.S.C. 154(b) by 0 days.

(21) Appl. No.: 15/138,443

(22) Filed: Apr. 26, 2016

Related U.S. Application Data

(62) Division of application No. 14/851,719, filed on Sep. 11, 2015, now Pat. No. 9,466,803.

(30) Foreign Application Priority Data

Aug. 28, 2015 (KR) .......................... 10-2015-0122007

(51) Int. Cl.
| | |
|---|---|
| *H01L 51/00* | (2006.01) |
| *H01L 51/50* | (2006.01) |
| *C07D 495/04* | (2006.01) |
| *C07D 491/048* | (2006.01) |
| *C09K 11/06* | (2006.01) |
| *C09K 11/02* | (2006.01) |

(52) U.S. Cl.
CPC ....... *H01L 51/0072* (2013.01); *C07D 491/048* (2013.01); *C07D 495/04* (2013.01); *C09K 11/02* (2013.01); *C09K 11/06* (2013.01); *H01L 51/0052* (2013.01); *H01L 51/0071* (2013.01); *H01L 51/0074* (2013.01); *H01L 51/0085* (2013.01); *C09K 2211/1007* (2013.01); *C09K 2211/1011* (2013.01); *C09K 2211/1029* (2013.01); *C09K 2211/1044* (2013.01); *C09K 2211/1092* (2013.01); *C09K 2211/185* (2013.01); *H01L 51/5016* (2013.01)

(58) Field of Classification Search
CPC ... C07D 495/04; C07D 495/048; C09K 11/02; C09K 11/06; C09K 2211/1007; C09K 2211/1044; C09K 2211/1011; C09K 2211/1092; C09K 2211/185; C09K 2211/1029; H01L 51/0072; H01L 51/0085; H01L 51/0071; H01L 51/0052; H01L 51/0074; H01L 51/5016
See application file for complete search history.

(56) References Cited

FOREIGN PATENT DOCUMENTS

WO   WO 2016/028110   *   2/2016   ........... C07D 209/82

* cited by examiner

*Primary Examiner* — Erich A Leeser
(74) *Attorney, Agent, or Firm* — Vorys, Sater, Seymour & Pease LLP; Mih Suhn Koh

(57) ABSTRACT

Disclosed is a compound represented by Formula 1, an organic electric element comprising a first electrode, a second electrode, and an organic material layer between the first electrode and the second electrode, and an electronic device comprising the organic electric element, wherein the organic material layer comprises the compound of Formula 1 to reduce driving voltage and improve luminous efficiency, and life span.

19 Claims, 1 Drawing Sheet

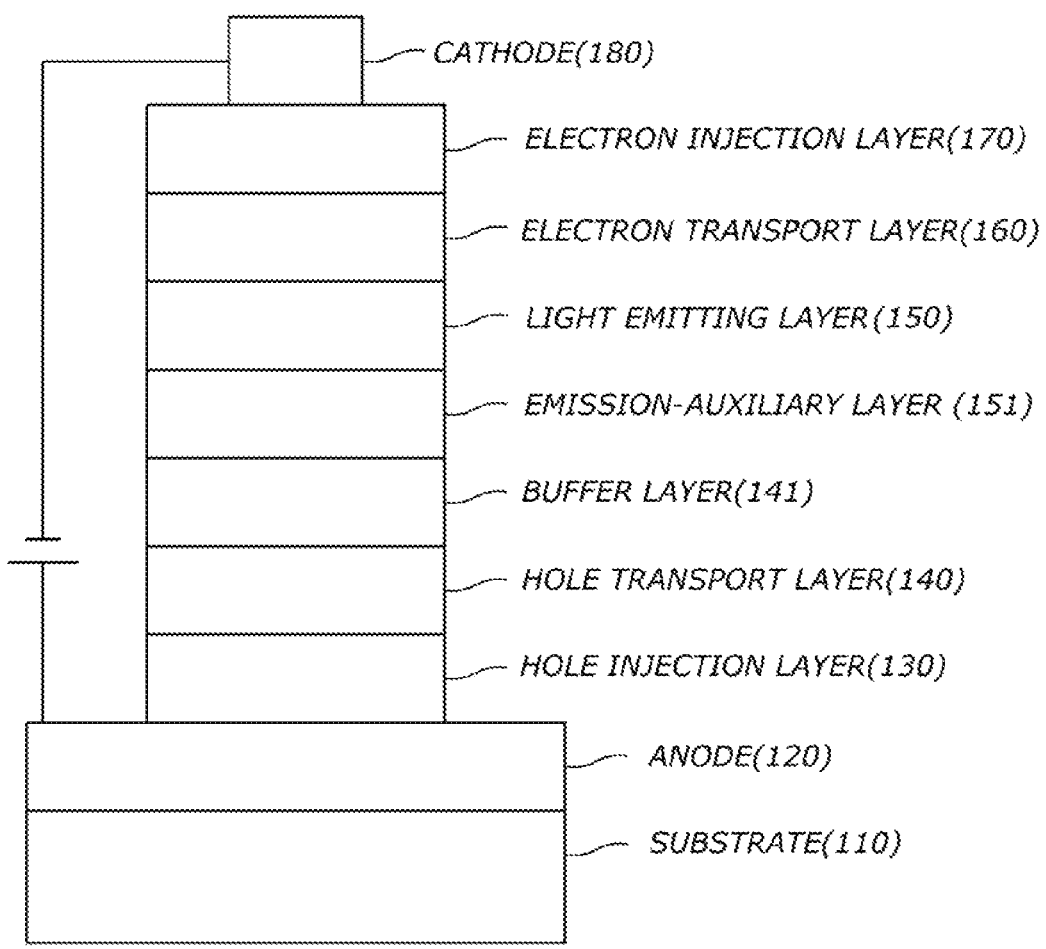

COMPOUND FOR ORGANIC ELECTRIC ELEMENT, ORGANIC ELECTRIC ELEMENT COMPRISING THE SAME AND ELECTRONIC DEVICE THEREOF

BACKGROUND

Technical Field

The present invention relates to compounds for organic electric elements, organic electric elements using the same, and electronic devices thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer may have a multilayered structure including multiple layers made of different materials in order to improve the efficiency and stability of an organic electric element, and for example, may include a hole injection layer, a hole transport layer, a light emitting layer, an electron transport layer, an electron injection layer, or the like.

A material used as an organic material layer in an organic electric element may be classified into a light emitting material and a charge transport material, for example, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from electronic excited singlet states and a phosphorescent material derived from electronic excited triplet states according to its light emitting mechanism. Further, the light emitting material may be divided into blue, green, and red light emitting materials, and yellow and orange light emitting materials required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to a deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, e power consumption is a very important factor the portable display with a limited power source of the battery, and efficiency and life span issue also is solved.

Efficiency, life span, driving voltage, and the like are correlated with each other. For example, if efficiency is increased, then driving voltage is relatively lowered, and the crystallization of an organic material due to Joule heating generated during operation is reduced as driving voltage is lowered, as a result of which life span shows a tendency to increase. However, efficiency cannot be maximized only by simply improving the organic material layer. This is because long life span and high efficiency can be simultaneously achieved when an optimal combination of energy levels and T1 values, inherent material properties (mobility, interfacial properties, etc.), and the like among the respective layers included in the organic material layer is given.

Therefore it is required to develop a light emitting material that has high thermal stability and can achieve efficiently charge balance the light-emitting layer. In order to allow an organic electric element to fully exhibit the above-mentioned excellent features, it should be prerequisite to support a material constituting an organic material layer in the element, for example, a hole injection material, a hole transport material, a light emitting material, an electron transport material, an electron injection material, or the like, by a stable and efficient material.

However, such a stable and efficient organic material layer material for an organic electric element has not yet been fully developed. Particularly, the developments of host materials for a light emitting layer, and the combination between the host materials and appropriate dopant materials, are required highly.

SUMMARY

In order to solve one or more of the above-mentioned problems in prior art, an aspect of the present invention is to provide a compound which allows an organic electric element to have low driving voltage and to be improved in luminous efficiency, color purity, stability, and life span, an organic electric element comprising the same, and an electronic device including the organic electric element.

In accordance with an aspect of the present invention, compounds represented by the following formula are provided:

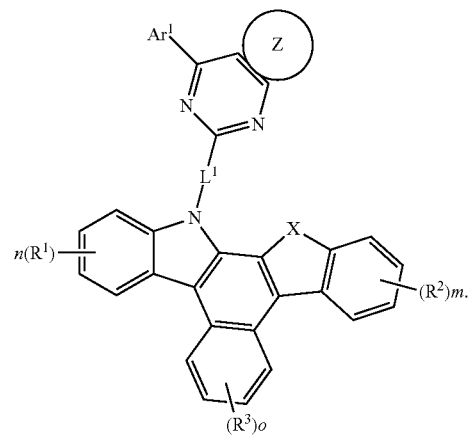

In another aspect of the present invention, organic electric elements comprising the compound represented by the formula above and electronic devices including the organic electric element are provided.

By using the compounds according to the embodiments of the present invention, the organic electric elements according to one or more embodiments of the present invention not only have low driving voltage, but can also be significantly improved in luminous efficiency, color purity, stability, and life span.

BRIEF DESCRIPTION OF THE DRAWINGS

FIG. 1 illustrates an example of an organic light emitting diode according to an embodiment of the present invention.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below. Also, "substituted fluorenyl group" or "substituted fluorenylene group" means, functional group which at least any one of R, R' and R" is a functional group other than hydrogen and spiro compound which R and R' can be linked together with the carbone to which they are attached to form spiro compound.

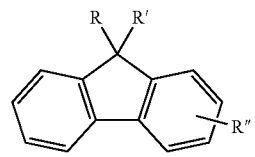

Unless otherwise stated, the term "aryl group" or "arylene group" as used herein has, but not limited to, 6 to carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents at least one of N, O, S, P, and Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes compound below.

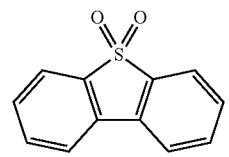 [SMILES: O=S1(=O)c2ccccc2-c2ccccc21]

Univalent or bivalent functional group as used herein is named a functional group name or writing the valence in front of the parent compound. For example, "bivalent benzothiophene" means a divalent functional group of the parent compound benzothiophene, similarly, "bivalent dibenzothiophene" means a divalent functional group of the parent compound dibenzothiophene, "bivalent furan" means a divalent functional group of the parent compound furan, "bivalent dibenzofuran" means a divalent functional group of the parent compound dibenzofura, and "bivalent pyrimidine" means a divalent functional group of the parent compound pyrimidine.

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a fluorenyl group, a $C_8$-$C_{20}$ arylalkenyl group, a silane group, a boron group, a germanium group, and a $C_5$-$C_{20}$ heterocyclic group containing at least one heteroatom selected from the group consisting of O, N, S, Si, and P.

Otherwise specified, the formulas used in the present invention are as defined in the index definition of the substituent of the following formula.

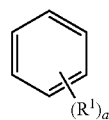

Wherein, when a is an integer of zero, the substituent $R^1$ is absent, when a is an integer of 1, the sole $R^1$ is linked to any one of the carbon atoms constituting the benzene ring, when a is an integer of 2 or 3, the substituent $R^1$s may be the same and different, and are linked to the benzene ring as follows. when a is an integer of 4 to 6, the substituents $R^1$s may be the same and different, and are linked to the benzene ring in a similar manner to that when a is an integer of 2 or 3, hydrogen atoms linked to carbon constituents of the benzene ring being not represented as usual.

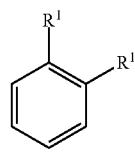
(a=2)

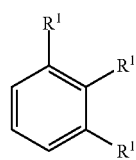
(a=3)

FIG. 1 illustrates an organic electric element according to an embodiment of the present invention.

Referring to FIG. 1, an organic electric element 100 according to an embodiment of the present invention includes a first electrode 120 formed on a substrate 110, a second electrode 180, and an organic material layer between the first electrode 120 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer includes a hole injection layer 130, a hole transport layer 140, a light emitting layer 150, an electron transport layer 160, and an electron injection layer 170 formed in sequence on the first electrode 120. Here, the layers included in the organic material layer, except the light emitting layer 150, may not be formed. The organic material layer may further include a hole blocking layer, an electron blocking layer, an emission-auxiliary layer 151, a buffer layer 141, etc., and the electron transport layer 160 and the like may serve as the hole blocking layer.

Although not shown, the organic electric element according to an embodiment of the present invention may further include a protective layer or a capping layer formed on at least one of the sides the first and second electrodes, which is a side opposite to the organic material layer.

The inventive compound employed in the organic material layer may be used as materials of the hole injection layer 130, the hole transport layer 140, the electron transport layer 160, the electron injection layer 170, a host or a dopant of the light emitting layer 150, or the capping layer. Preferably, the inventive compound may be used as materials of the host or the dopant of the light emitting layer.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon.

Also, the organic material layer may be manufactured in such a manner that a smaller number of layers are formed using various polymer materials by a soluble process or solvent process, for example, spin coating, dip coating, doctor blading, inkjet printing, screen printing, or thermal transfer, instead of deposition. Since the organic material layer according to the present invention may be formed in various ways, the scope of protection of the present invention is not limited by a method of forming the organic material layer.

According to used materials, the organic electric element according to an embodiment of the present invention may be of a top emission type, a bottom emission type, or a dual emission type.

A WOLED (White Organic Light Emitting Device) readily allows for the formation of ultra-high definition images, and is of excellent processability as well as enjoying the advantage of being produced using conventional color filter technologies for LCDs. In this regard, various structures for WOLEDs, used as back light units, have been, in the most part, suggested and patented. Representative among the structures are a parallel side-by-side arrangement of R (Red), G (Green), B (Blue) light-emitting units, a vertical stack arrangement of RGB light-emitting units, and a CCM (color conversion material) structure in which electroluminescence from a blue (B) organic light emitting layer, and photoluminescence from an inorganic luminescent using the electroluminescence are combined. The present invention is applicable to these WOLEDs.

Further, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device, which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, a compound according to an aspect of the present invention will be described.

A compound according to an aspect of the present invention is represented by Formula 1 below.

In formula 1 above, each symbol may be defined as follows.

Z ring may be a $C_{10}$-$C_{20}$ aryl group, preferably, a $C_{10}$-$C_{14}$ aryl group, more preferably, naphthalene or phenanthrene.

X may be O or S.

$L^1$ may be selected from the group consisting of a single bond, a $C_6$-$C_{60}$ arylene group, a fluorenylene group, a $C_2$-$C_{60}$ heteroarylene group containing at least one hetero atom selected from the group consisting of O, N, S, Si, and P, and a fused ring group of a $C_3$-$C_{60}$ aliphatic ring and a $C_6$-$C_{60}$ aromatic ring. $L^1$ may be preferably selected from the group consisting of a single bond, a $C_6$-$C_{12}$ arylene group, a divalent $C_2$-$C_{12}$ heteroarylene group containing at least one hetero atom selected from the group consisting of O, N, S, Si, and P, a fluorenylene group. Also, $L^1$ may be preferably selected a divalent phenyl group, a divalent biphenyl group, a divalent 9,9-dimethyl-9H-fluorene group, a divalent dibenzothiophene.

$Ar^1$ may be selected from the group consisting of a $C_6$-$C_{60}$ aryl group, a $C_2$-$C_{60}$ heterocyclic group containing at least one hetero atom selected from the group consisting of O, N, S, Si, and P, a fluorenyl group, and a fused ring group of a $C_3$-$C_{60}$ aliphatic ring and a $C_6$-$C_{60}$ aromatic ring. $Ar^1$ may be preferably selected from the group consisting of a $C_6$-$C_{12}$ aryl group, a $C_5$-$C_{16}$ heterocyclic group containing at least one hetero atom selected from a group consisting of O, N, and S, and fluorenyl group, and more preferably a phenyl group, a naphthyl group, biphenyl group, 9-phenyl-9H-carbazolyl group, 9,9-dimethyl-9H-fluorenyl group, pyridyl group, dibenzothienyl group, dibenzofuryl group,

[Formula 1]

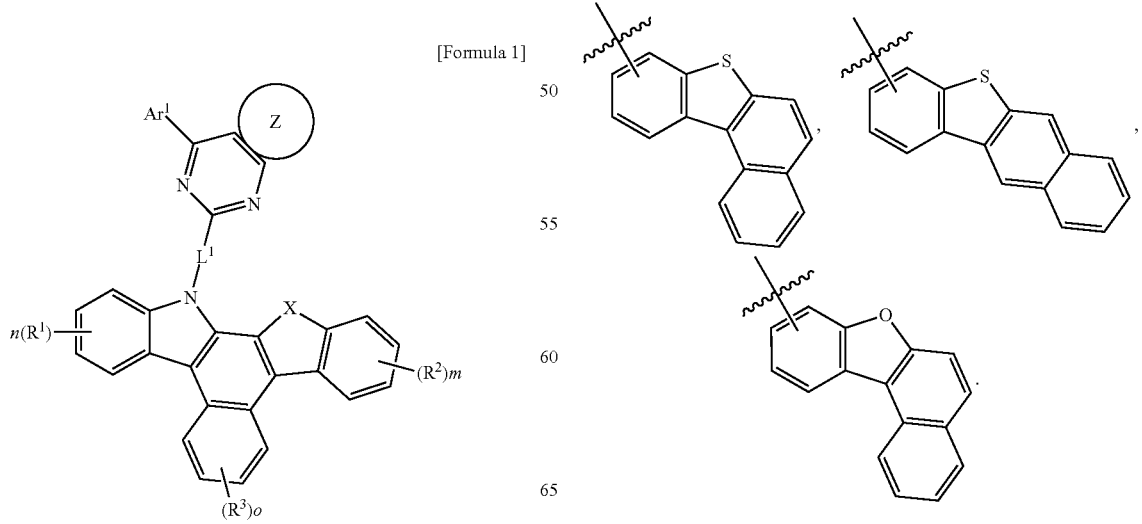

Each of m, n and o may be an integer of 0 to 4, and each all can preferably be an integer 0.

$R^1$, $R^2$ and $R^3$ may be independently selected from the group consisting of deuterium, halogen, a $C_6$-$C_{60}$ aryl group, a fluorenyl group, a $C_2$-$C_{60}$ heterocyclic group containing at least one hetero atom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxy group, a $C_6$-$C_{30}$ aryloxy group, and -L'-N($R_a$) ($R_b$). When each of m, n and o may be an integer of 2 or more, each of plural $R^1$s, $R^e$s and $R^a$s may be the same or different, also, can be independently linked together to form at least one fused ring.

L' may be selected from the group consisting of a single bond, a $C_6$-$C_{60}$ arylene group, a fluorenylene group, a fused ring group of a $C_3$-$C_{60}$ aliphatic ring and a $C_6$-$C_{60}$ aromatic ring, and a $C_2$-$C_{60}$ heterocyclic group $R_a$ and $R_b$ may be independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from the group consisting of O, N, S, Si, and P.

The aryl group, heterocyclic group, fluorenyl group, fused ring group, alkyl group, alkenyl group, alkynyl group, alkoxy group, aryloxy group, arylene group, and fluorenylene group may be optionally substituted by one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted by deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

The compound represented by Formula 1 above may be represented by any one of the following formulas.

[Formula 2]

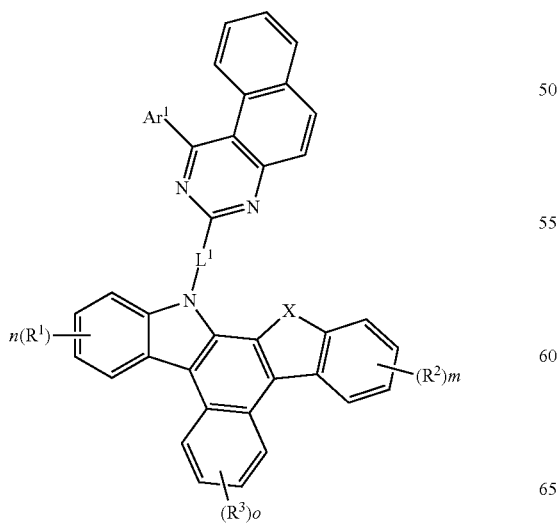

[Formula 3]

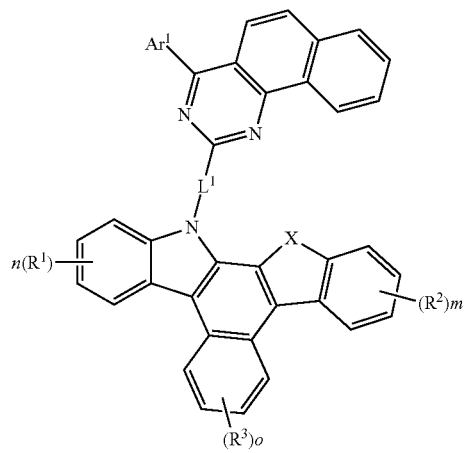

[Formula 4]

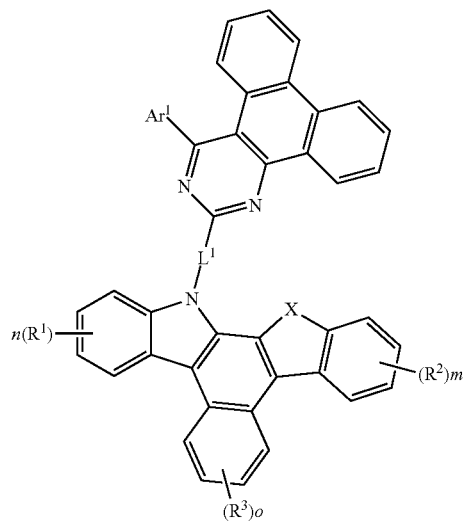

In Formula 2 to 4, $Ar^1$, $L^1$, $R^1$ to $R^3$, m, n, o and X may be as defined in Formula 1.

Specifically, the compound represented by Formula 1 above may be represented by one of the compounds below.

1-1

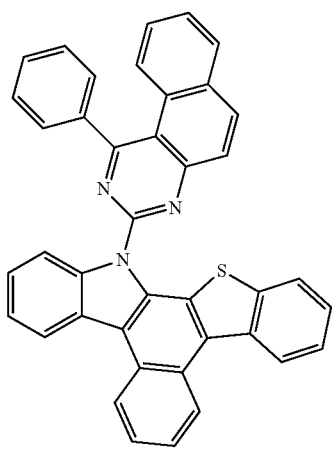

-continued
1-2
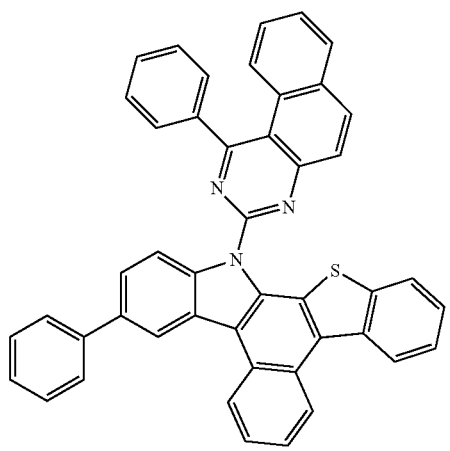
1-3
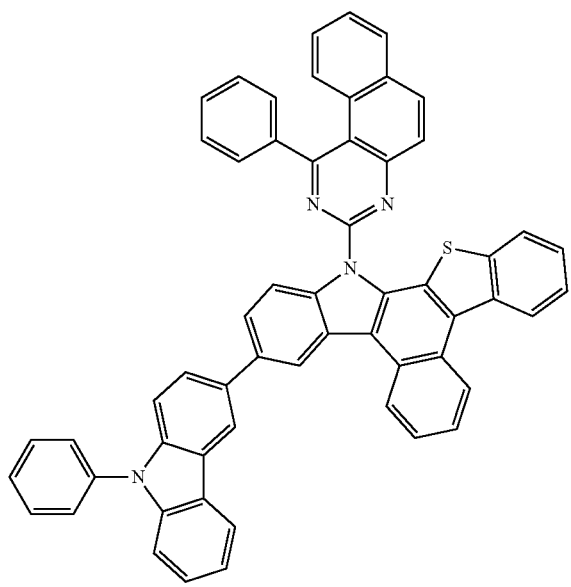
1-4
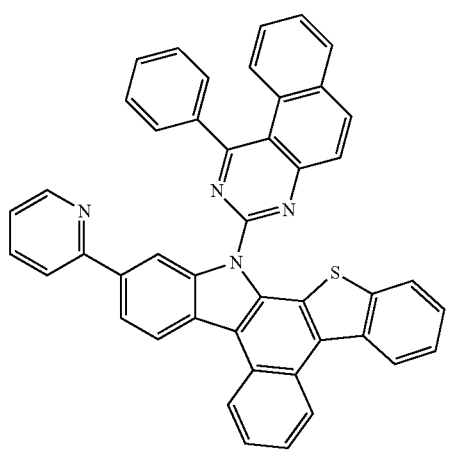
-continued
1-5
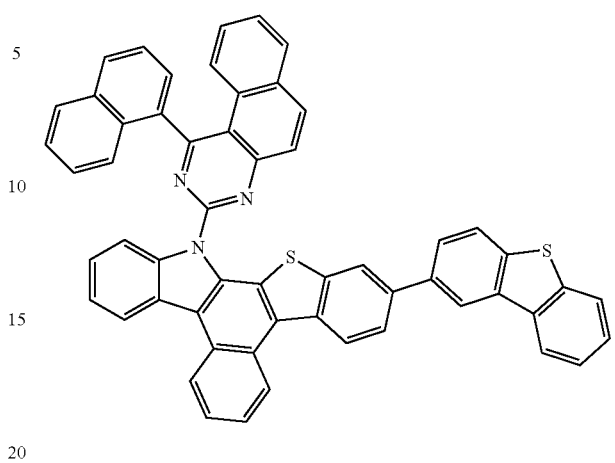
1-6
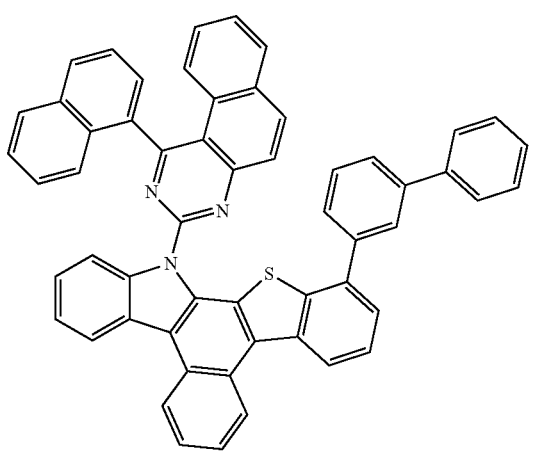
1-7
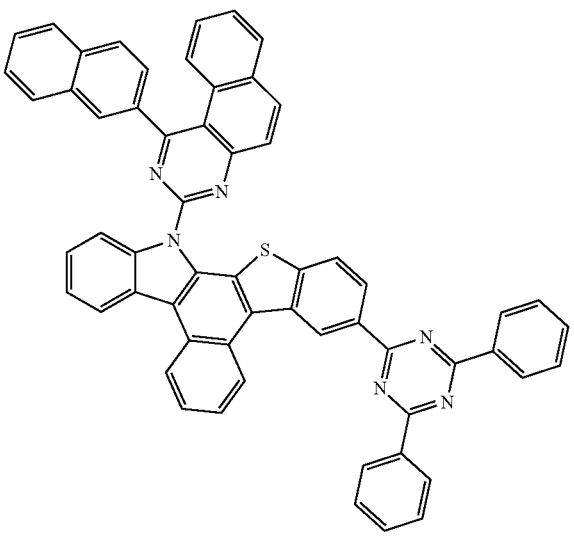

1-8
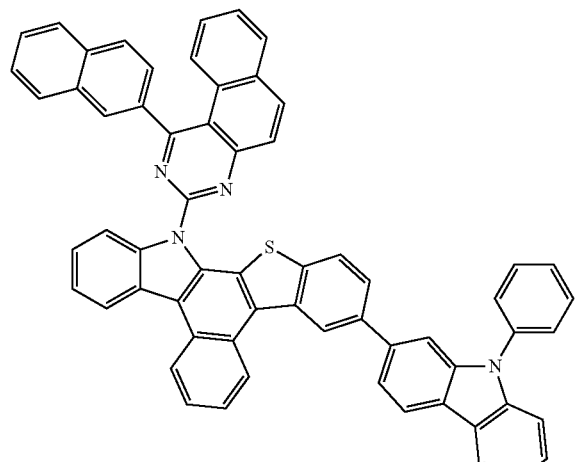
1-11
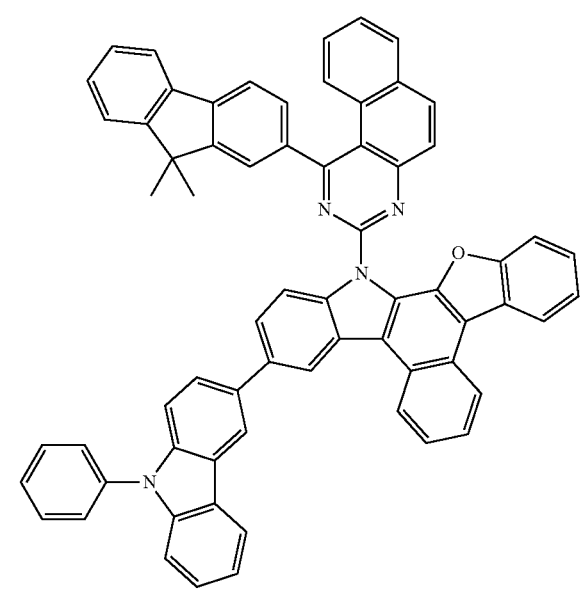
1-9
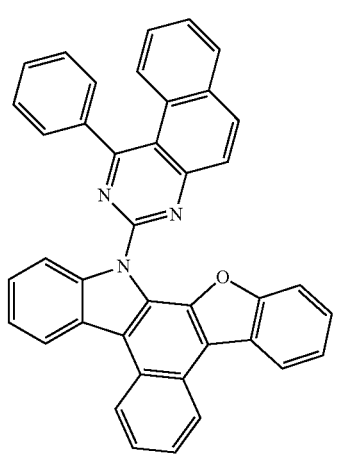
1-12
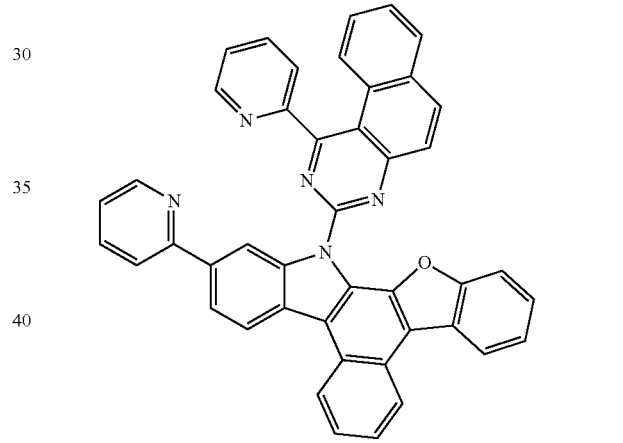
1-10
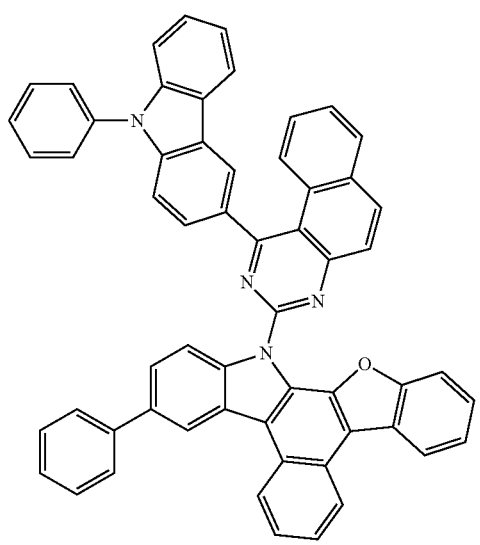
1-13
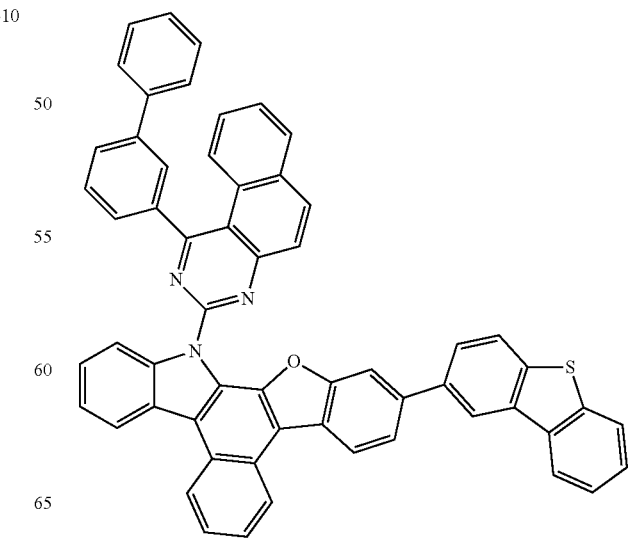

-continued
1-14
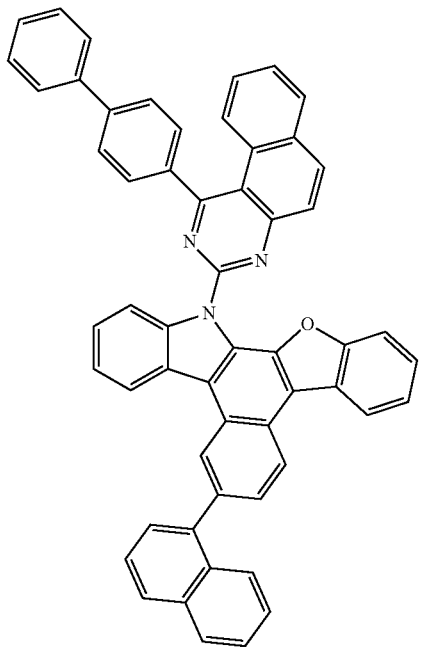
1-16
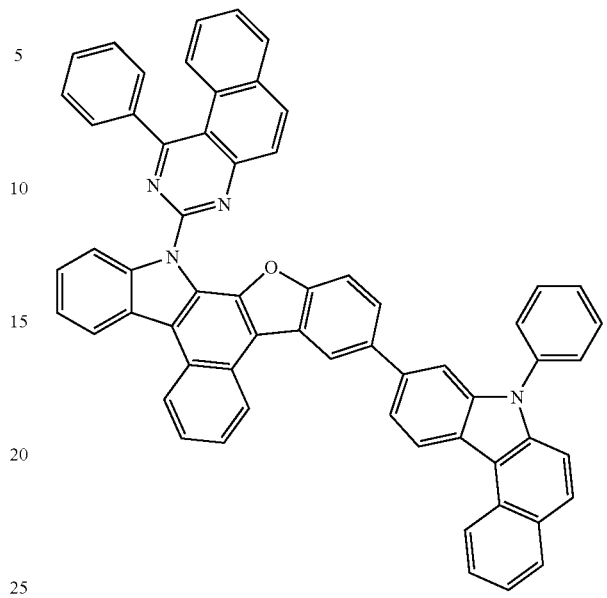
1-17
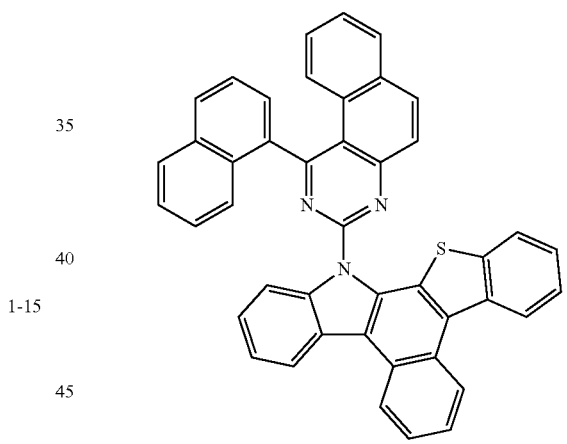
1-15
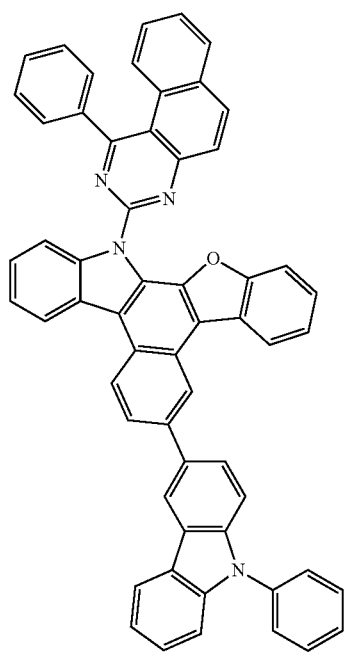
1-18
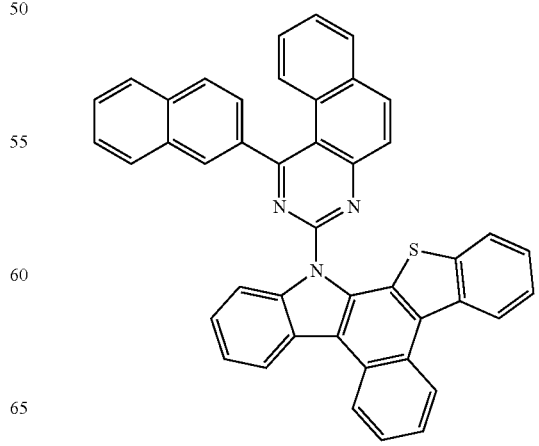

-continued
1-19
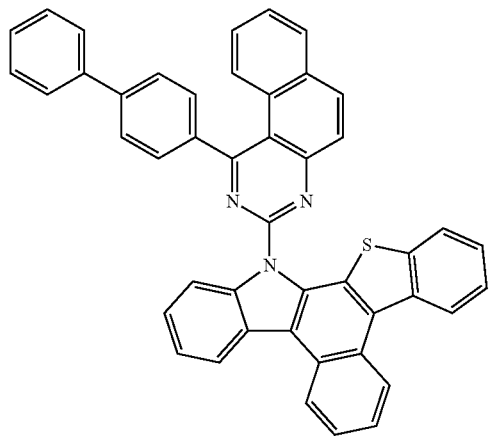
1-20
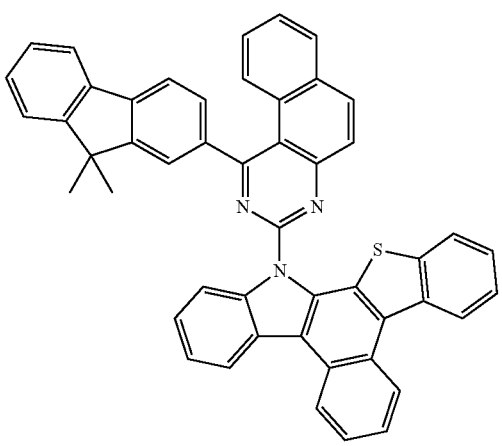
1-21
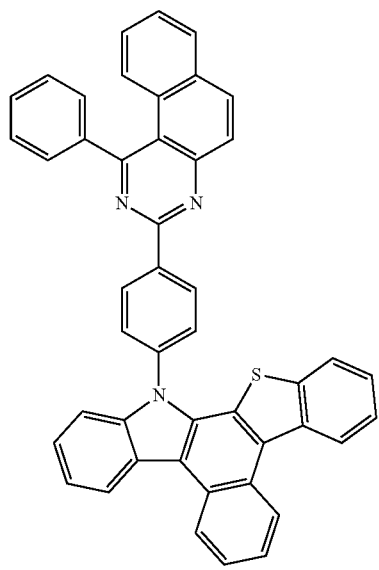
-continued
1-22
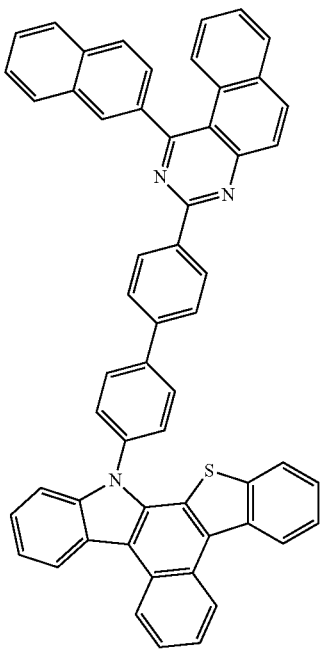
1-23
1-24
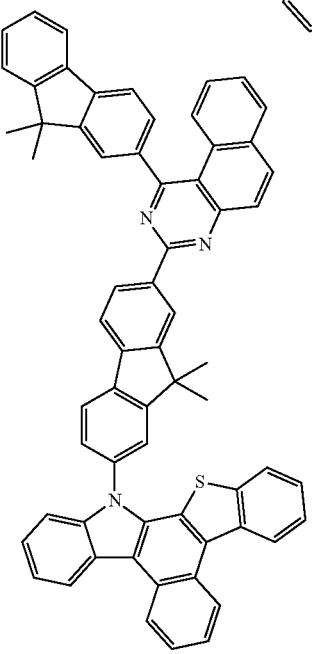

1-25
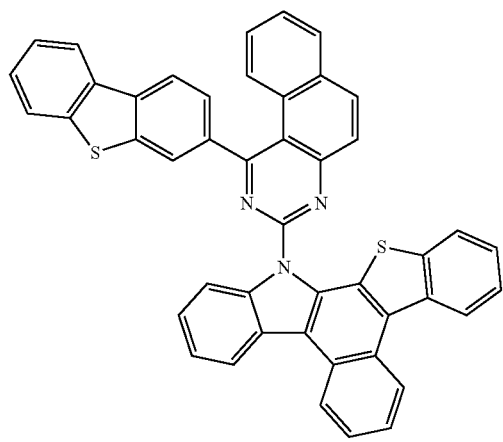
1-28
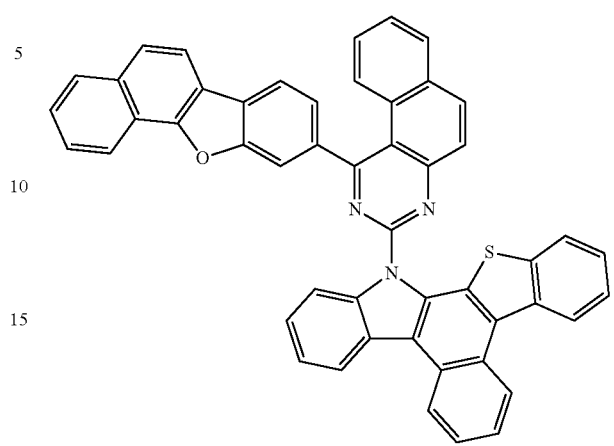
1-26
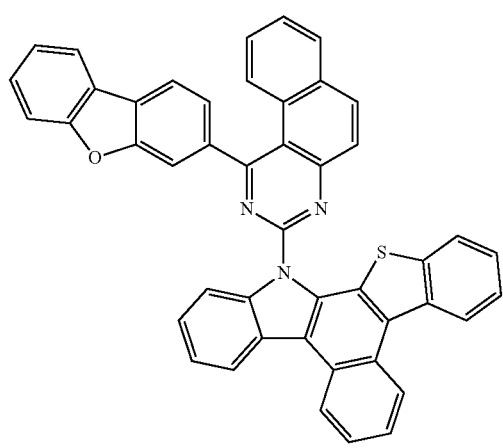
2-1
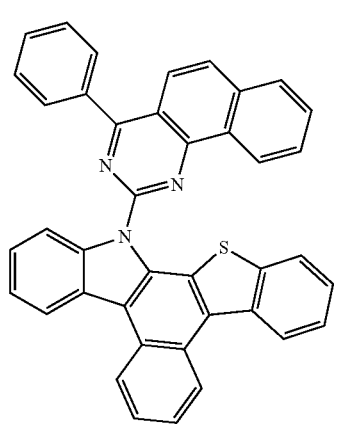
1-27
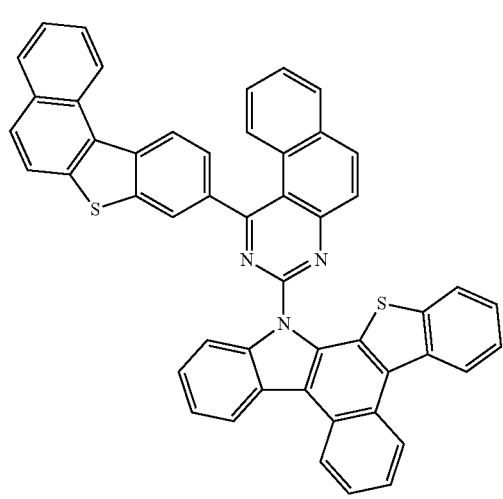
2-2
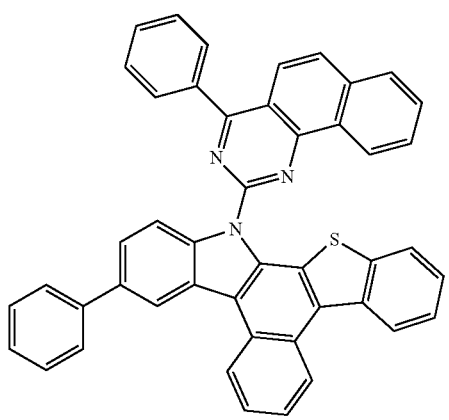

2-3
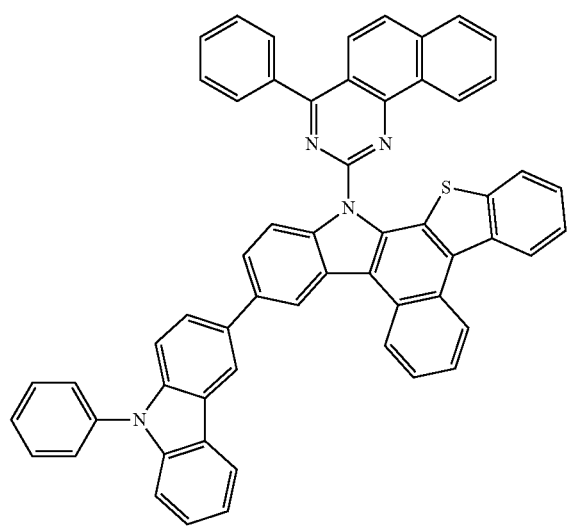
2-4
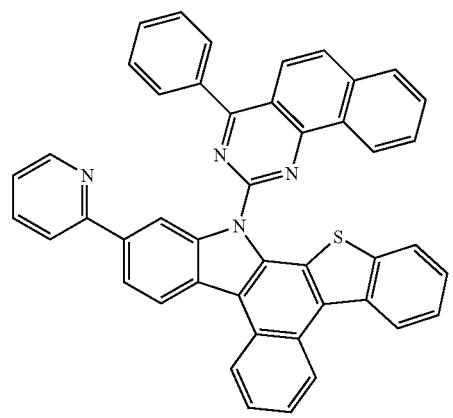
2-5
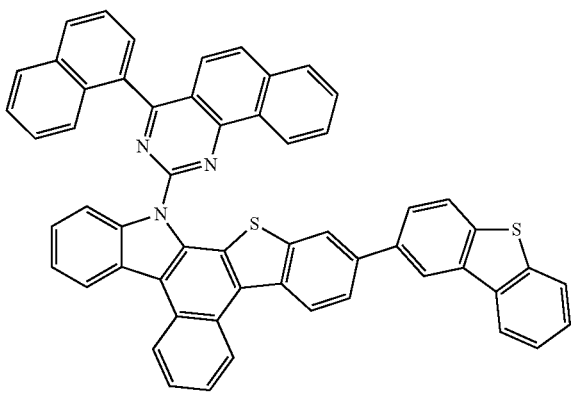
2-6
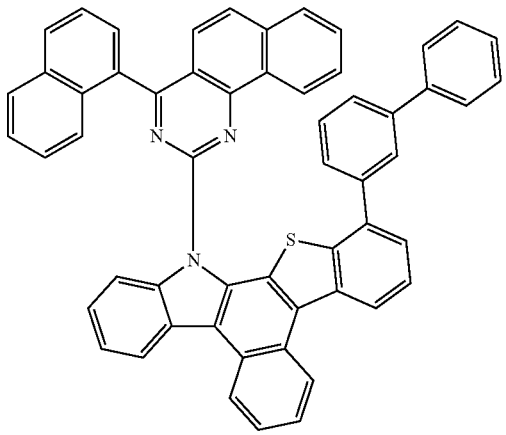
2-7
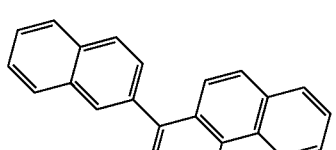
2-8
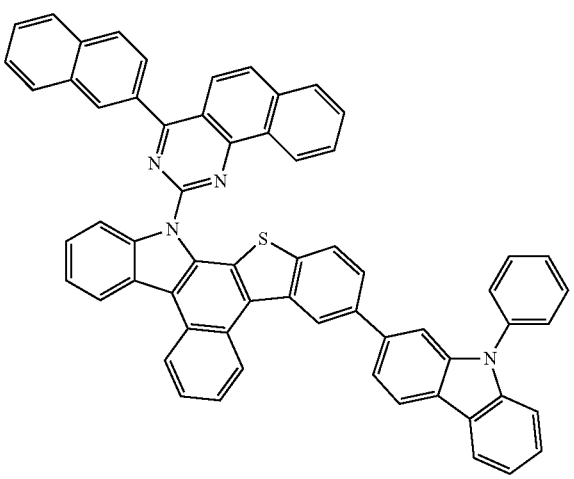

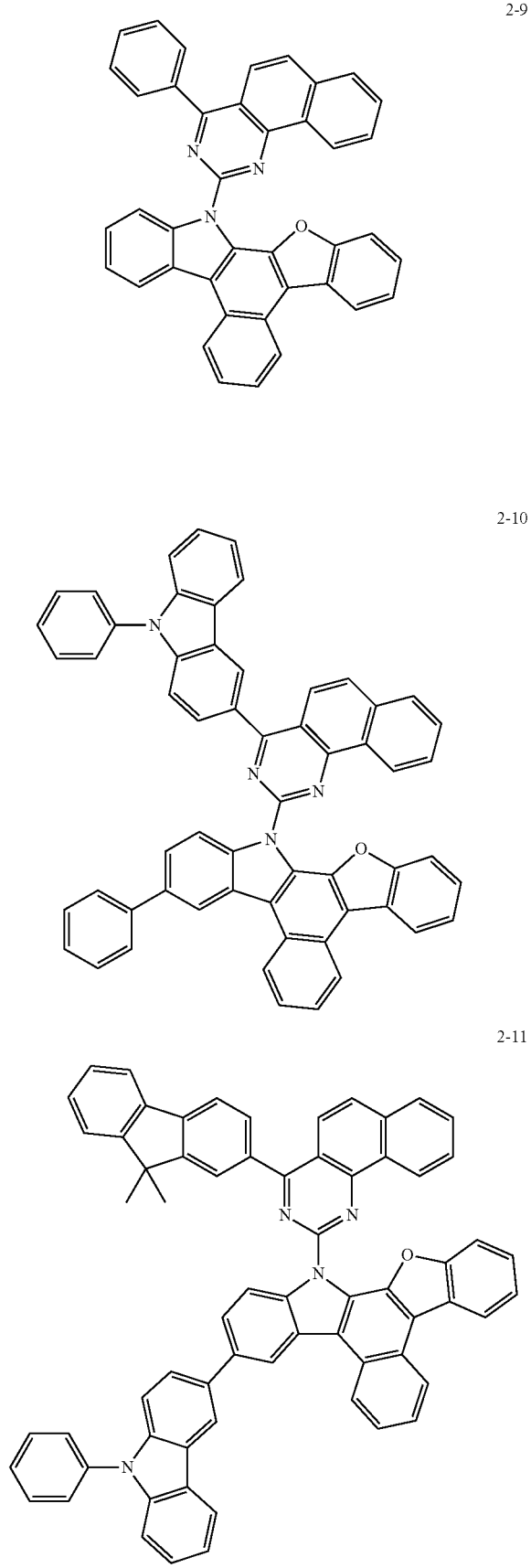

-continued
2-15
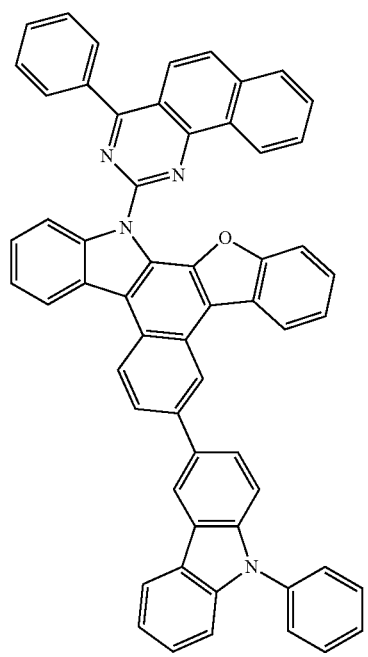
2-16
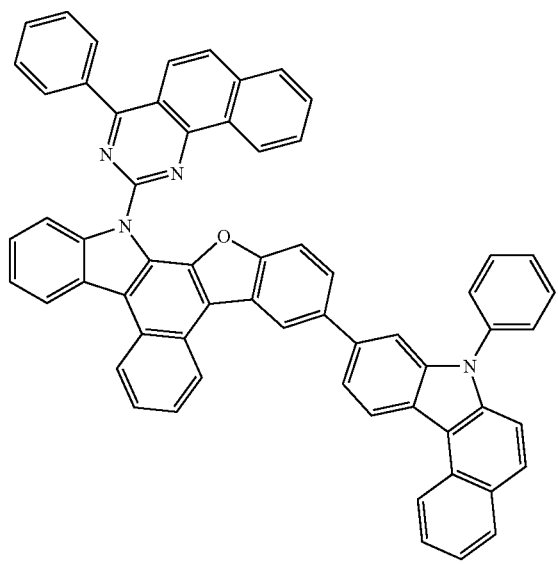
2-17
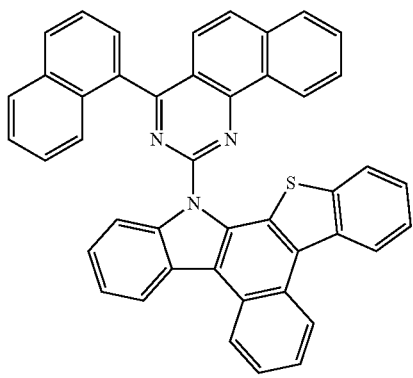
-continued
2-18
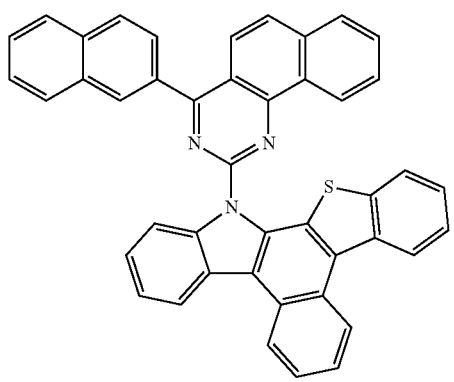
2-19
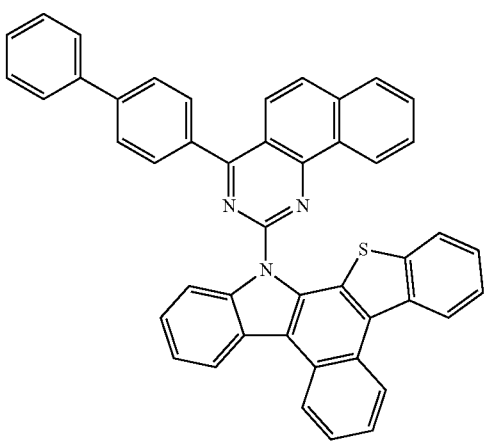
2-20
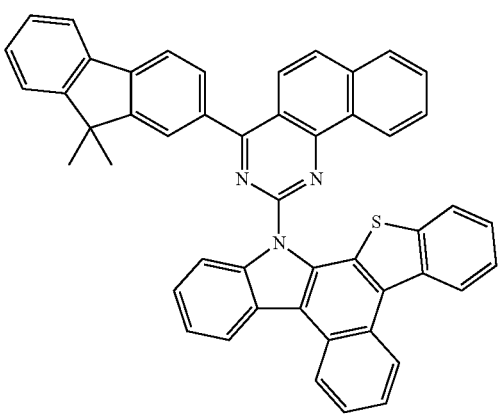

2-21
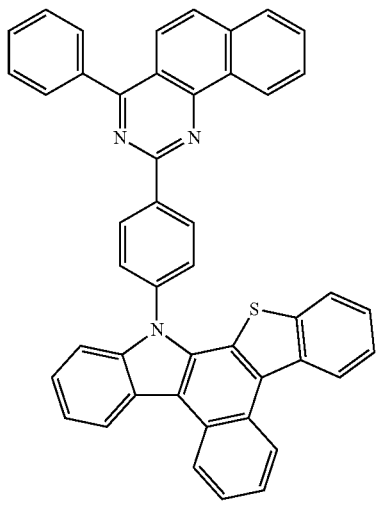
2-22
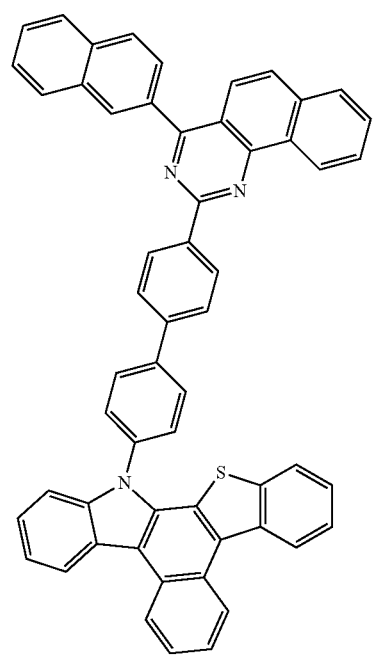
2-23
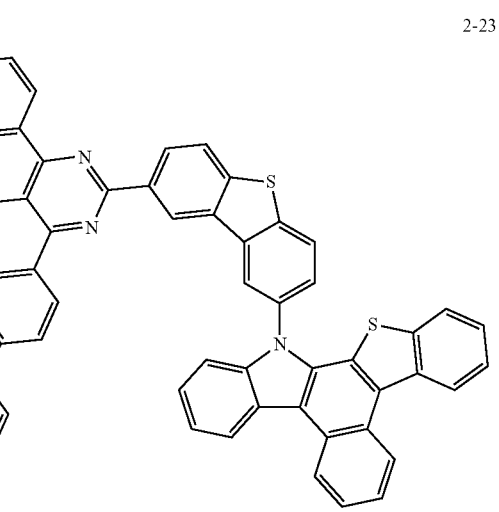
2-24
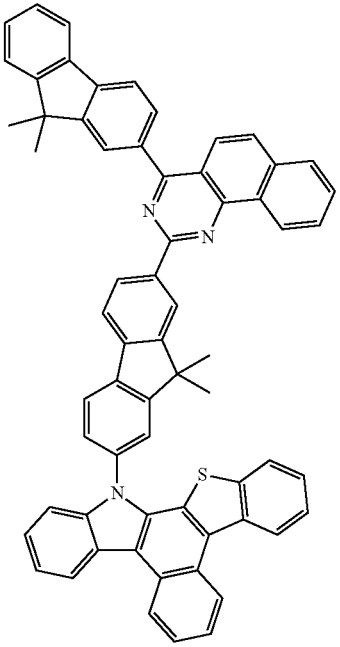
2-25
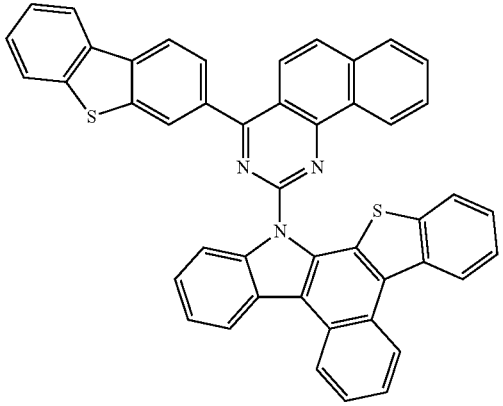
2-26
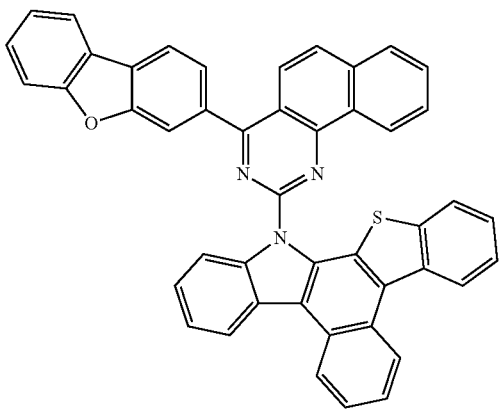

-continued
2-27
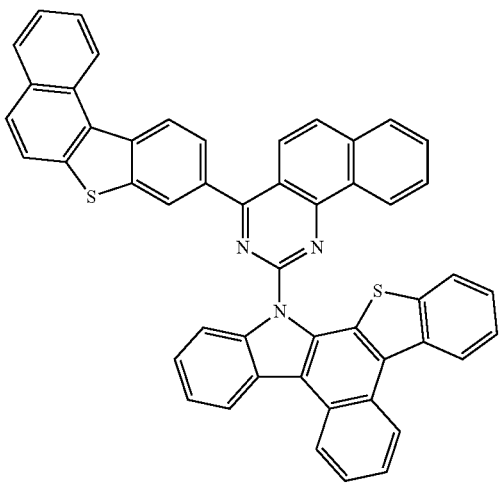
2-28
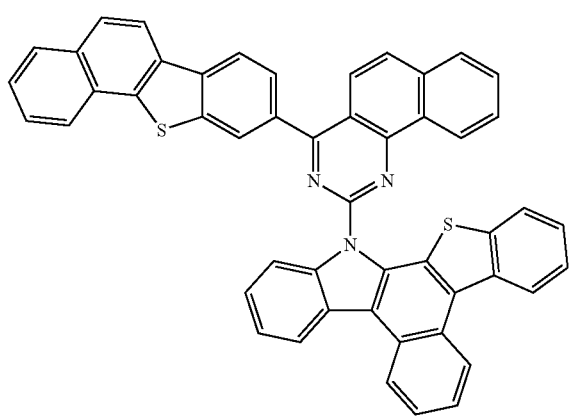
3-1
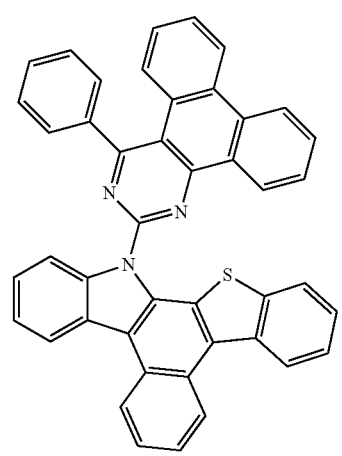
3-2
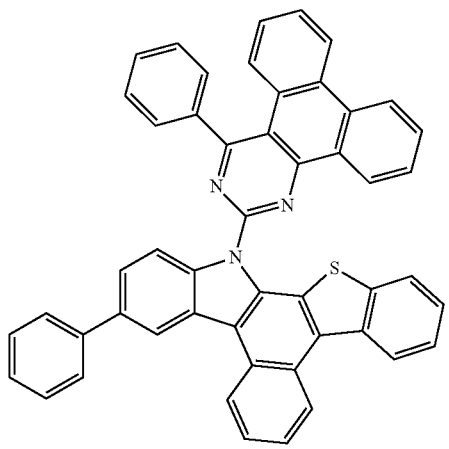
3-3
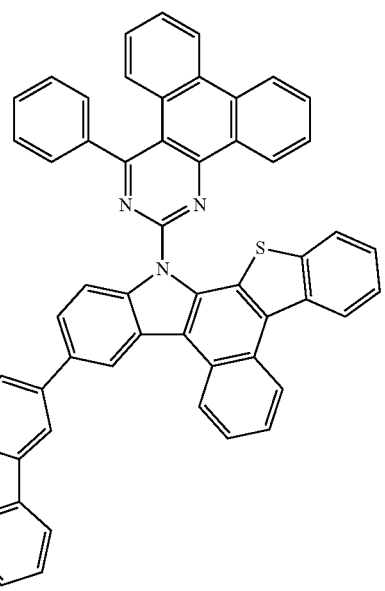
3-4
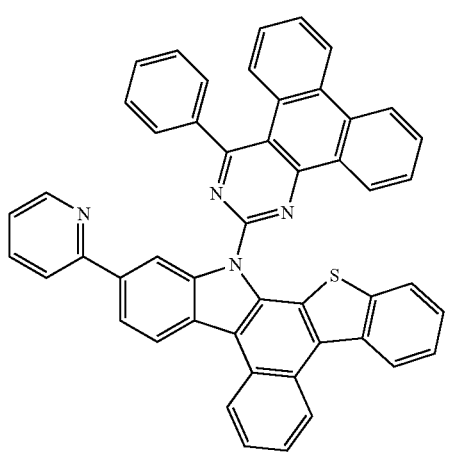

-continued
3-5
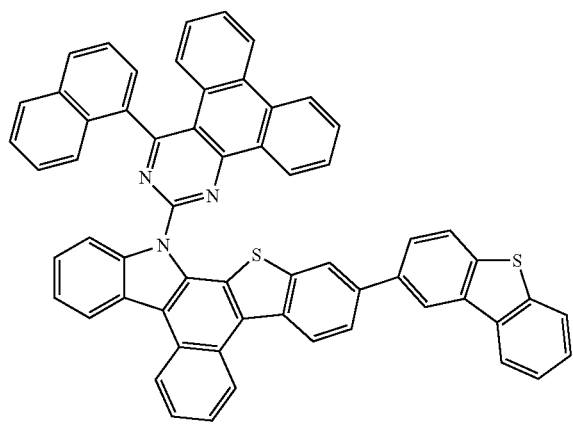
3-6
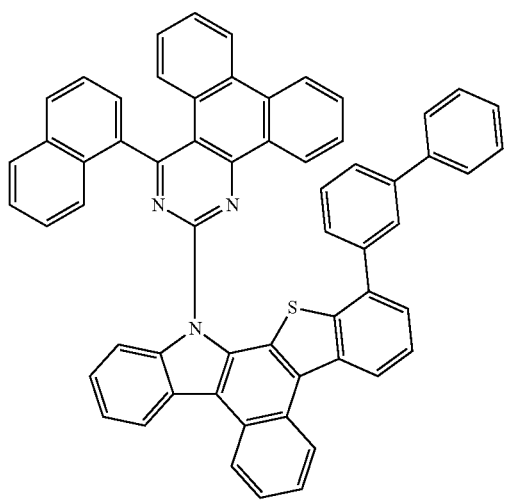
3-7
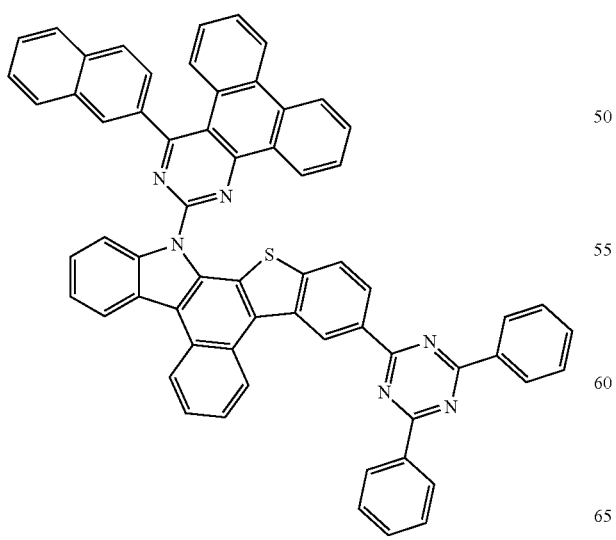
-continued
3-8
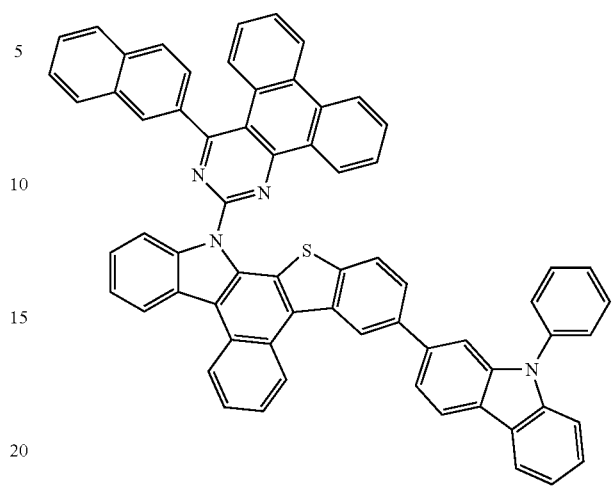
3-9
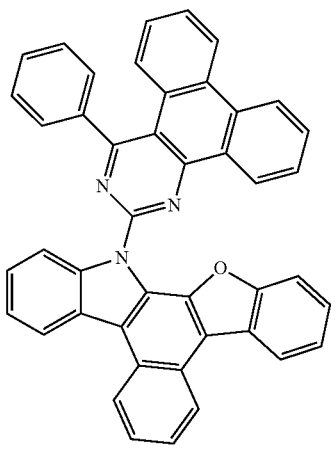
3-10
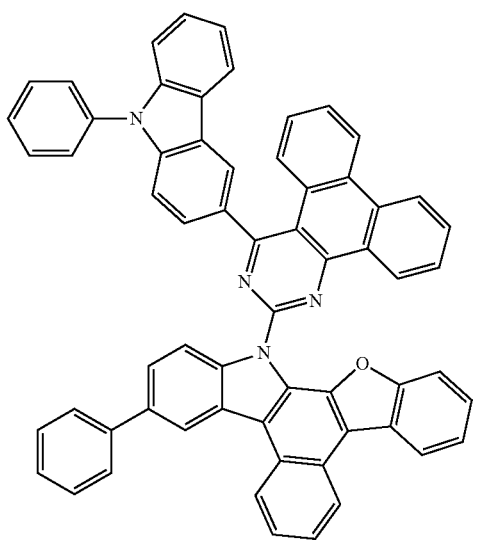

3-11
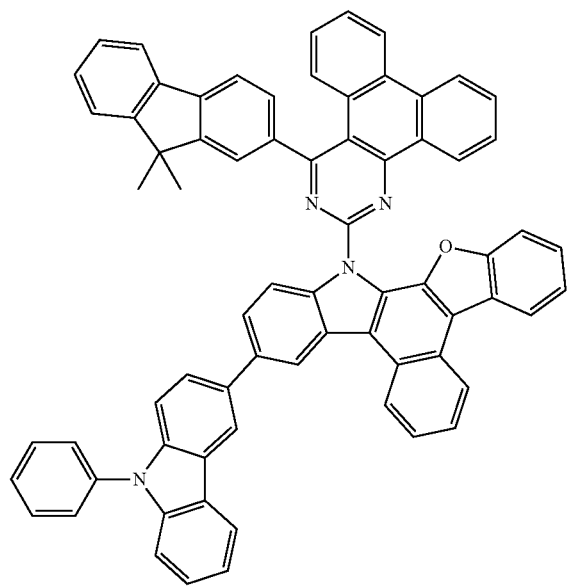
3-12
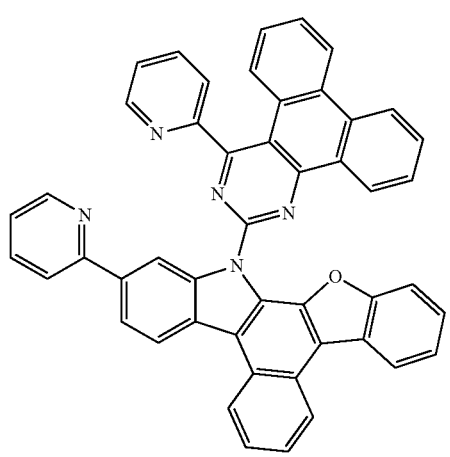
3-13
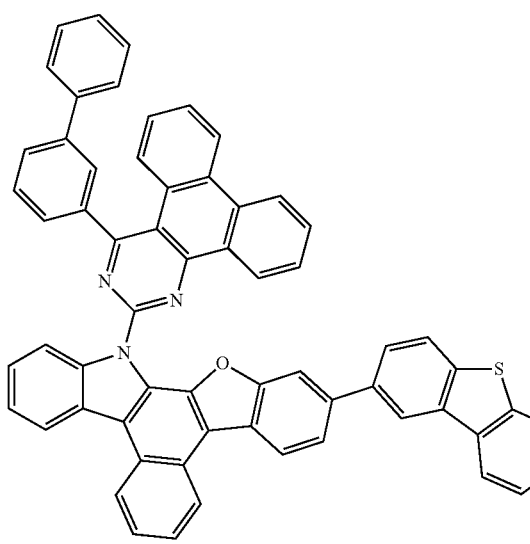
3-14
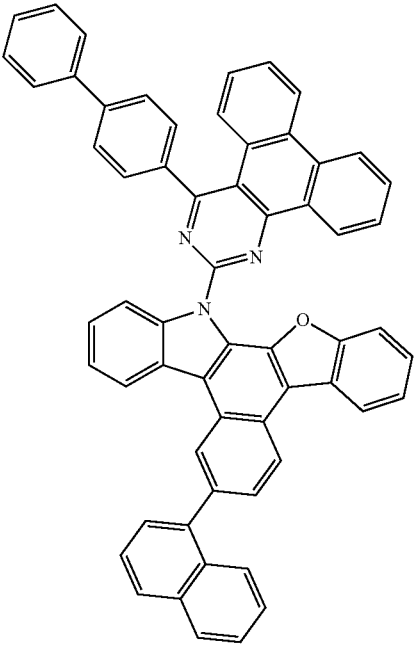
3-15
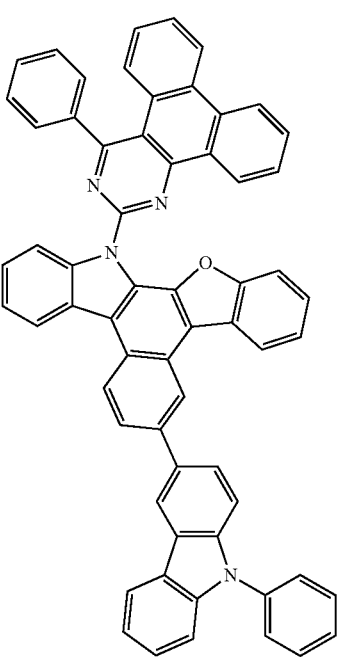

3-16
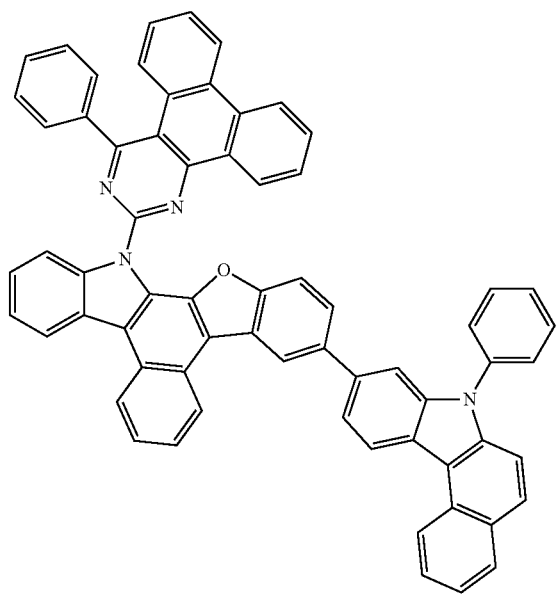
3-17
3-18
3-19
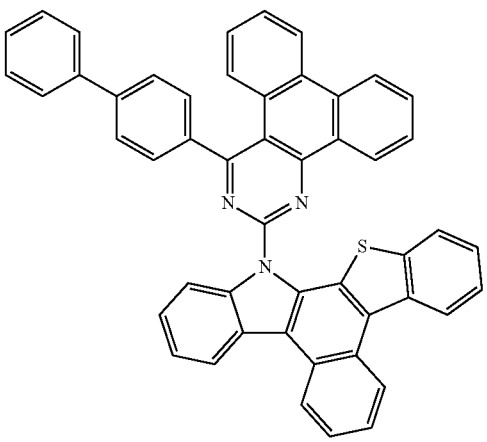
3-20
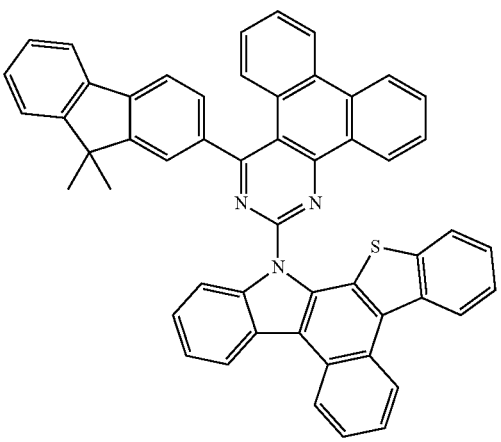
3-21
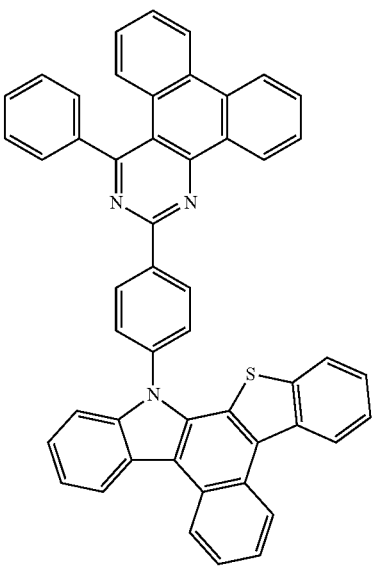

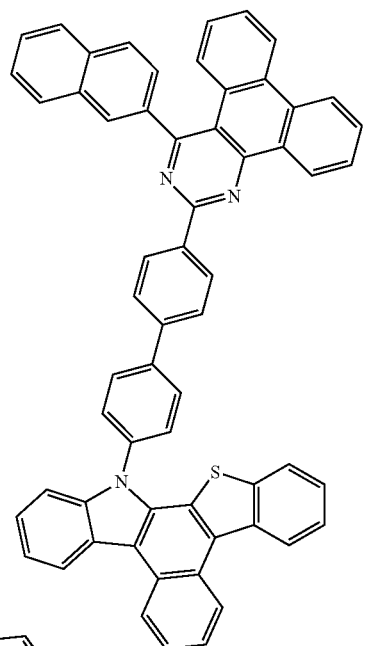
3-22
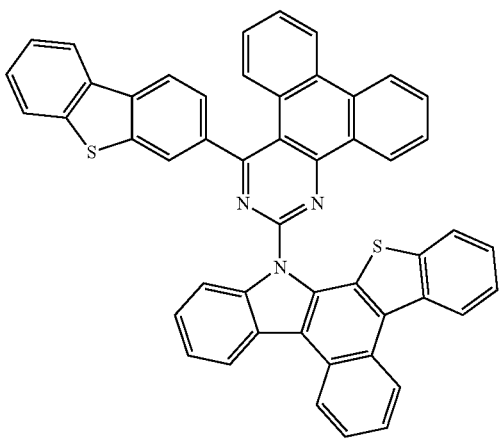
3-25
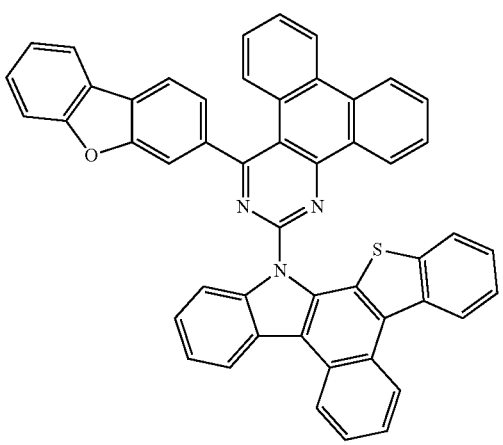
3-26
3-23
3-24
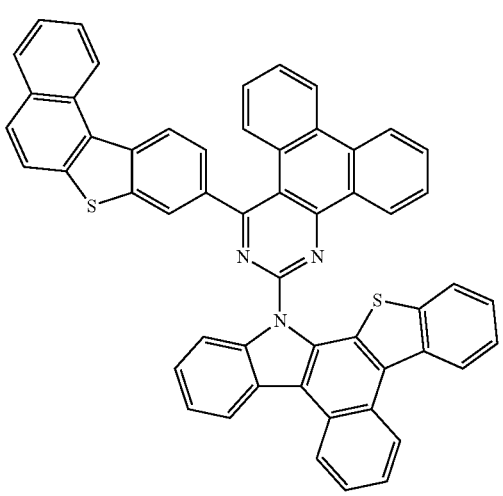
3-27

3-28

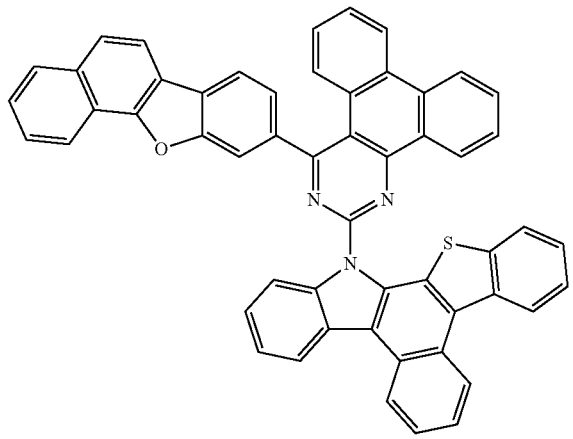

In another aspect of the present invention, this provides the organic electric element comprising a first electrode, a second electrode, and an organic material layer disposed between the first electrode and the second electrode.

The organic material layer can be in at least one layer of a hole injection layer, a hole transport layer, a light emitting layer, and an emission-auxiliary layer. And the organic material layer can comprise at least one of the compounds above. Also, the organic material layer can be composed one kind or two or more different kinds of the compounds represented by Formula 1 above.

Preferably, the light emitting layer of an organic material layer can comprise one kind or two or more different kinds of the compounds represented by Formula 1 above. And the compounds represented by Formula 1 above can comprise as a hose material of a light emitting layer, in particular, a phosphorescent red host material.

In another aspect of the present invention, when the compound represented by Formula 1 may be used as a host material of a light emitting layer, the following compound represented by Formula 6 can preferably be used as a dopant material. In other words, the compound represented by the following Formula 6 can be contained as the dopant in the light emitting layer of the present invention.

[Formula 6]

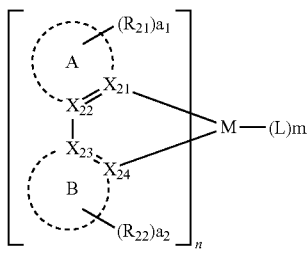

In Formula 6, each symbol may be defined as follows.
n may be an integer of 1 to 3.

A ring and B ring may be independently selected from the group consisting of a $C_4$-$C_{20}$ cycloalkyl group, a $C_2$-$C_{20}$ heterocyclo alkyl group, a $C_6$-$C_{60}$ aryl group, a fluorenyl group, a $C_2$-$C_{60}$ heteroarylene group selected from the group consisting of O, N, S, Si and P, and a fused ring group of $C_3$-$C_{60}$ aliphatic ring and a $C_6$-$C_{60}$ aromatic ring. Preferably, A ring and B ring may be independently selected from a group consisting of cyclopentene, cyclohexene, benzene, naphthalene, indene, fluorene, pyrrole, imidazole, pyrazole, pyridine, pyrazine, pyrimidine, pyridazine, indole, quinoline, isoquinoline, benzimidazole, furan, benzofuran, thiophene, benzothiophene, thiazole, isothiazole, oxazole, isoxazole, benzothiazole, and benzoxazole.

$X_{21}$ to $X_{24}$ may be independently carbon or nitrogen, preferably, at least one nitrogen.

$R_{21}$ and $R_{22}$ may be independently selected from the group consisting of deuterium, halogen, hydroxyl group, cyano group, nitro group, amino group, amidino group, hydrazine group, hydrazone group, carboxyl group or carboxylic acid salt, phosphoric acid or phosphoric acid salt, —C(=O)$Q_1$ (herein, $Q_1$ is a $C_1$-$C_{10}$ alkyl group, a $C_6$-$C_{10}$ aryl group or a $C_6$-$C_{60}$ aryloxy group), substituted or unsubstituted $C_1$-$C_{60}$ alkyl group, substituted or unsubstituted $C_2$-$C_{60}$ alkenyl group, substituted or unsubstituted $C_2$-$C_{60}$ alkynyl group, substituted or unsubstituted $C_1$-$C_{60}$ alkoxy group, substituted or unsubstituted $C_3$-$C_{60}$ cycloalkyl group, substituted or unsubstituted $C_2$-$C_{60}$ heterocycloalkyl group, substituted or unsubstituted $C_3$-$C_{60}$ cycloalkenyl group, substituted or unsubstituted $C_2$-$C_{60}$ heterocycloalkenyl group, substituted or unsubstituted $C_6$-$C_{60}$ aryl group, substituted or unsubstituted $C_6$-$C_{60}$ aryloxy group, substituted or unsubstituted $C_6$-$C_{60}$ arylthio group, and substituted or unsubstituted $C_2$-$C_{60}$ heteroaryl group, $a_1$ and $a_2$ may be independently an integer of 0 to 8. When $a_1$ and $a_2$ may be an integer 2 or more, plural $R_{21}$s and $R_{22}$s may be independently the same or different. Preferably, $R_{21}$ and $R_{22}$ may be independently selected from the group consisting of deuterium, —F, —Cl, cyano group, nitrogen group, —C(=O)$Q_1$($Q_1$ is methyl or phenyl group), methyl group, ethyl group, tert-butyl group, methoxy group, tert-butoxy group, and phenyl group. Herein, the methyl group, ethyl group, and tert-butyl group may be respectively substituted by at least one from the group consisting of deuterium, —F, —Cl, cyano group and nitro group. The phenyl group may be substituted at least one from the group consisting of deuterium, —F, —Cl, cyano group, nitro group, —C(=O)$Q_1$($Q_1$ is methyl or phenyl group), methyl group, tert-butyl group, methoxy group and tert-butoxy group.

M may be a transition metal having an atomic weight of 40 or more, preferably, M may be Iridium (Ir), Platinum (Pt), Osmium (Os) or Ruthenium (Ru).

L may be a mono dentate organic ligand, bidentate organic ligand, tridentate organic ligand or tetradentate organic ligand. m may be an integer of 0 to 4. Preferably, L may be a radical form represented by one of the following formulas.

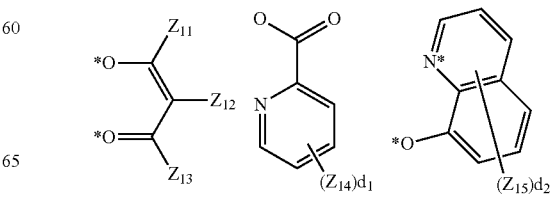

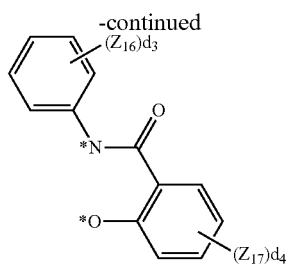

wherein, $Z_{11}$ to $Z_{17}$ may be independently selected from the group consisting of hydrogen, deuterium, halogen, hydroxyl group, cyano group, nitro group, $C_1$-$C_{60}$ alkyl group, $C_1$-$C_{60}$ alkoxy group, $C_6$-$C_{60}$ aryl group and $C_2$-$C_{60}$ heteroaryl group, and then $d_1$ to $d_4$ may be an integer of 1 to 4.

When $Z_{11}$ to $Z_{17}$ may be $C_1$-$C_{60}$ alkyl group or $C_1$-$C_{60}$ alkoxy group, the alkyl group and alkoxy may be optionally substituted by one or more substituents selected from the group consisting of deuterium, halogen, hydroxy group, cyano group and nitro group, and when $Z_{11}$ to $Z_{17}$ may be $C_6$-$C_{60}$ aryl group or $C_2$-$C_{60}$ heteroaryl group, the aryl group and heteroaryl may be optionally substituted by one or more substituents selected from the group consisting of deuterium, halogen, hydroxy group, cyano group, nitro group, $C_1$-$C_{60}$ alkyl group and $C_1$-$C_{60}$ alkoxy group.

The compound represented by Formula 6 above may be represented by any one of the following formulas.

[Formula 6-1]

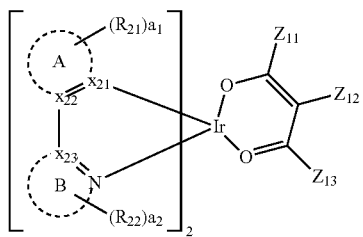

[Formula 6-2]

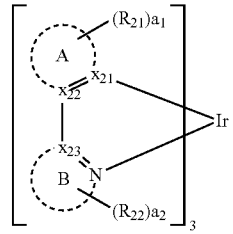

In Formula 6-1 and 6-2, each symbol may be as defined in Formula 6, these are preferably defined as follows.

A ring and B ring may be independently selected from the group consisting of cyclopentene, benzene, naphthalene, fluorene, pyridine, pyridazine, quinoline, isoquinoline, benzofuran, benzothiophene, thiazole, isothiazole, and benzoxazole.

$R_{21}$ and $R_{22}$ may be independently selected from the group consisting of deuterium, —F, —Cl, cyano group, nitro group, —C(=O)$Q_1$ (here, $Q_1$ is methyl or phenyl group), methyl group, ethyl group, tert-butyl group, methoxy group, tert-butoxy group and phenyl group. Herein, the methyl group, ethyl group, and tert-butyl group may be respectively substituted by at least one from the group consisting of deuterium, —F, —Cl, cyano group and nitro group. The phenyl group may be substituted at least one from the group consisting of deuterium, —F, —Cl, cyano group, nitro group, —C(=O)$Q_1$($Q_1$ is methyl or phenyl group), methyl group, tert-butyl group, methoxy group and tert-butoxy group. $a_1$ and $a_2$ may be independently an integer of 0 to 2.

$Z_{11}$ to $Z_{13}$ may be independently selected from the group consisting of hydrogen, deuterium, methyl group, ethyl group and tert-butyl group. And, the methyl group, ethyl group and tert-butyl group may be respectively substituted at least one from the group consisting of deuterium, —F, cyano group and nitro group.

Specifically, the compound represented by Formula 6 above may be represented by one of the following compounds.

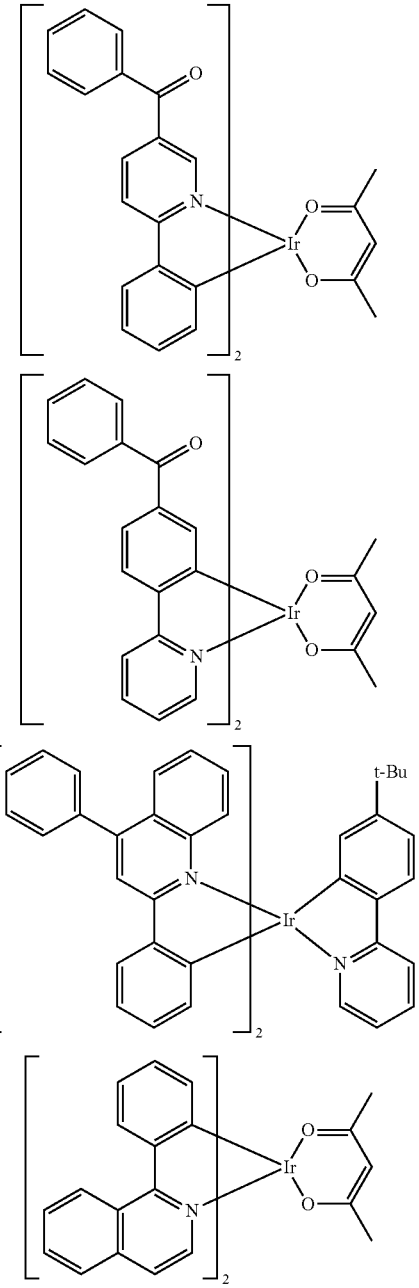

-continued
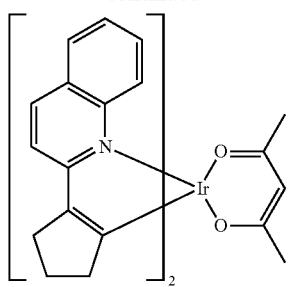
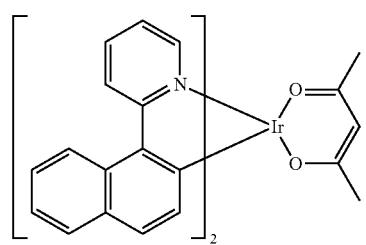
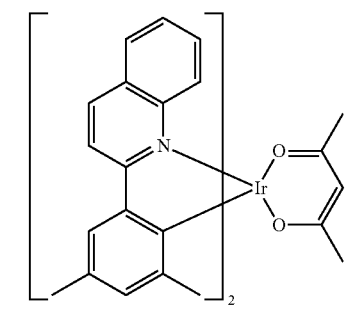
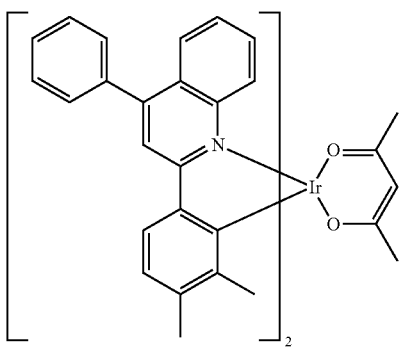
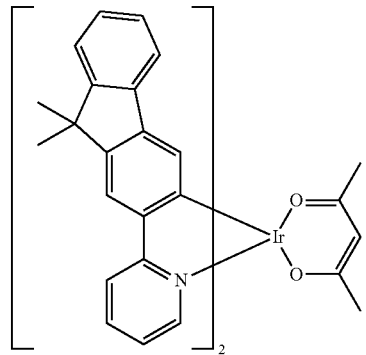
-continued
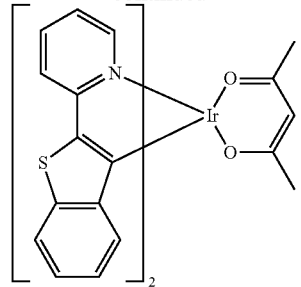
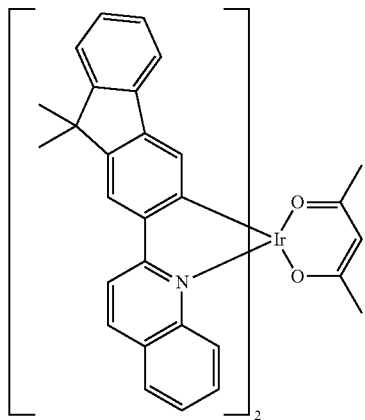
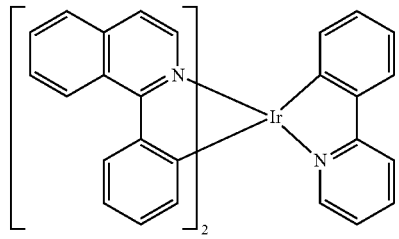
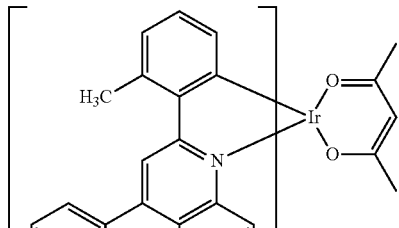
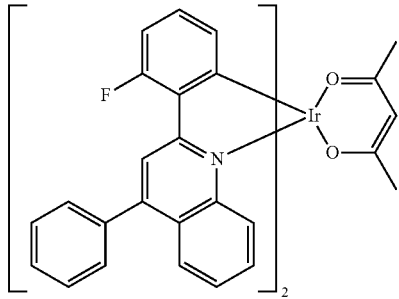

-continued
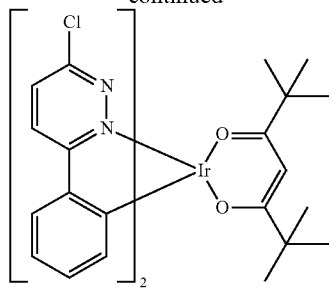
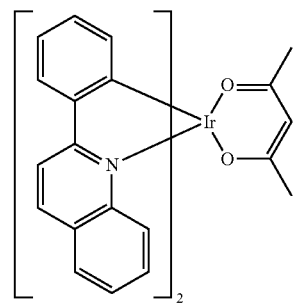
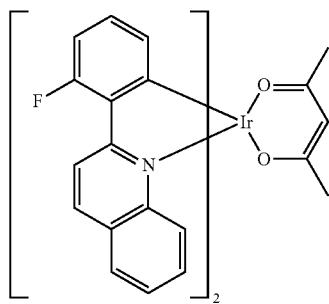
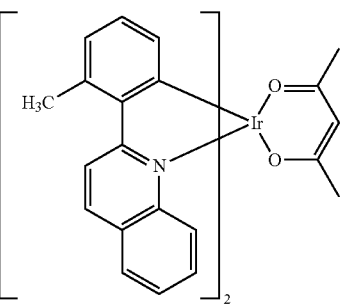
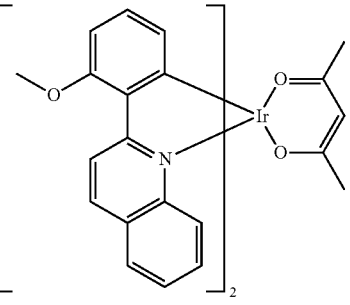
-continued
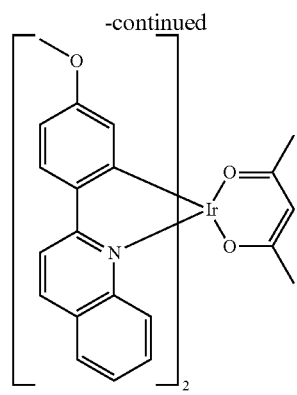
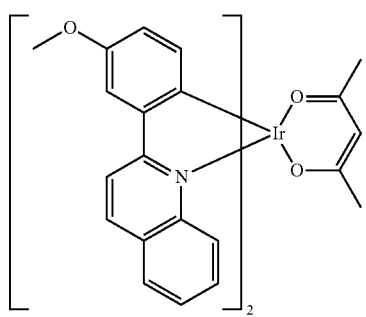
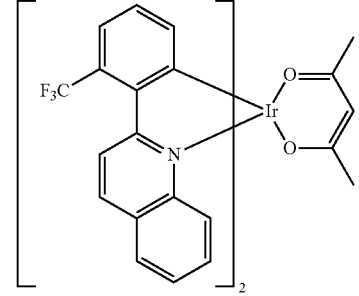
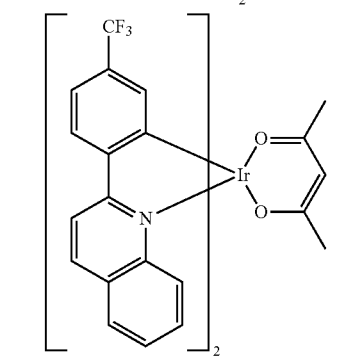
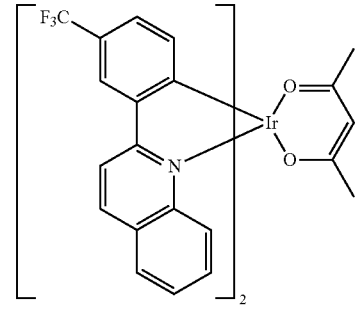

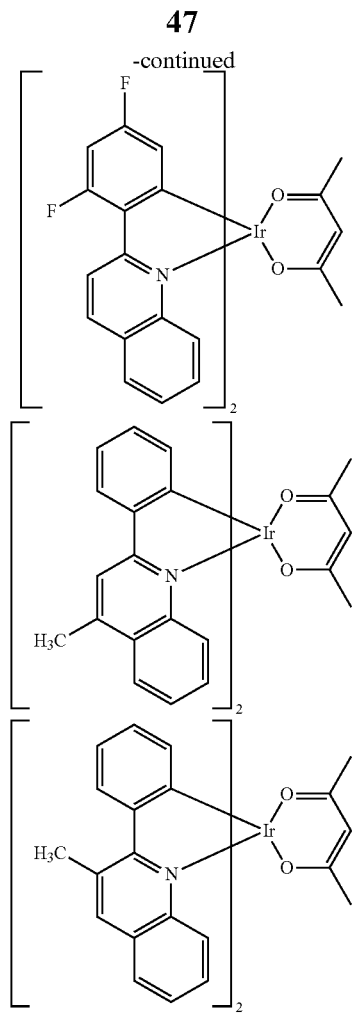

Hereinafter, Synthesis Examples of the compound represented by Formula 1 according to the present invention and Preparation Examples of an organic electric element will be described in detail by way of example. However, the following examples are only for illustrative purposes and are not intended to limit the scope of the invention.

SYNTHESIS EXAMPLE

The final product of the present invention, represented by Formula 1, can be synthesized by reaction between Sub 1 and Sub 2 as illustrated in, but not limited to, the following Reaction Scheme 1.

<Reaction Scheme 1>

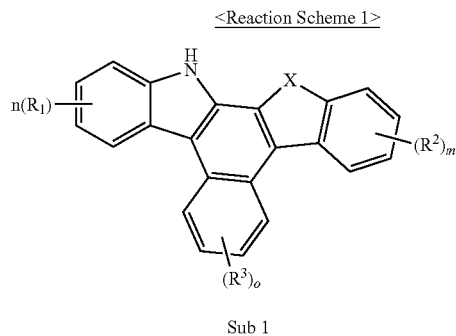

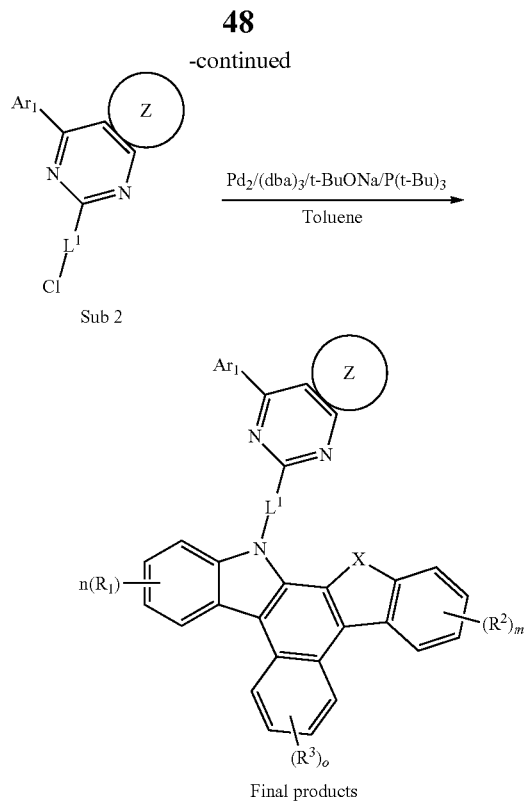

I. Synthesis Example of Sub 1

Sub 1 of the Reaction Scheme 1 can be synthesized according to, but not limited to, the following Reaction Scheme 2.

<Reaction Scheme 2>

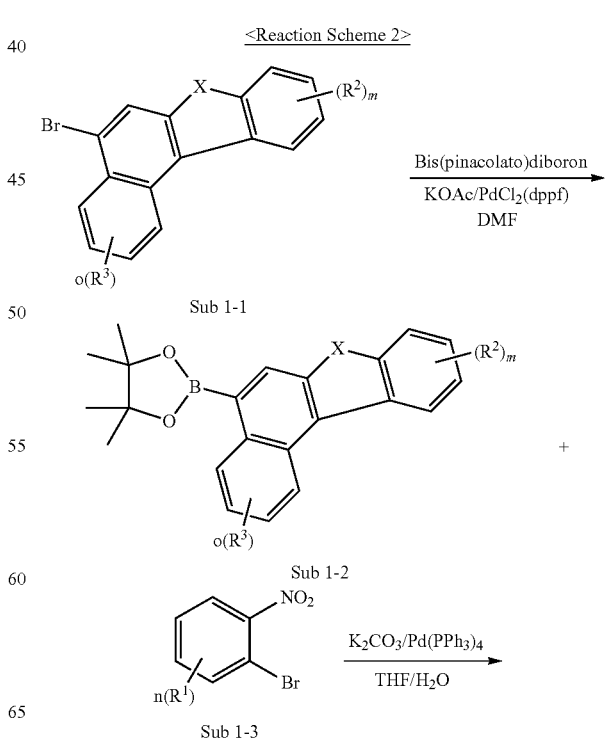

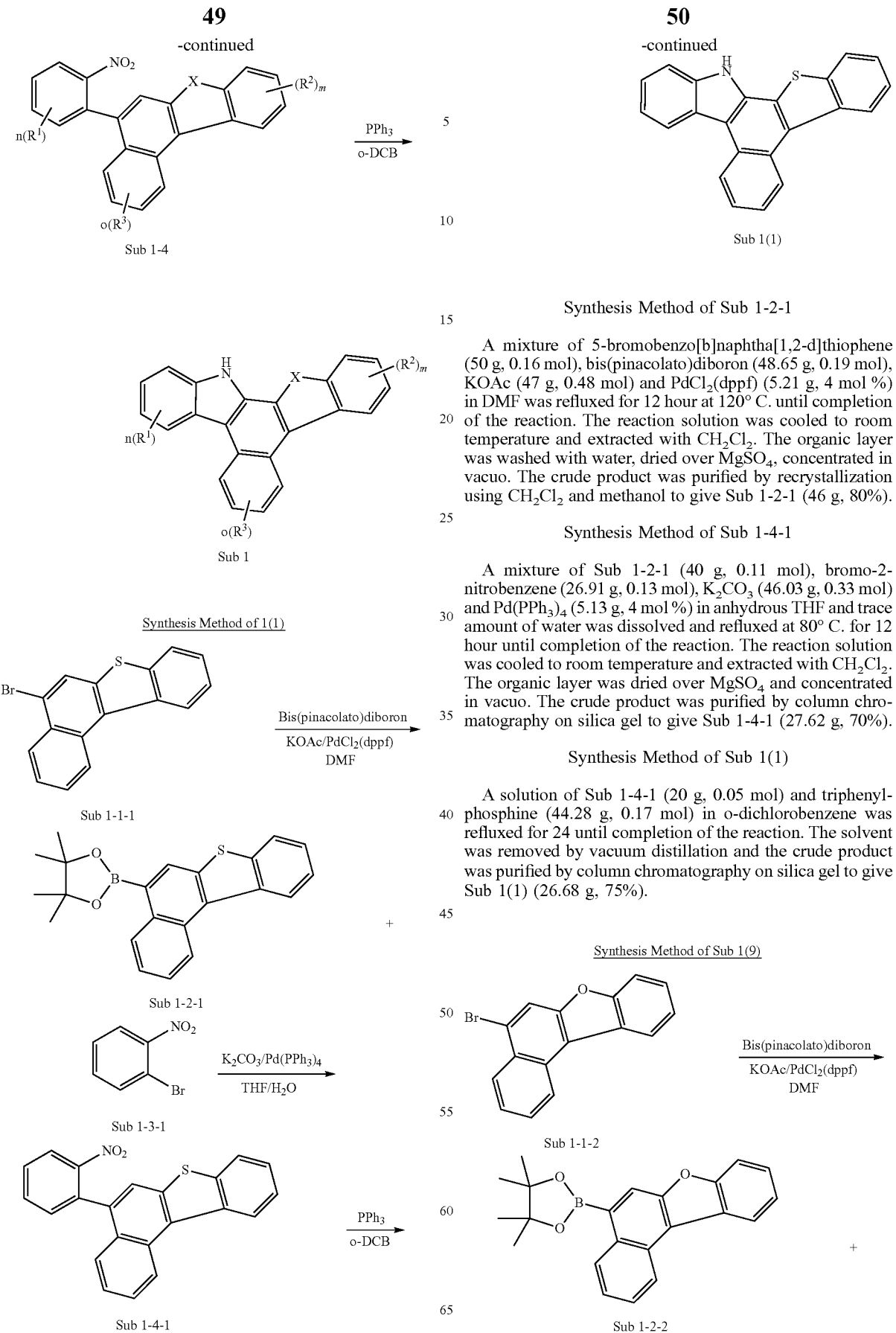

Synthesis Method of Sub 1-2-1

A mixture of 5-bromobenzo[b]naphtha[1,2-d]thiophene (50 g, 0.16 mol), bis(pinacolato)diboron (48.65 g, 0.19 mol), KOAc (47 g, 0.48 mol) and PdCl$_2$(dppf) (5.21 g, 4 mol %) in DMF was refluxed for 12 hour at 120° C. until completion of the reaction. The reaction solution was cooled to room temperature and extracted with CH$_2$Cl$_2$. The organic layer was washed with water, dried over MgSO$_4$, concentrated in vacuo. The crude product was purified by recrystallization using CH$_2$Cl$_2$ and methanol to give Sub 1-2-1 (46 g, 80%).

Synthesis Method of Sub 1-4-1

A mixture of Sub 1-2-1 (40 g, 0.11 mol), bromo-2-nitrobenzene (26.91 g, 0.13 mol), K$_2$CO$_3$ (46.03 g, 0.33 mol) and Pd(PPh$_3$)$_4$ (5.13 g, 4 mol %) in anhydrous THF and trace amount of water was dissolved and refluxed at 80° C. for 12 hour until completion of the reaction. The reaction solution was cooled to room temperature and extracted with CH$_2$Cl$_2$. The organic layer was dried over MgSO$_4$ and concentrated in vacuo. The crude product was purified by column chromatography on silica gel to give Sub 1-4-1 (27.62 g, 70%).

Synthesis Method of Sub 1(1)

A solution of Sub 1-4-1 (20 g, 0.05 mol) and triphenylphosphine (44.28 g, 0.17 mol) in o-dichlorobenzene was refluxed for 24 until completion of the reaction. The solvent was removed by vacuum distillation and the crude product was purified by column chromatography on silica gel to give Sub 1(1) (26.68 g, 75%).

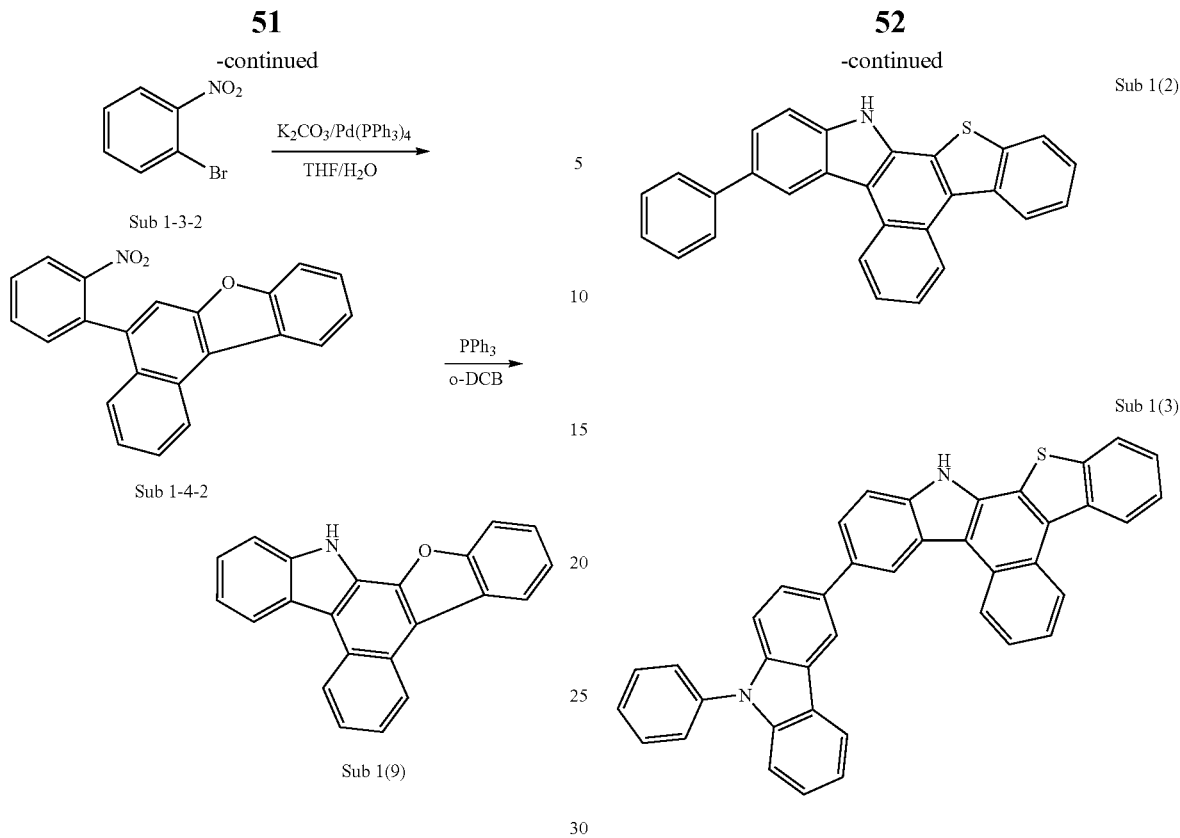

Synthesis Method of Sub 1-2-2

Sub 1-2-2 (43.0 g, 78%) was prepared from 5-bromonaphtho[2,1-b]benzofuran (47.5 g, 0.16 mol) as a starting material according to the same way used for Sub 1-2-1 above.

Synthesis Method of Sub 1-4-2

Sub 1-4-2 (29.3 g, 69%) was prepared from Sub 1-2-2 (43 g, 0.13 mol) according to the same was used for Sub 1-4-1 above.

Synthesis Method of Sub 1(9)

Sub 1(9) (19.4 g, 73%) was prepared from Sub 1-4-2 (29.3 g, 0.09 mol) according to the same way used for Sub 1(1) above.

Examples of Sub 1 compounds include, but are not limited to, the following compounds, and FD-MS data of the compounds are given in Table 1 below.

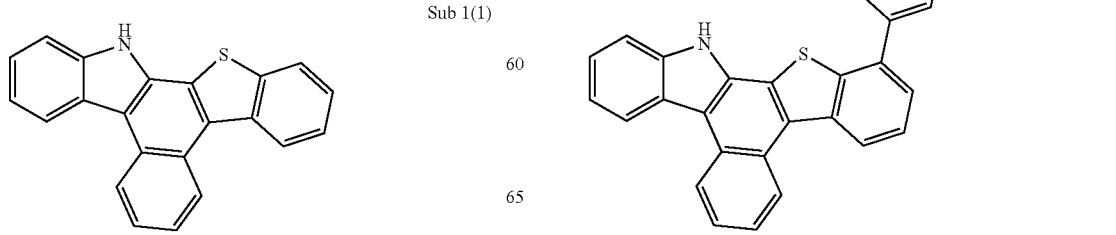

Sub 1(7)
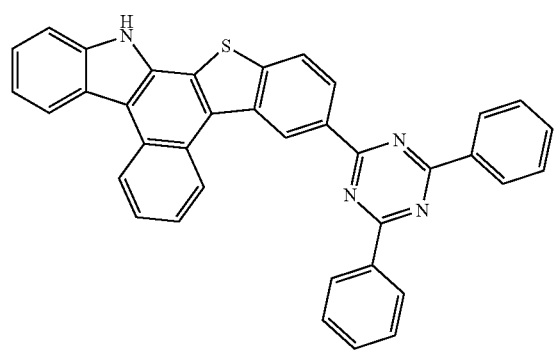
Sub 1(8)
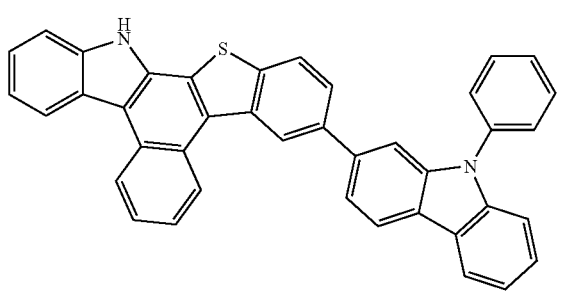
Sub 1(9)
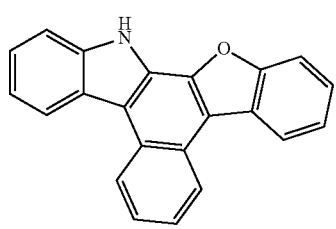
Sub 1(10)
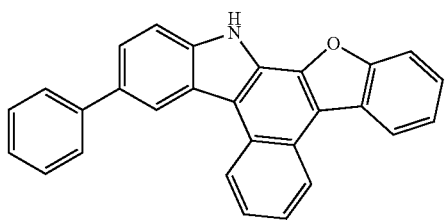
Sub 1(11)
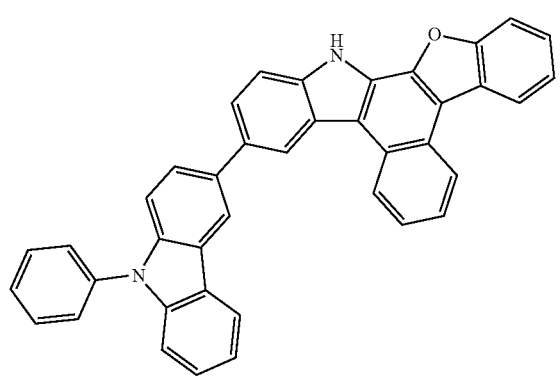
Sub 1(12)
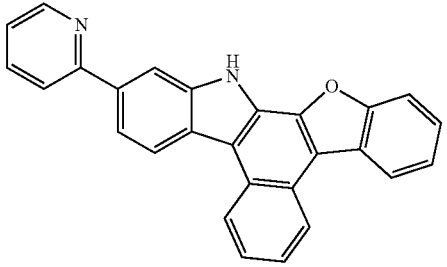
Sub 1(13)
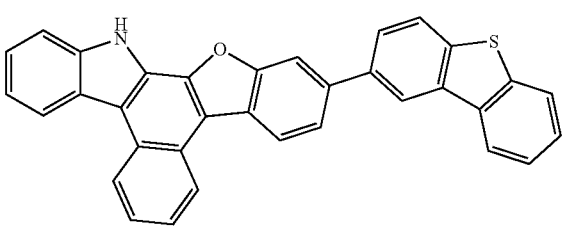
Sub 1(14)
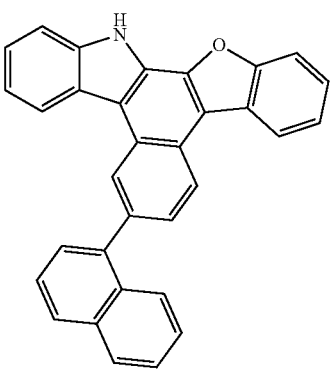
Sub 1(15)
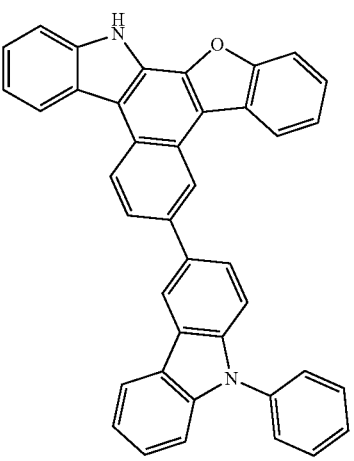

55
-continued

Sub 1(16)

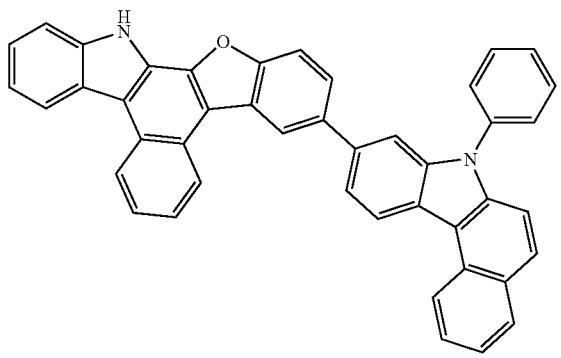

TABLE 1

| Compound | FD-MS |
| --- | --- |
| Sub 1 (1) | m/z = 323.08 ($C_{22}H_{13}NS$ = 323.41) |
| Sub 1 (2) | m/z = 399.11 ($C_{28}H_{17}NS$ = 399.51) |
| Sub 1 (3) | m/z = 564.17 ($C_{40}H_{24}N_2S$ = 564.70) |
| Sub 1 (4) | m/z = 400.10 ($C_{27}H_{16}N_2S$ = 400.49) |
| Sub 1 (5) | m/z = 505.10 ($C_{34}H_{19}NS_2$ = 505.65) |
| Sub 1 (6) | m/z = 475.14 ($C_{34}H_{21}NS$ = 475.60) |
| Sub 1 (7) | m/z = 554.16 ($C_{37}H_{22}N_4S$ = 554.66) |
| Sub 1 (8) | m/z = 564.17 ($C_{40}H_{24}N_2S$ = 564.70) |
| Sub 1 (9) | m/z = 307.10 ($C_{22}H_{13}NO$ = 307.34) |
| Sub 1 (10) | m/z = 383.13 ($C_{28}H_{17}NO$ = 383.44) |
| Sub 1 (11) | m/z = 548.19 ($C_{40}H_{24}N_2O$ = 548.63) |
| Sub 1 (12) | m/z = 384.13 ($C_{27}H_{16}N_2O$ = 384.43) |
| Sub 1 (13) | m/z = 489.12 ($C_{34}H_{19}NOS$ = 489.59) |
| Sub 1 (14) | m/z = 433.15 ($C_{32}H_{19}NO$ = 433.50) |
| Sub 1 (15) | m/z = 548.19 ($C_{40}H_{24}N_2O$ = 548.63) |
| Sub 1 (16) | m/z = 598.20 ($C_{44}H_{26}N_2O$ = 598.69) |

II. Synthesis Method of Sub 2

Sub 2 of the Reaction Scheme 1 can be synthesized according to, but not limited to, the following Reaction Scheme 3.

<Reaction Scheme 3>

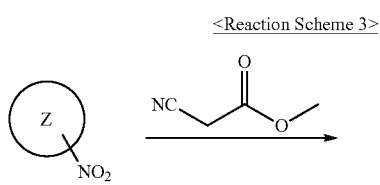

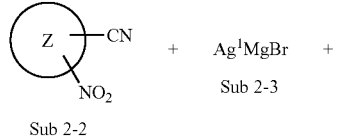

56
-continued

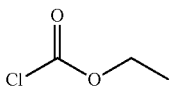

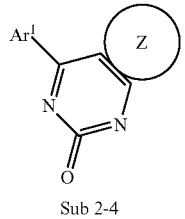

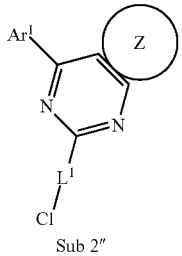

Synthesis method of Sub 2(9)

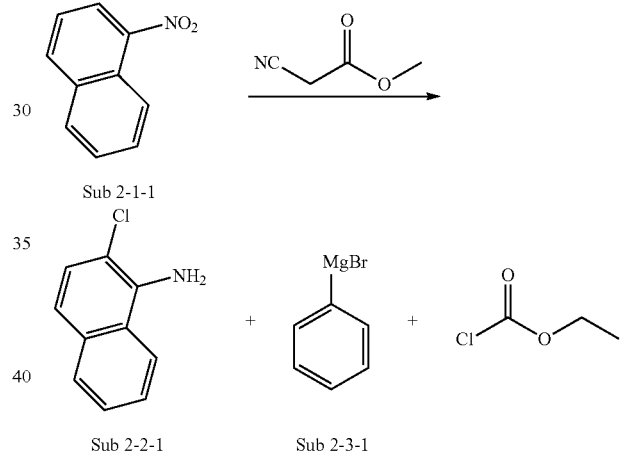

Synthesis Method of Sub 2-2-1

A mixture of Sub 2-1-1 (97 g, 0.56 mol), methyl cyanoacetate (166.5 g, 1.68 mol), KCN (40.1 g, 0.62 mol), KOH (62.9 g, 1.12 mol) was added 970 mL of DMF and stirred at 60° C. for overnight. The solvent was removed by evaporation under vacuum at room temperature. And then to the reaction mixture was added 500 mL of 10% KOH solution (aq.) and refluxed for 1 hour. The reaction solution was cooled to room temperature and extracted with ethylacetate. The organic layer was washed with water, dried over $MgSO_4$, concentrated in vacuo. The crude product was purified by column chromatography and recrystallization with toluene and heptane to give Sub 2-2-1 (54%).

Synthesis Method of Sub 2-4-1

To a solution of Sub 2-2-1 (25.0 g, 149 mmol) in 200 mL of anhydrous THF was stirred and slowly added dropwise phenyl magnesium bromide (3.0 M in Et2O) (87.4 mL, 297 mmol) at 0° C., and then refluxed for 1 hour. After that, ethyl chloroformate (19.4 g, 179 mmol) was added dropwise to the reaction solution and it was refluxed for 1 hour again.

The reaction solution was adjusted weak acid with ammonium chloride solution(aq.), and then, washed with water and heptane to give Sub 2-4-1 (32.4 g, 80%).

Synthesis Method of Sub 2(9)

A Sub 2-4-1 (30 g, 110 mmol) was added 80 mL of phosphorus oxychloride and refluxed for overnight. And then, the reaction solution was cooled to −20° C. and slowly added about 400 mL of water. The crude product was washed with water, methanol and heptane and purified by recrystallization with toluene and heptane to give Sub2(9) (14.1 g, 44%).

Synthesis Method of Sub 2(28)

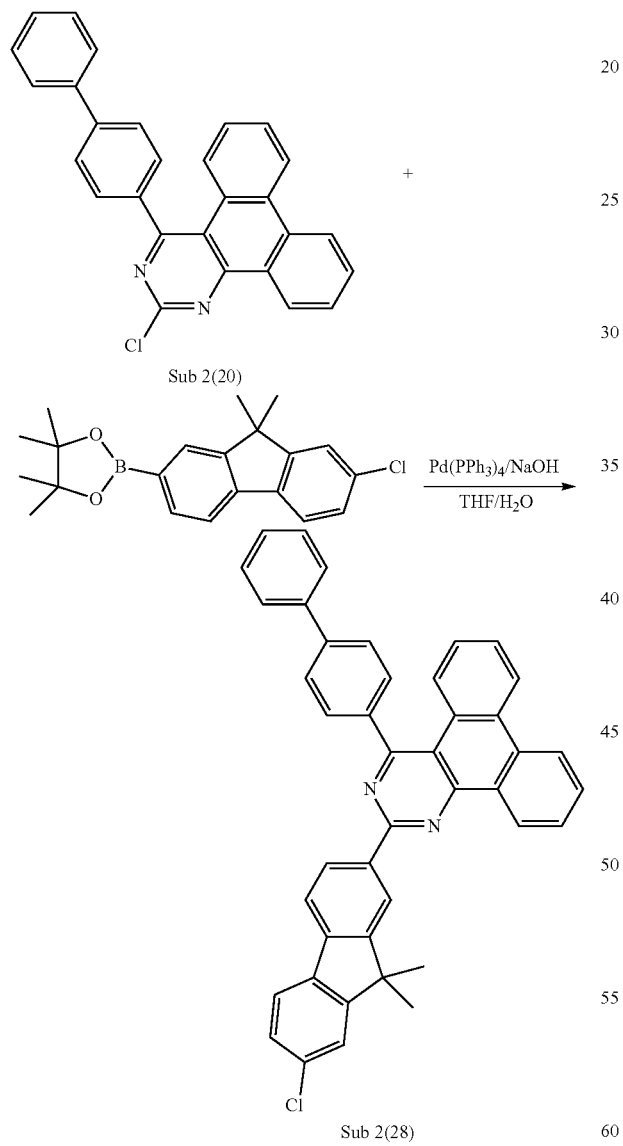

A mixture of Sub 2(20) (33.4 g, 80 mmol), THF 360 mL, 2-(7-chloro-9,9-dimethyl-9H-fluoren-2-yl)-4,4,5,5-tetramethyl-1,3,2-dioxaborolane (29.8 g, 84 mmol), Pd(PPh₃)₄ (2.8 g, 2.4 mmol), NaOH (9.6 g, 240 mmol) and water (180 mL) was refluxed until completion of the reaction. And then, the reaction solution was extracted with ether and water. The organic layer was dried over MgSO₄ and concentrated in vacuo. The crude product was purified by silica gel column chromatography and recrystallization to give Sub 2(28) (38.0 g, 78%).

Examples of Sub 2 compounds include, but are not limited to, the following compounds, and FD-MS data of the compounds are given in Table 2 below.

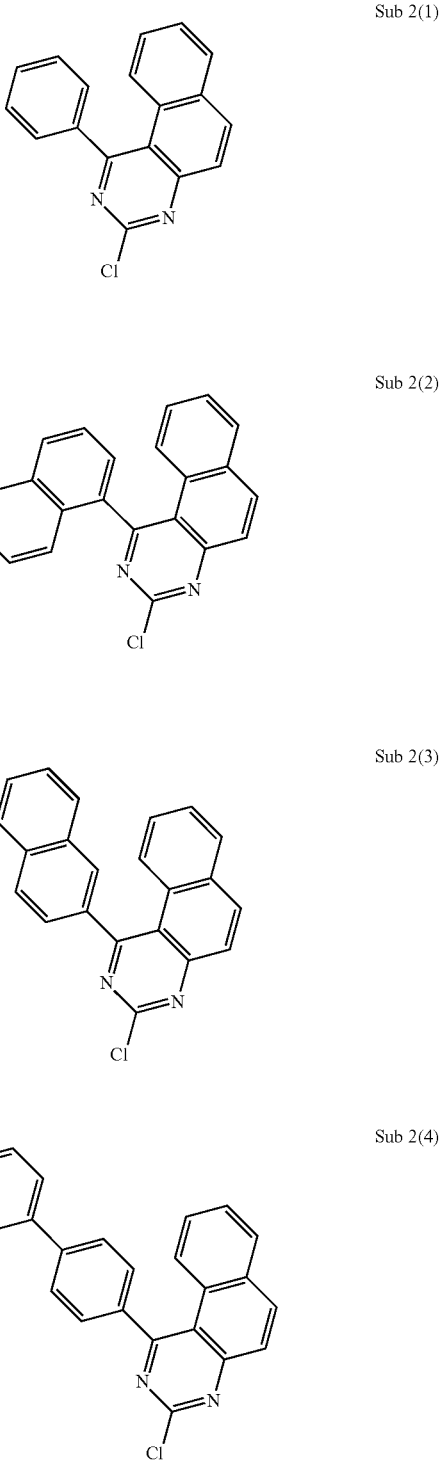

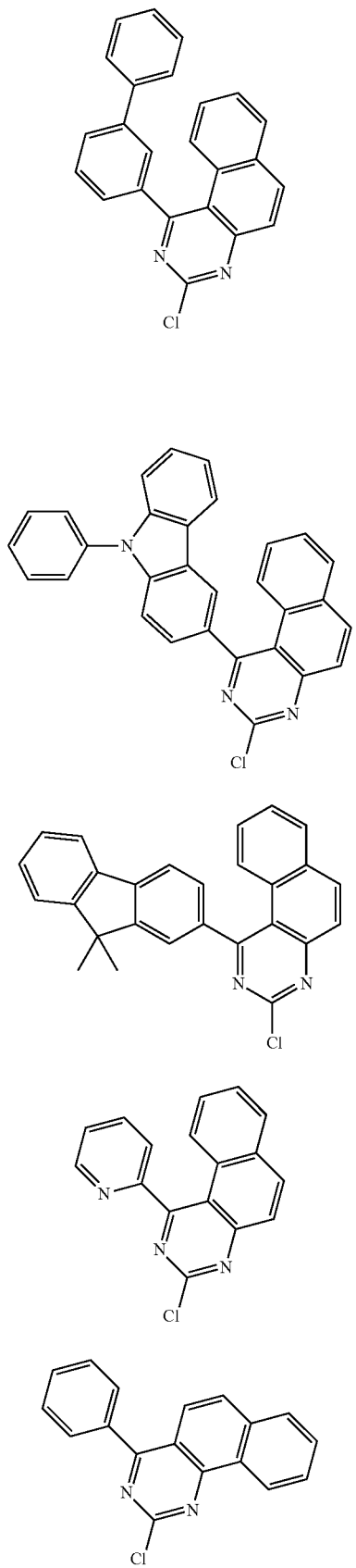
Sub 2(5)
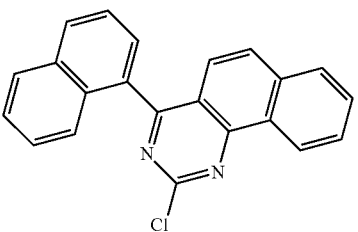
Sub 2(6)
Sub 2(10)
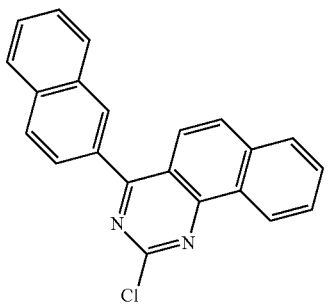
Sub 2(11)
Sub 2(7)
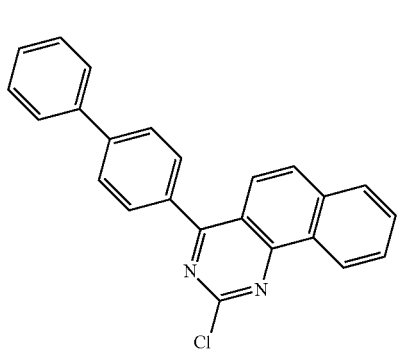
Sub 2(12)
Sub 2(8)
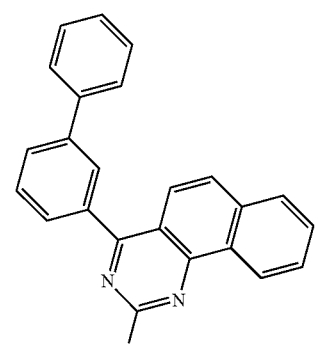
Sub 2(13)
Sub 2(9)
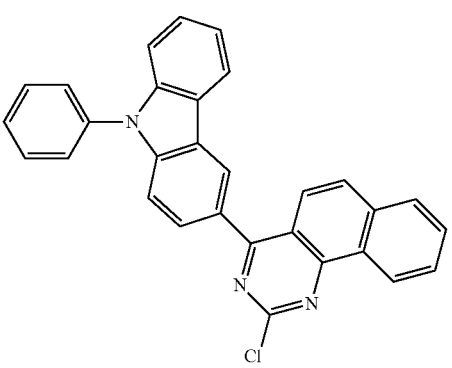
Sub 2(14)

Sub 2(15)
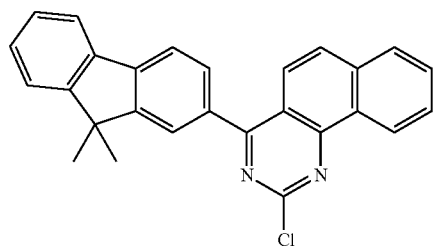
Sub 2(16)
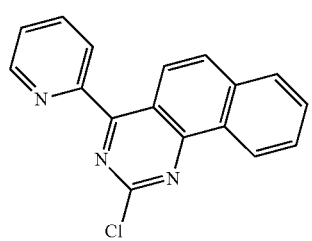
Sub 2(17)
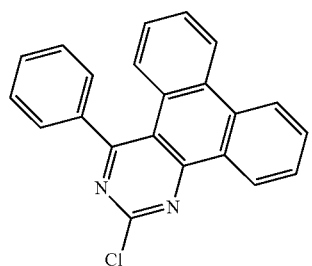
Sub 2(18)
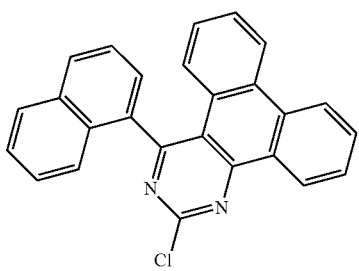
Sub 2(19)
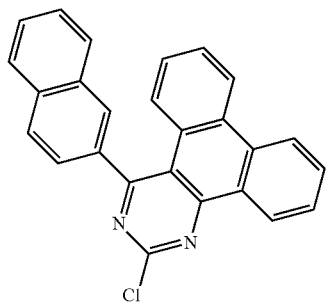
Sub 2(20)
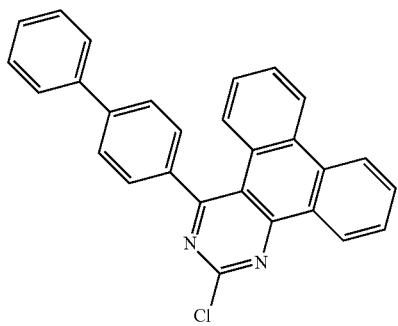
Sub 2(21)
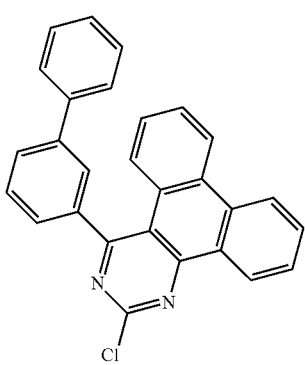
Sub 2(22)
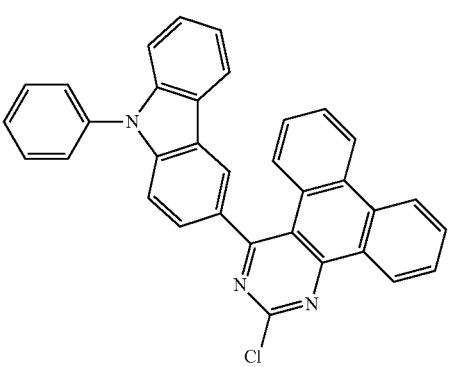
Sub 2(23)
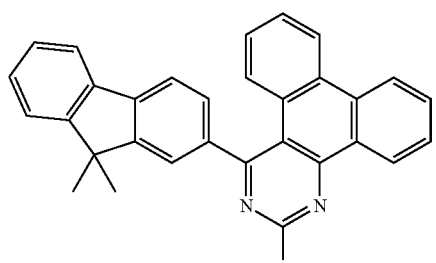
Sub 2(24)
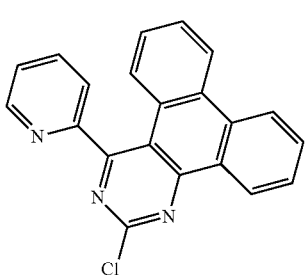

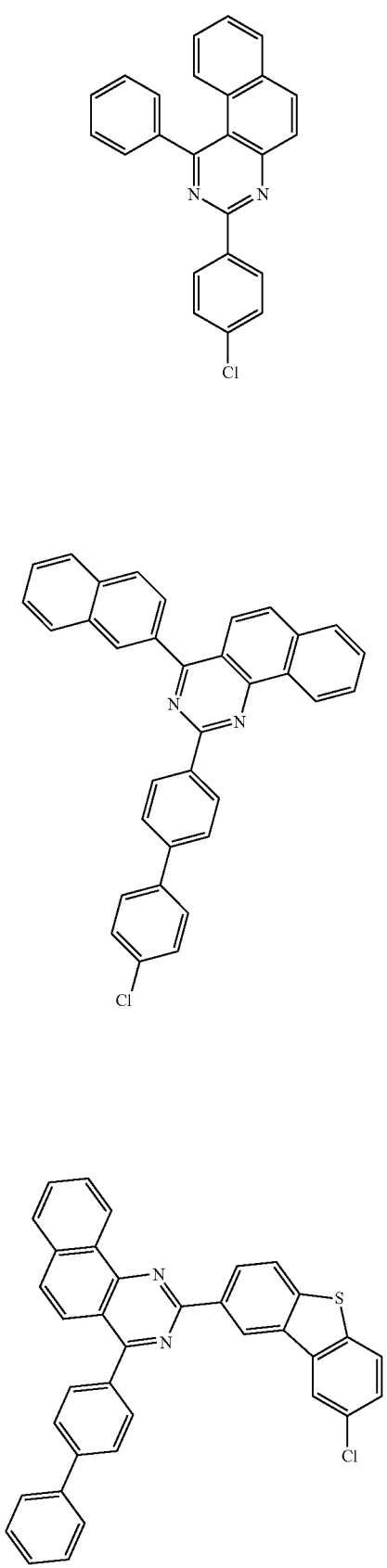

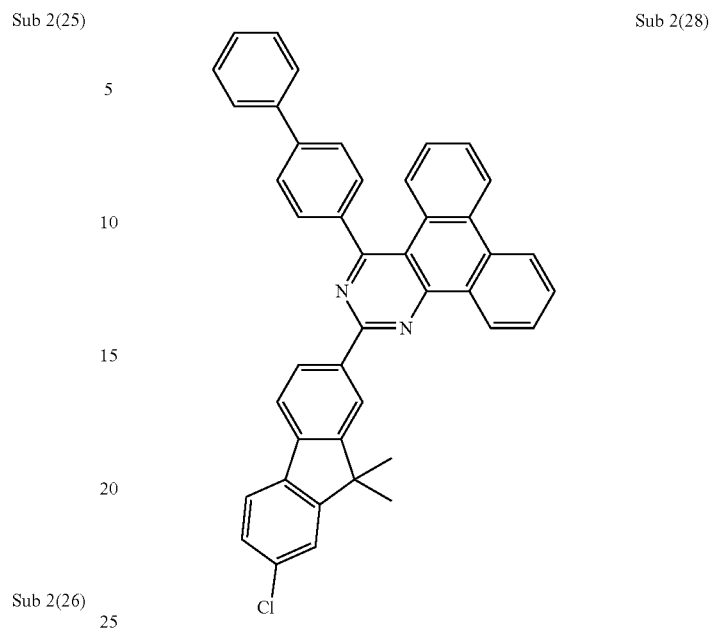

TABLE 2

| Compound | FD-MS |
| --- | --- |
| Sub 2 (1) | m/z = 290.06 ($C_{18}H_{11}ClN_2$ = 290.75) |
| Sub 2 (2) | m/z = 340.08 ($C_{22}H_{13}ClN_2$ = 340.81) |
| Sub 2 (3) | m/z = 340.08 ($C_{22}H_{13}ClN_2$ = 340.81) |
| Sub 2 (4) | m/z = 366.09 ($C_{24}H_{15}ClN_2$ = 366.84) |
| Sub 2 (5) | m/z = 366.09 ($C_{24}H_{15}ClN_2$ = 366.84) |
| Sub 2 (6) | m/z = 455.12 ($C_{30}H_{18}ClN_3$ = 455.94) |
| Sub 2 (7) | m/z = 406.12 ($C_{27}H_{19}ClN_2$ = 406.91) |
| Sub 2 (8) | m/z = 291.06 ($C_{17}H_{10}ClN_3$ = 291.73) |
| Sub 2 (9) | m/z = 290.06 ($C_{18}H_{11}ClN_2$ = 290.75) |
| Sub 2 (10) | m/z = 340.08 ($C_{22}H_{13}ClN_2$ = 340.81) |
| Sub 2 (11) | m/z = 340.08 ($C_{22}H_{13}ClN_2$ = 340.81) |
| Sub 2 (12) | m/z = 366.09 ($C_{24}H_{15}ClN_2$ = 366.84) |
| Sub 2 (13) | m/z = 366.09 ($C_{24}H_{15}ClN_2$ = 366.84) |
| Sub 2 (14) | m/z = 455.12 ($C_{30}H_{18}ClN_3$ = 455.94) |
| Sub 2 (15) | m/z = 406.12 ($C_{27}H_{19}ClN_2$ = 406.91) |
| Sub 2 (16) | m/z = 291.06 ($C_{17}H_{10}ClN_3$ = 291.73) |
| Sub 2 (17) | m/z = 340.08 ($C_{22}H_{13}ClN_2$ = 340.81) |
| Sub 2 (18) | m/z = 390.09 ($C_{26}H_{15}ClN_2$ = 390.86) |
| Sub 2 (19) | m/z = 390.09 ($C_{26}H_{15}ClN_2$ = 390.86) |
| Sub 2 (20) | m/z = 416.11 ($C_{28}H_{17}ClN_2$ = 416.90) |
| Sub 2 (21) | m/z = 416.11 ($C_{28}H_{17}ClN_2$ = 416.90) |
| Sub 2 (22) | m/z = 505.13 ($C_{34}H_{20}ClN_3$ = 506.00) |
| Sub 2 (23) | m/z = 456.14 ($C_{31}H_{21}ClN_2$ = 456.96) |
| Sub 2 (24) | m/z = 341.07 ($C_{21}H_{12}ClN_3$ = 341.79) |
| Sub 2 (25) | m/z = 366.09 ($C_{24}H_{15}ClN_2$ = 366.84) |
| Sub 2 (26) | m/z = 492.14 ($C_{34}H_{21}ClN_2$ = 493.00) |
| Sub 2 (27) | m/z = 548.11 ($C_{36}H_{21}ClN_2S$ = 549.08) |
| Sub 2 (28) | m/z = 608.20 ($C_{43}H_{29}ClN_2$ = 609.16) |

III. Synthesis Method of Final Products

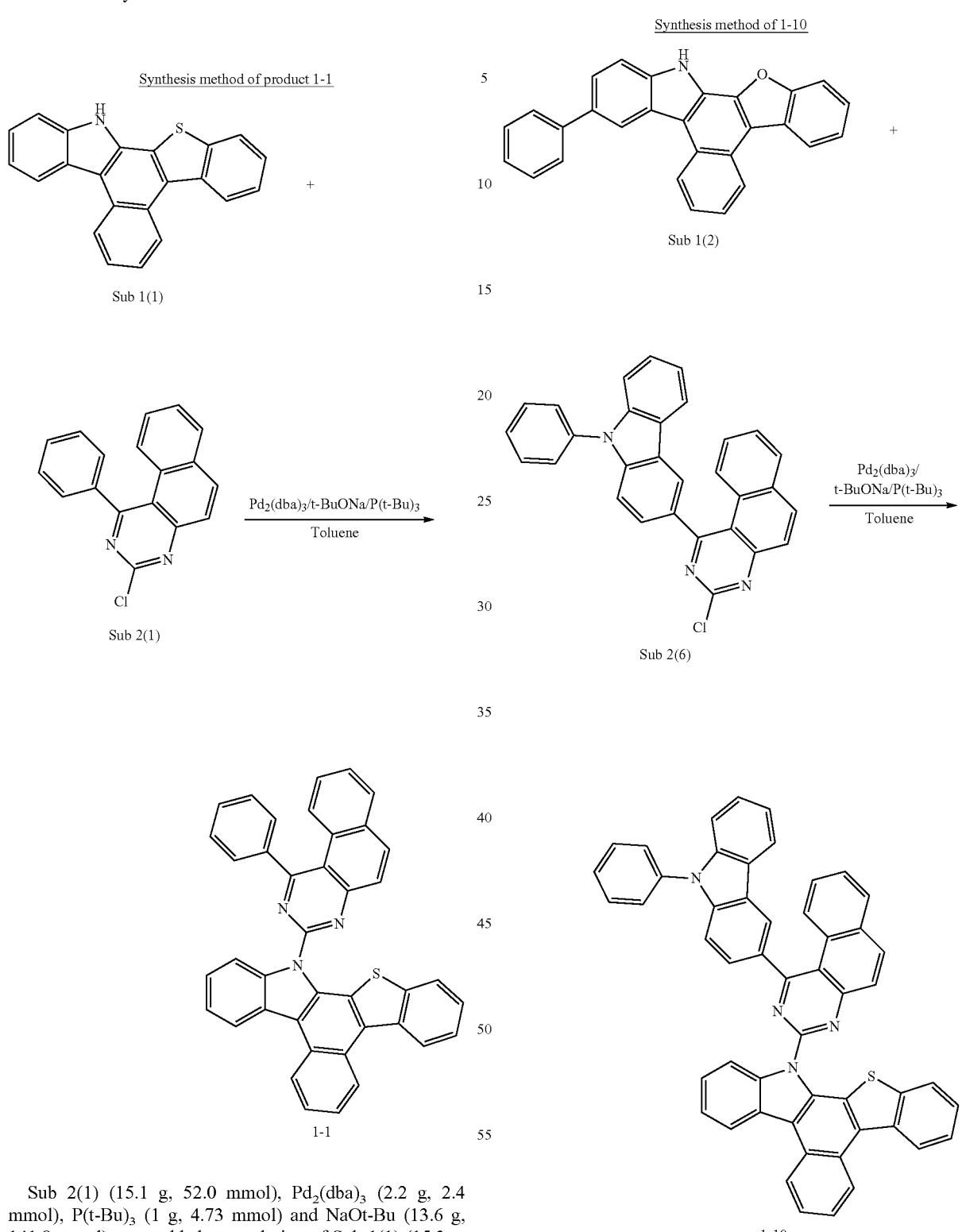

Sub 2(1) (15.1 g, 52.0 mmol), Pd$_2$(dba)$_3$ (2.2 g, 2.4 mmol), P(t-Bu)$_3$ (1 g, 4.73 mmol) and NaOt-Bu (13.6 g, 141.8 mmol) were added to a solution of Sub 1(1) (15.3 g, 47.3 mmol) in 500 mL of toluene and stirred at 100° C. until disappearance of a starting material. The reaction solution was extracted with CH$_2$Cl$_2$ and water and then the organic layer was dried over MgSO$_4$ and concentrated in vacuo. The crude product was purified by silica gel column chromatography and recrystallization to give the product 1-1 (20.8 g, 76%).

27.3 g (72%) of the product 1-10 was prepared from Sub 1(2) (18.1 g, 47.3 mmol) and Sub 2(6) (23.7 g, 52.0 mmol) according to the same way for the product 1-1 above.

Synthesis method of product 1-19
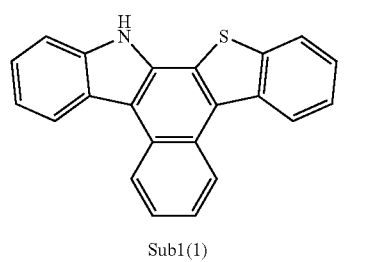
23.8 g (77%) of the product 1-19 was prepared from Sub 1(1) (15.3 g, 47.3 mmol) and Sub 2(4) (19.1 g, 52.0 mmol) according to the same way for the product 1-1 above.
Synthesis method of product 2-1
21.3 g (78%) of the product 2-1 was prepared from Sub 1(2) (15.3 g, 47.3 mmol) and Sub 2(9) (15.2 g, 52.0 mmol) according to the same way for the product 1-1 above.
Synthesis method of product 2-8
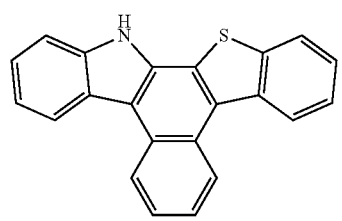

-continued

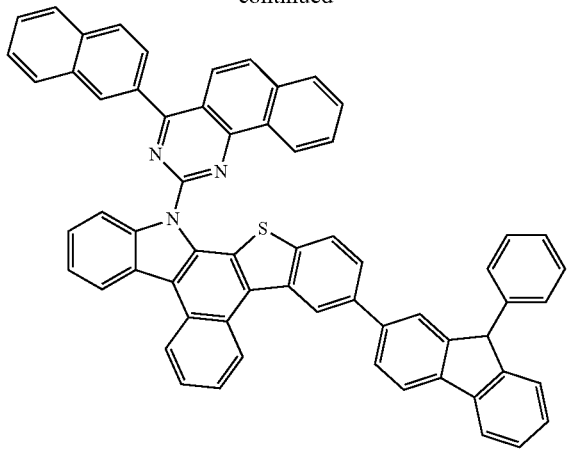

30.4 g (74%) of the product 2-8 was prepared from Sub 1(8) (26.7 g, 47.3 mmol) and Sub 2(11) (17.7 g, 52.0 mmol) according to the same way for the product 1-1 above.

Synthesis method of product 2-13

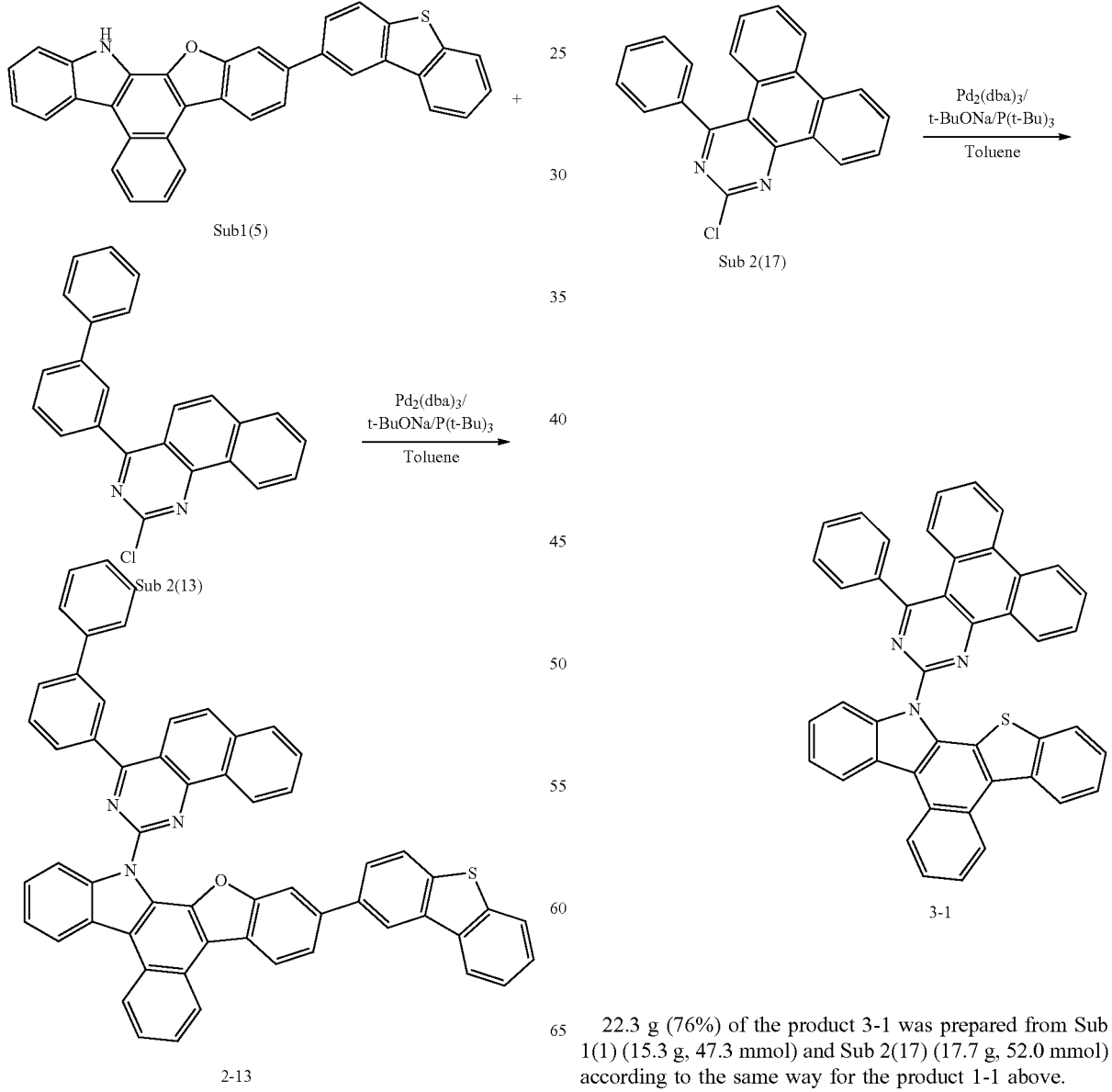

2-13

27.9 g (72%) of the product 2-13 was prepared from Sub 1(5) (23.2 g, 47.3 mmol) and Sub 2(13) (19.1 g, 52.0 mmol) according to the same way for the product 1-1 above.

Synthesis method of product 3-1

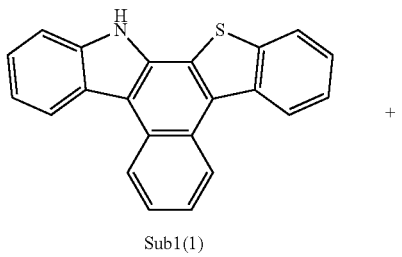

Sub1(1)

3-1

22.3 g (76%) of the product 3-1 was prepared from Sub 1(1) (15.3 g, 47.3 mmol) and Sub 2(17) (17.7 g, 52.0 mmol) according to the same way for the product 1-1 above.

Synthesis method of product 3-15

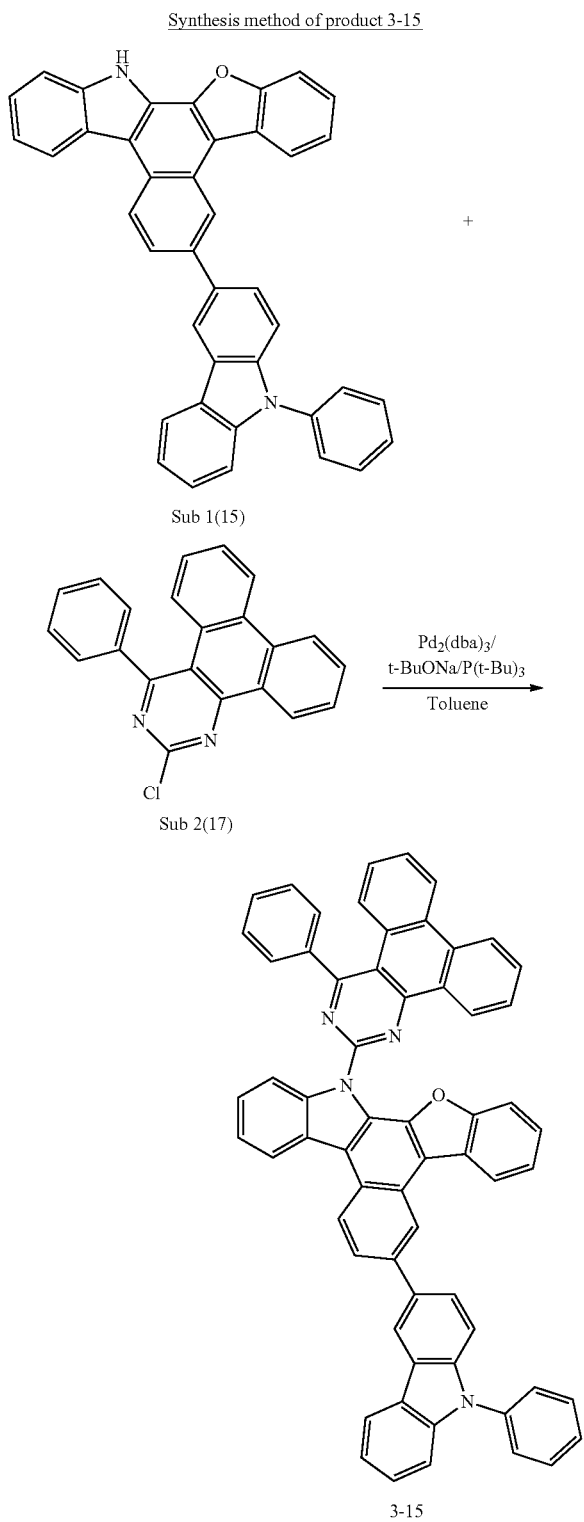

28.6 g (71%) of the product 3-15 was prepared from Sub 1(15) (26.0 g, 47.3 mmol) and Sub 2(17) (17.7 g, 52.0 mmol) according to the same way for the product 1-1 above.

FD-MS data of the compound 1-1 to 3-20 prepared in the Synthesis Examples of the present invention are given in Table 3 below.

TABLE 3

| Compound | FD-MS |
|---|---|
| 1-1 | m/z = 577.16 ($C_{40}H_{23}N_3S$ = 577.70) |
| 1-2 | m/z = 653.19 ($C_{46}H_{27}N_3S$ = 653.79) |
| 1-3 | m/z = 818.25 ($C_{52}H_{34}N_4S$ = 818.98) |
| 1-4 | m/z = 654.19 ($C_{45}H_{26}N_4S$ = 654.78) |
| 1-5 | m/z = 809.20 ($C_{56}H_{31}N_3S_2$ = 810.00) |
| 1-6 | m/z = 779.24 ($C_{56}H_{33}N_3S$ = 779.95) |
| 1-7 | m/z = 858.26 ($C_{59}H_{34}N_6S$ = 859.01) |
| 1-8 | m/z = 868.27 ($C_{62}H_{36}N_4S$ = 869.04) |
| 1-9 | m/z = 561.18 ($C_{40}H_{23}N_3O$ = 561.63) |
| 1-10 | m/z = 802.27 ($C_{58}H_{34}N_4O$ = 802.92) |
| 1-11 | m/z = 918.34 ($C_{67}H_{42}N_4O$ = 919.08) |
| 1-12 | m/z = 639.21 ($C_{44}H_{25}N_5O$ = 639.70) |
| 1-13 | m/z = 819.23 ($C_{58}H_{33}N_3OS$ = 819.97) |
| 1-14 | m/z = 763.26 ($C_{56}H_{33}N_3O$ = 763.88) |
| 1-15 | m/z = 802.27 ($C_{58}H_{34}N_4O$ = 802.92) |
| 1-16 | m/z = 852.29 ($C_{62}H_{36}N_4O$ = 852.98) |
| 1-17 | m/z = 627.18 ($C_{44}H_{25}N_3S$ = 627.75) |
| 1-18 | m/z = 627.18 ($C_{44}H_{25}N_3S$ = 627.75) |
| 1-19 | m/z = 658.19 ($C_{46}H_{27}N_3S$ = 653.79) |
| 1-20 | m/z = 693.22 ($C_{49}H_{31}N_3S$ = 693.86) |
| 2-1 | m/z = 577.16 ($C_{40}H_{23}N_3S$ = 577.70) |
| 2-2 | m/z = 653.19 ($C_{46}H_{27}N_3S$ = 653.79) |
| 2-3 | m/z = 818.25 ($C_{52}H_{34}N_4S$ = 818.98) |
| 2-4 | m/z = 654.19 ($C_{45}H_{26}N_4S$ = 654.78) |
| 2-5 | m/z = 809.20 ($C_{56}H_{31}N_3S_2$ = 810.00) |
| 2-6 | m/z = 779.24 ($C_{56}H_{33}N_3S$ = 779.95) |
| 2-7 | m/z = 858.26 ($C_{59}H_{34}N_6S$ = 859.01) |
| 2-8 | m/z = 868.27 ($C_{62}H_{36}N_4S$ = 869.04) |
| 2-9 | m/z = 561.18 ($C_{40}H_{23}N_3O$ = 561.63) |
| 2-10 | m/z = 802.27 ($C_{58}H_{34}N_4O$ = 802.92) |
| 2-11 | m/z = 918.34 ($C_{67}H_{42}N_4O$ = 919.08) |
| 2-12 | m/z = 639.21 ($C_{44}H_{25}N_5O$ = 639.70) |
| 2-13 | m/z = 819.23 ($C_{58}H_{33}N_3OS$ = 819.97) |
| 2-14 | m/z = 763.26 ($C_{56}H_{33}N_3O$ = 763.88) |
| 2-15 | m/z = 802.27 ($C_{58}H_{34}N_4O$ = 802.92) |
| 2-16 | m/z = 852.29 ($C_{62}H_{36}N_4O$ = 852.98) |
| 2-17 | m/z = 627.18 ($C_{44}H_{25}N_3S$ = 627.75) |
| 2-18 | m/z = 627.18 ($C_{44}H_{25}N_3S$ = 627.75) |
| 2-19 | m/z = 658.19 ($C_{46}H_{27}N_3S$ = 653.79) |
| 2-20 | m/z = 693.22 ($C_{49}H_{31}N_3S$ = 693.86) |
| 3-1 | m/z = 627.18 ($C_{44}H_{25}N_3S$ = 627.75) |
| 3-2 | m/z = 703.21 ($C_{50}H_{29}N_3S$ = 703.85) |
| 3-3 | m/z = 859.21 ($C_{60}H_{33}N_3S_2$ = 860.05) |
| 3-4 | m/z = 704.20 ($C_{49}H_{28}N_4S$ = 704.84) |
| 3-5 | m/z = 859.21 $C_{60}H_{33}N_3S_2$ = 860.05) |
| 3-6 | m/z = 829.26 ($C_{60}H_{35}N_3S$ = 830.01) |
| 3-7 | m/z = 908.27 ($C_{63}H_{36}N_6S$ = 909.07) |
| 3-8 | m/z = 918.28 ($C_{66}H_{38}N_4S$ = 919.10) |
| 3-9 | m/z = 611.20 ($C_{44}H_{25}N_3O$ = 611.69) |
| 3-10 | m/z = 852.29 ($C_{62}H_{36}N_4O$ = 852.98) |
| 3-11 | m/z = 968.35 ($C_{71}H_{44}N_4O$ = 969.14) |
| 3-12 | m/z = 689.22 ($C_{48}H_{27}N_5O$ = 689.76) |
| 3-13 | m/z = 869.25 ($C_{62}H_{35}N_3OS$ = 870.03) |
| 3-14 | m/z = 813.28 ($C_{60}H_{35}N_3O$ = 813.94) |
| 3-15 | m/z = 852.29 ($C_{62}H_{36}N_4O$ = 852.98) |
| 3-16 | m/z = 902.30 ($C_{66}H_{38}N_4O$ = 903.03) |
| 3-17 | m/z = 677.19 ($C_{48}H_{27}N_3S$ = 677.81) |
| 3-18 | m/z = 677.19 ($C_{48}H_{27}N_3S$ = 677.81) |
| 3-19 | m/z = 703.21 ($C_{50}H_{29}N_3S$ = 703.85) |
| 3-20 | m/z = 743.24 ($C_{53}H_{33}N_3S$ = 743.91) |

Fabrication and Evaluation of Organic Electric Element

Test Example 1

Red Organic Light Emitting Diode

An ITO layer (anode) was formed on a glass substrate, and a film of 4,4',4"-tris[2-naphthyl(phenyl)amino]triphenylamine (hereinafter abbreviated as "2-TNATA") was vacuum-deposited on the ITO layer to form a hole injection layer with a thickness of 60 nm. Subsequently, N,N'-bis(1-naphthalenyl)-N,N'-bis-phenyl-(1,1'-biphenyl)-4,4'-diamine (hereinafter abbreviated as "NPB") was vacuum-deposited on the hole injection layer to form a hole transfer layer with a thickness of 60 nm. Continually, a light emitting layer with a thickness of 30 nm was deposited on the hole transfer layer by doping the hole transfer layer with the inventive compound 1-1 as a host material and bis(1-phenylisoquinoline)iridium(III)acetylacetonate (hereinafter abbreviated as (piq)$_2$Ir(acac)) as a dopant material in a weight ratio of 95:5. Next, ((1,1'-biphenyl)-4-olato)bis(2-methyl-8-quinolinolato)aluminum (hereinafter abbreviated as "BAlq") was vacuum-deposited with a thickness of 10 nm on the light emitting layer to form a hole blocking layer, a film of tris-(8-hydroxyquinoline)aluminum (hereinafter abbreviated as "Alq$_3$") was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, Organic electron emitting diode was completed.

Example 2 to Example 24

Red Organic Light Emitting Diod

The OLEDs were manufactured in the same manner as described in Example 1, except that any one of the compounds 1-3 to 3-20 of the present invention in the Table 4 below was used as the host material of the light emitting layer, instead of the inventive compound 1-1.

Comparative Example 1 to Comparative Example 3

OLEDs were manufactured in the same manner as described in Example 1, except that comparative compounds A to C represented below were used as the host material of the light emitting layer, instead of the inventive compound 1-1.

[comp. Com. A]

[comp. Com. B]

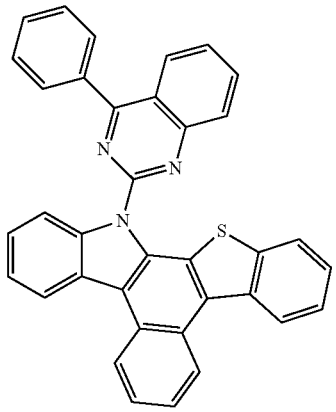

[comp. Com. C]

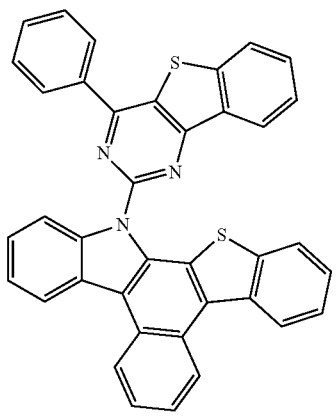

A forward bias DC voltage was applied to each of the OLEDs manufactured through the Examples 1 to 24 and Comparative Example 1 to 3, and electro-luminescence (EL) characteristics of the OLED were measured by PR-650 (Photo research). Also, T95 life span was measured by life span measuring equipment (Mc science) at reference brightness of 2500 cd/m$^2$. Table 4 below shows evaluation results.

TABLE 4

| | Compound | Voltage (V) | Current Density (mA/cm$^2$) | Brightness (cd/m$^2$) | Efficiency (cd/A) | Lifetime T(90) | CIE (x, y) |
|---|---|---|---|---|---|---|---|
| comp. Ex. (1) | comp. Com. A | 6.7 | 34.2 | 2500.0 | 7.3 | 75.6 | (0.66, 0.32) |
| comp. Ex. (2) | comp. Com. B | 6.0 | 23.8 | 2500.0 | 10.5 | 143.6 | (0.67, 0.32) |
| comp. Ex. (3) | comp. Com. C | 5.9 | 18.0 | 2500.0 | 13.9 | 135.2 | (0.66, 0.32) |
| Ex. (1) | Com. (1-1) | 5.8 | 10.5 | 2500.0 | 23.9 | 140.5 | (0.66, 0.35) |
| Ex. (2) | Com. (1-3) | 5.7 | 10.8 | 2500.0 | 23.1 | 140.5 | (0.66, 0.35) |
| Ex. (3) | Com. (1-9) | 5.7 | 10.9 | 2500.0 | 23.0 | 140.2 | (0.66, 0.35) |
| Ex. (4) | Com. (1-14) | 5.8 | 11.2 | 2500.0 | 22.3 | 140.1 | (0.66, 0.35) |
| Ex. (5) | Com. (1-17) | 5.9 | 10.5 | 2500.0 | 23.9 | 140.7 | (0.66, 0.35) |
| Ex. (6) | Com. (1-18) | 5.8 | 10.4 | 2500.0 | 24.0 | 140.1 | (0.66, 0.35) |
| Ex. (7) | Com. (1-19) | 5.9 | 10.6 | 2500.0 | 23.7 | 140.7 | (0.66, 0.35) |
| Ex. (8) | Com. (1-20) | 5.7 | 10.6 | 2500.0 | 23.5 | 140.4 | (0.66, 0.35) |
| Ex. (9) | Com. (2-1) | 5.8 | 8.9 | 2500.0 | 28.0 | 141.0 | (0.66, 0.35) |
| Ex. (10) | Com. (2-2) | 5.9 | 9.2 | 2500.0 | 27.1 | 141.1 | (0.66, 0.35) |
| Ex. (11) | Com. (2-9) | 5.8 | 9.3 | 2500.0 | 26.8 | 141.0 | (0.66, 0.35) |

TABLE 4-continued

| | Compound | Voltage (V) | Current Density (mA/cm$^2$) | Brightness (cd/m$^2$) | Efficiency (cd/A) | Lifetime T(90) | CIE (x, y) |
|---|---|---|---|---|---|---|---|
| Ex. (12) | Com. (2-11) | 5.8 | 9.5 | 2500.0 | 26.3 | 141.7 | (0.66, 0.35) |
| Ex. (13) | Com. (2-17) | 5.8 | 9.0 | 2500.0 | 27.9 | 141.6 | (0.66, 0.35) |
| Ex. (14) | Com. (2-18) | 5.7 | 9.1 | 2500.0 | 27.5 | 141.9 | (0.66, 0.35) |
| Ex. (15) | Com. (2-19) | 5.8 | 9.0 | 2500.0 | 27.8 | 141.3 | (0.66, 0.35) |
| Ex. (16) | Com. (2-20) | 5.7 | 9.0 | 2500.0 | 27.7 | 141.5 | (0.66, 0.35) |
| Ex. (17) | Com. (3-1) | 5.8 | 11.7 | 2500.0 | 21.4 | 138.5 | (0.66, 0.35) |
| Ex. (18) | Com. (3-6) | 5.9 | 11.9 | 2500.0 | 21.0 | 138.7 | (0.66, 0.35) |
| Ex. (19) | Com. (3-9) | 5.8 | 12.0 | 2500.0 | 20.9 | 138.1 | (0.66, 0.35) |
| Ex. (20) | Com. (3-13) | 5.8 | 12.4 | 2500.0 | 20.1 | 138.6 | (0.66, 0.35) |
| Ex. (21) | Com. (3-17) | 5.8 | 11.5 | 2500.0 | 21.6 | 138.3 | (0.66, 0.35) |
| Ex. (22) | Com. (3-18) | 5.8 | 11.7 | 2500.0 | 21.4 | 138.2 | (0.66, 0.35) |
| Ex. (23) | Com. (3-19) | 5.9 | 11.6 | 2500.0 | 21.6 | 138.4 | (0.66, 0.35) |
| Ex. (24) | Com. (3-20) | 5.8 | 11.5 | 2500.0 | 21.8 | 138.7 | (0.66, 0.35) |

As shown in Table 4 above, in the cases where the materials of the present invention were used as a phosphorescent host for the OLEDs, a reduced driving voltage with a significantly improved luminous efficiency and a lifespan was obtained.

Specifically, the OLEDs using the compounds of the present invention, or Comparative Compounds B and C having the same core with the present invention, as a phosphorescent host material, found to have a significantly reduced driving voltage with a significantly improved luminous efficiency and lifespan, compared to those using Comparative Compound A, a conventionally used phosphorescent host material.

In addition, from the comparison of Examples of the present invention and Comparative Examples 2 and 3, it was shown that even with the same core the element properties varies depending on the substituent bonded to the N atom of the core. That is, the compounds of the present invention substituted with benzoquinazoline or dibenzoquinazoline had a significantly improved luminous efficiency, compared to Comparative Compound B substituted with quinazoline and Comparative Compound C substituted with benzotienopyrimidine.

Without being bound by any particular theory of operation, it is believed that the compounds substituted with benzoquinazoline or dibenzoquinazoline changes the energy level of the compounds, and as the result, the energy balance are improved and the luminous efficiency are improved in the light emitting layer.

Accordingly, it was shown that even with the same core, the chemical properties of the compounds like the energy level and the element properties of the compounds like the packing density depend on the substituent bonded to the core, and the OLED properties depend on the chemical properties and the element properties.

Although the exemplary embodiments of the present invention have been described above for illustrative purposes, those skilled in the art will appreciate that various modifications, additions and substitutions are possible, without departing from the scope and spirit of the invention as disclosed in the accompanying claims. Therefore, the embodiment disclosed herein is intended to illustrate the scope of the technical idea of the present invention, and the scope of the present invention is not limited by the embodiments. The scope of the present invention shall be construed on the basis of the accompanying claims, and it shall be construed that all of the technical ideas included within the scope equivalent to the claims belong to the present invention.

The invention claimed is:
1. A compound of Formula 1:

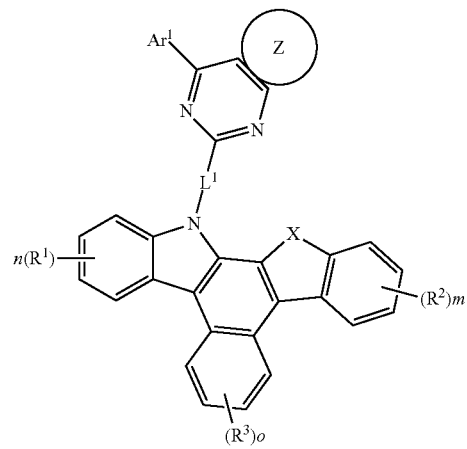

[Formula 1]

wherein,
Z ring is a $C_{10}$-$C_{20}$ aryl group,
X is O,
$L^1$ is selected from the group consisting of a single bond, a $C_6$-$C_{60}$ arylene group, a fluorenylene group, a $C_2$-$C_{60}$ heteroarylene group containing at least one heteroatom selected from the group consisting of O, N, S, Si, and P, and a fused ring group of a $C_3$-$C_{60}$ aliphatic ring and a $C_6$-$C_{60}$ aromatic ring,
$Ar^1$ is a $C_6$-$C_{60}$ aryl group, a $C_2$-$C_{60}$ heterocyclic group containing at least one heteroatom selected from the group consisting of O, N, S, Si, and P, a fluorenyl group, or a fused ring group of a $C_3$-$C_{60}$ aliphatic ring and a $C_6$-$C_{60}$ aromatic ring,
m, n and o are each an integer of 0 to 4,
$R^1$, $R^2$ and $R^3$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si, and P, a fused ring group of a $C_3$-$C_{60}$ aliphatic ring and a $C_6$-$C_{60}$ aromatic ring, a $C_1$-$C_{50}$ alkyl group, a $C_2$-$C_{20}$ alkenyl group, a $C_2$-$C_{20}$ alkynyl group, a $C_1$-$C_{30}$ alkoxy group, a $C_6$-$C_{30}$ aryloxy group, and -L'-N($R_a$)($R_b$), and at least on of adjacent $R^1$s or $R^2$s and $R^3$s may optionally form a ring, L' is selected from the group consisting of a single bond, a $C_6$-$C_{60}$ arylene group, a fluorenylene group, a fused ring group of a $C_3$-$C_{60}$ aliphatic ring or a $C_6$-$C_{60}$ aromatic ring, and a $C_2$-$C_{60}$ heterocyclic group containing at least one heteroatom selected from O, N, S, Si, and P, $R_a$ and $R_b$ are each independently selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, and a $C_2$-$C_{60}$ heterocyclic group containing at least one heteroatom selected from O, N, S, Si, and P, and with the proviso that, the aryl group, heterocyclic group, fluorenyl group, fused ring group, alkyl group, alkenyl group, alkynyl group, alkoxy group, aryloxy group, arylene group, and fluorenylene group are optionally substituted by one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, and a $C_8$-$C_{20}$ arylalkenyl group.

2. The compound of claim 1, wherein Formula 1 is represented by Formula 2, Formula 3, or Formula 4:

[Formula 2]

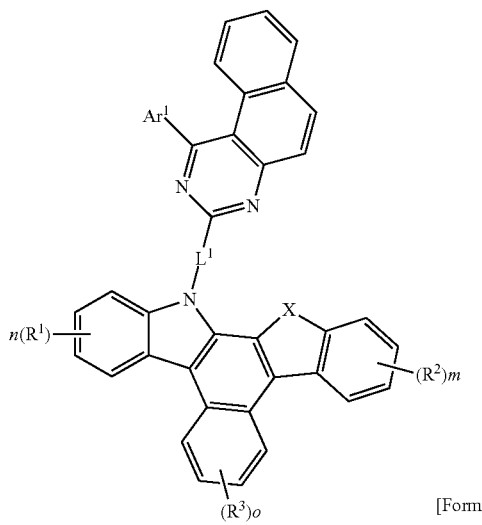

[Formula 3]

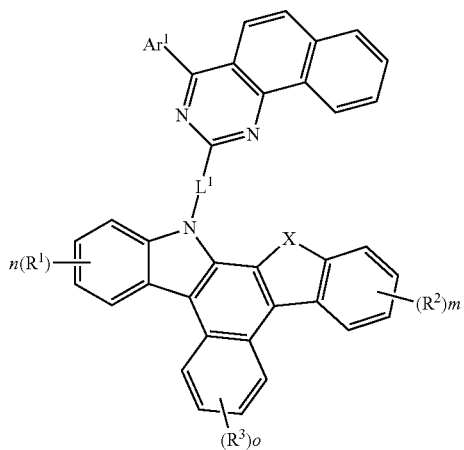

[Formula 4]

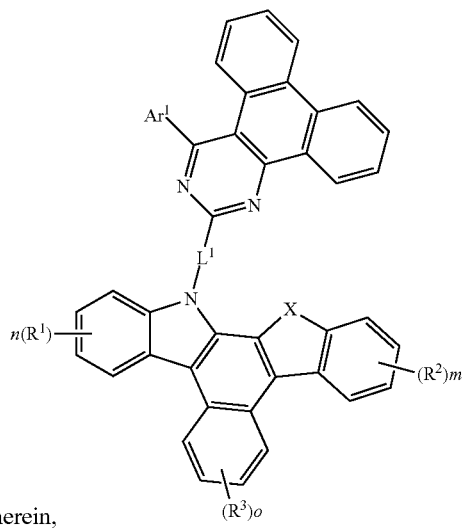

wherein, $Ar^1$, $L^1$, $R^1$ to $R^3$, m, n, o and X are the same as defined in claim 1.

3. The compound of claim 1, wherein Z ring is a naphthyl or phenanthrenyl group.

4. The compound of claim 1, wherein Formula 1 is any one of the compounds below:

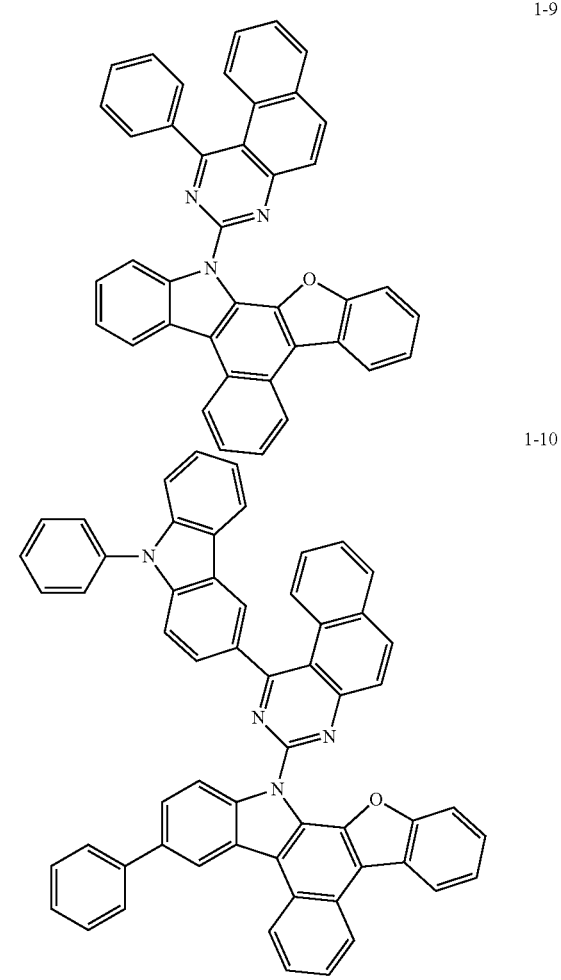

1-9

1-10

-continued
1-11
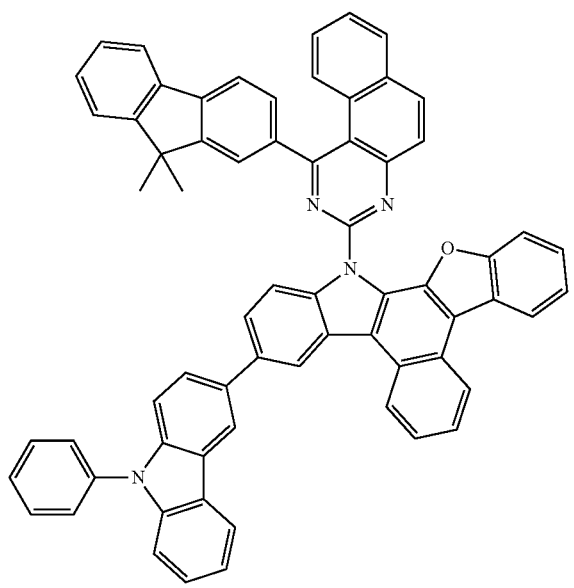
1-12
1-14
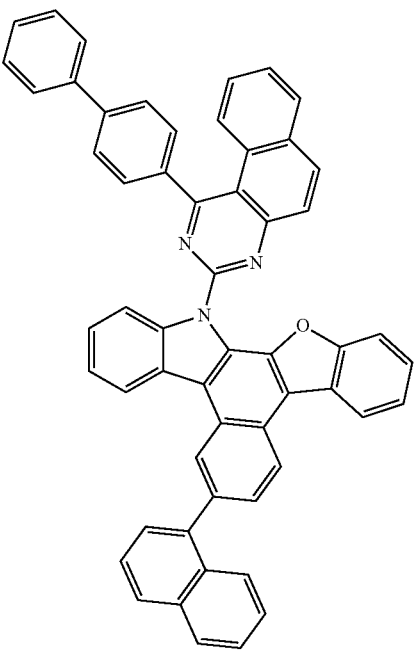
1-13
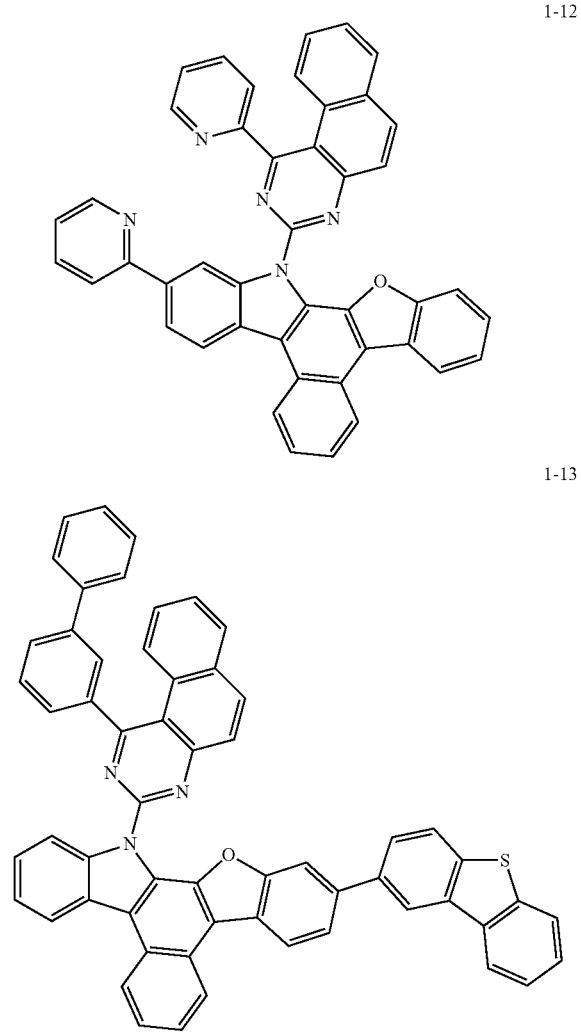
1-15

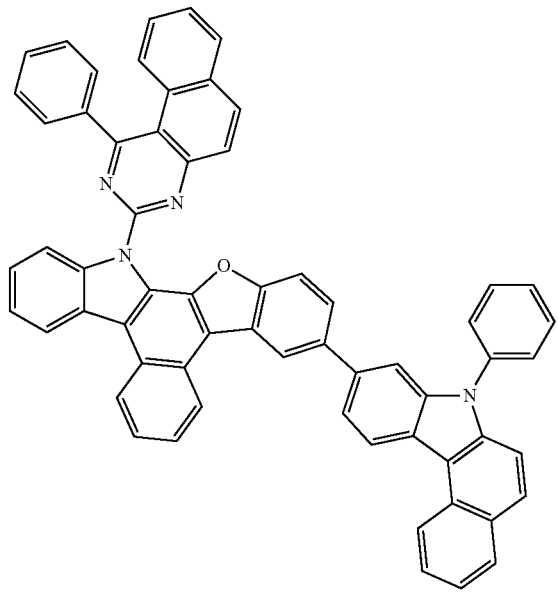
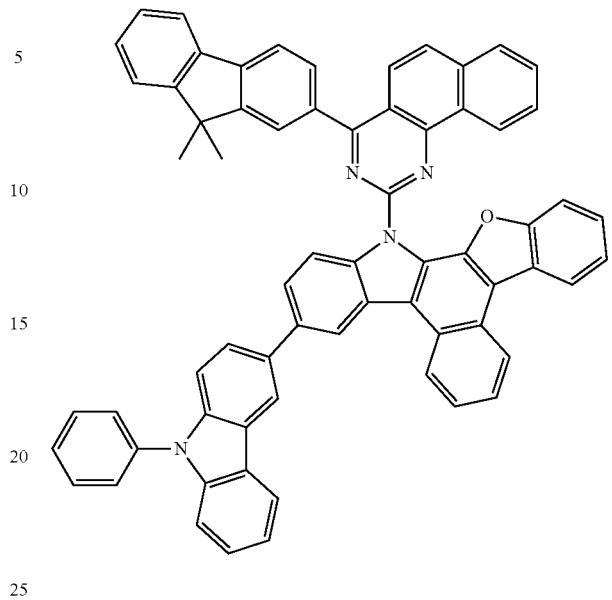
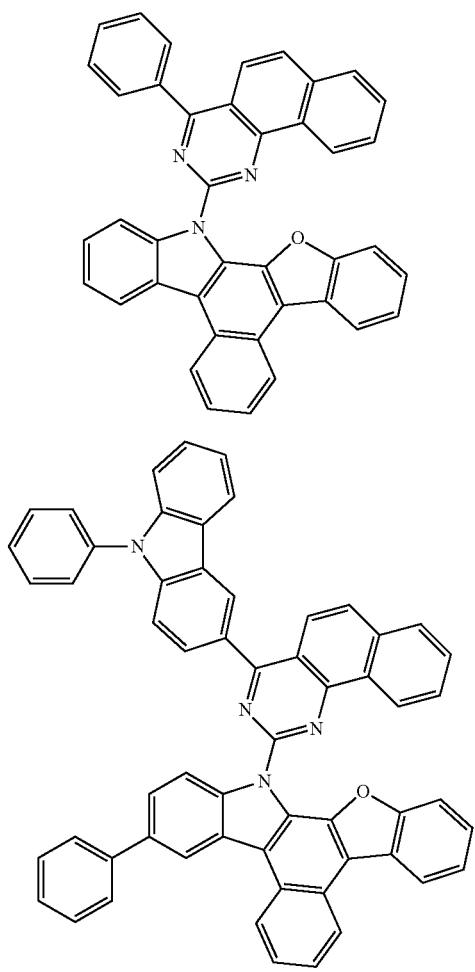
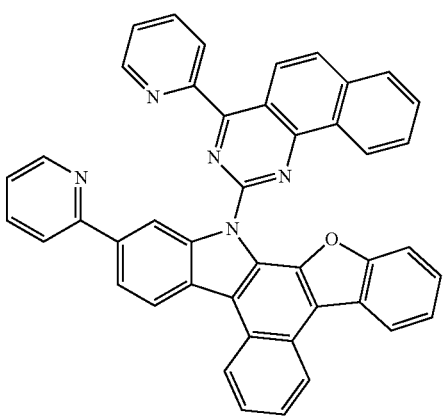
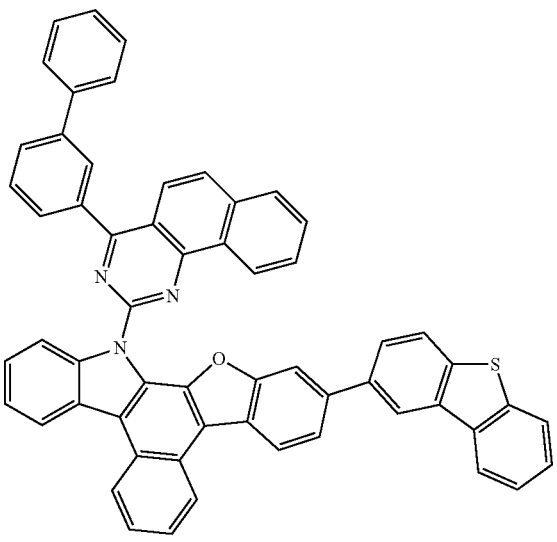

2-14
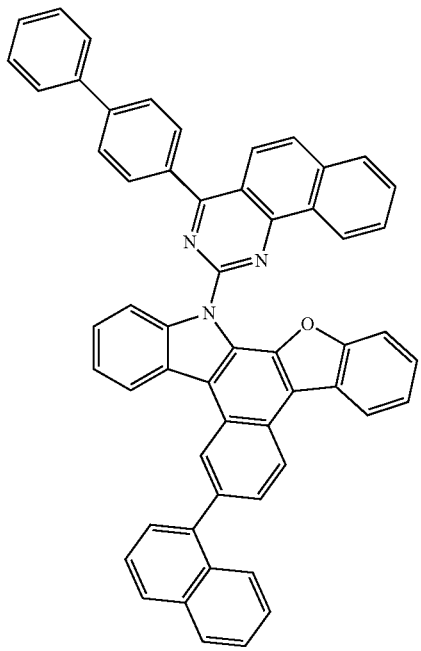
2-15
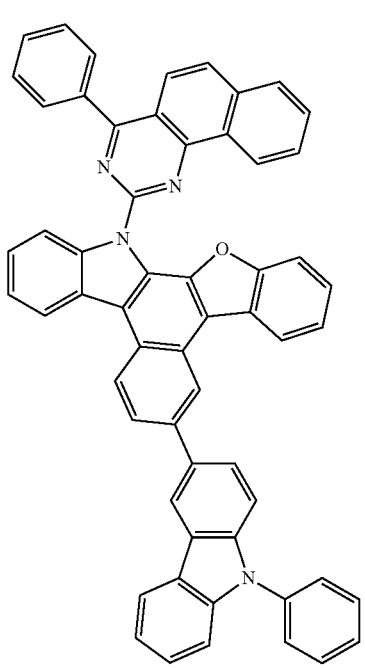
2-16
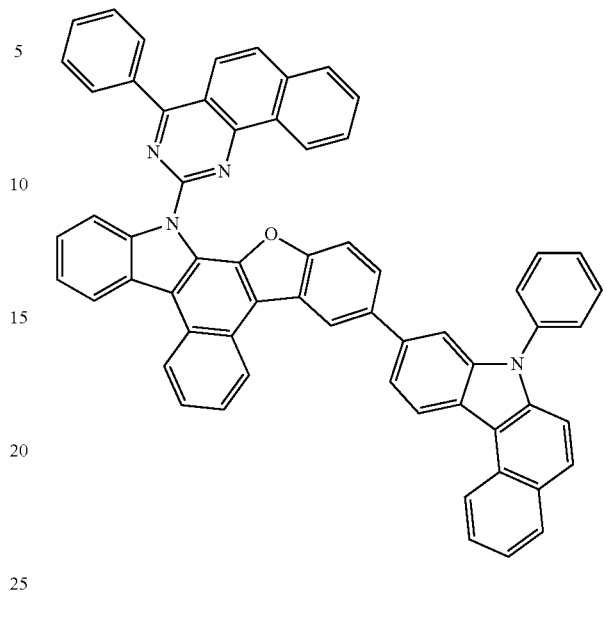
3-9
3-10
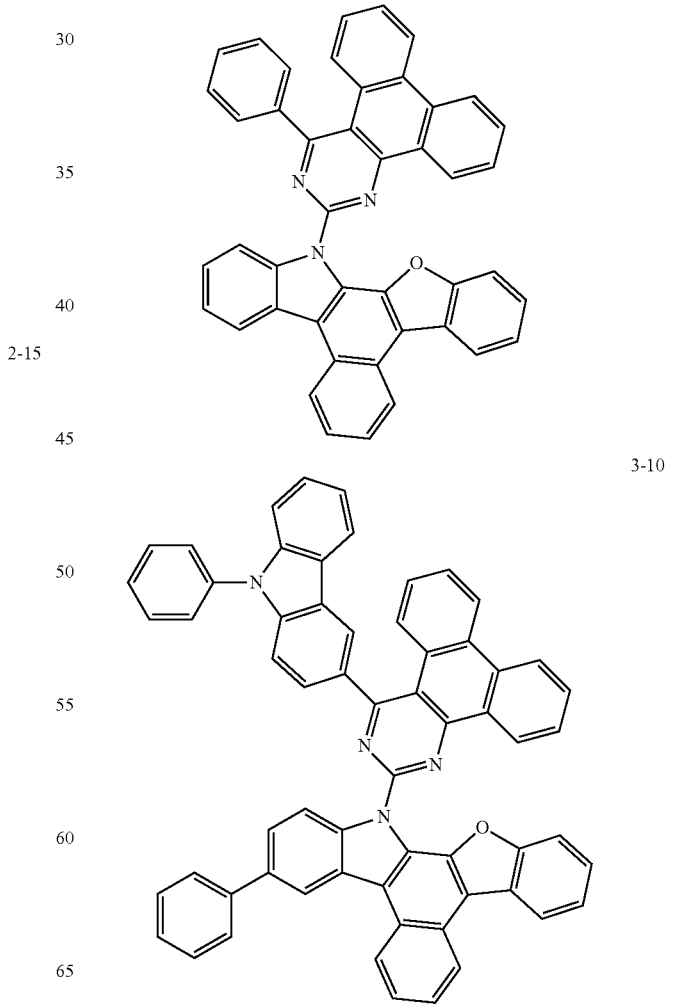

-continued
3-11
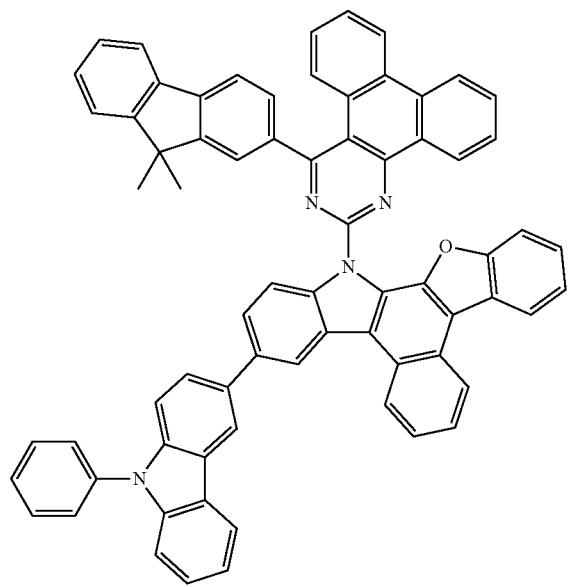
3-12
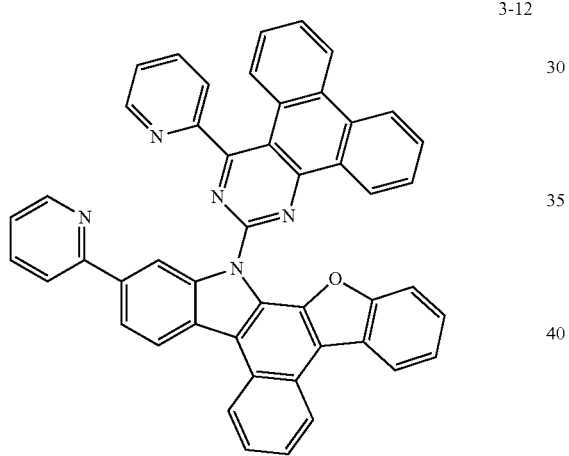
3-13
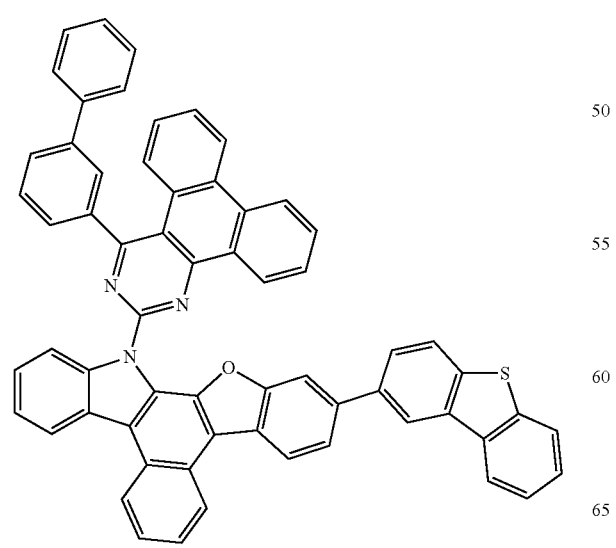
-continued
3-14
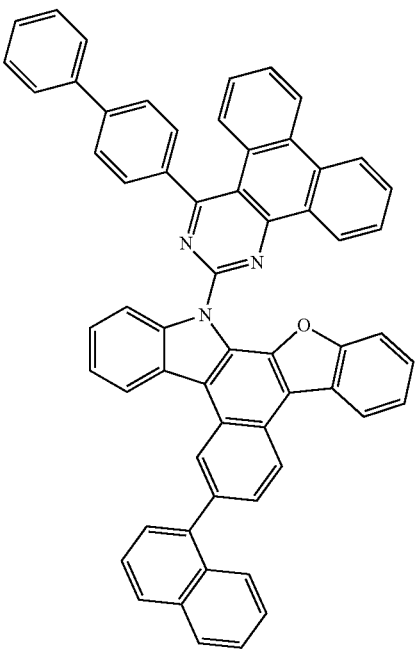
3-15
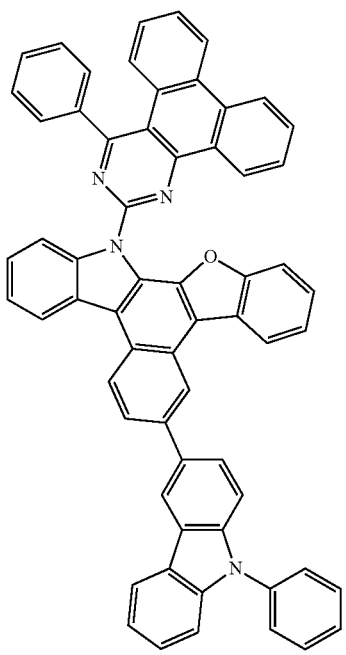

-continued 3-16

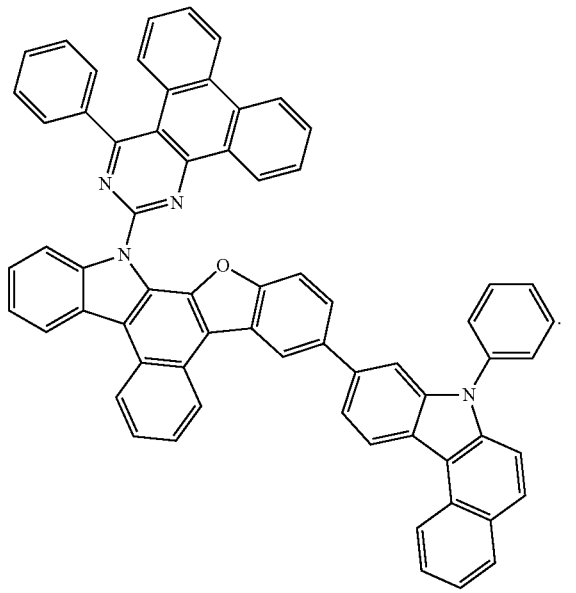

5. An organic electric element comprising a first electrode, a second electrode, and an organic material layer disposed between the first electrode and the second electrode, wherein the organic material layer comprises a compound of claim 1.

6. The organic electric element of claim 5, wherein the compound is comprised in a light emitting layer of the organic material layer.

7. The organic electric element of claim 6, wherein the compound is used as a phosphorescence red host material of the light emitting layer.

8. The organic electric element of claim 6, wherein the host material of the light emitting layer comprises the compound, and a dopant material of the light emitting layer comprises the compound of Formula 6 below:

[Formula 6]

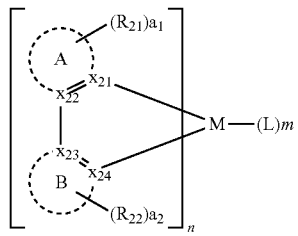

wherein,

A ring and B ring are each independently selected from the group consisting of a $C_4$-$C_{20}$ cycloalkyl group, a $C_2$-$C_{20}$ heterocyclo alkyl group, a $C_6$-$C_{60}$ aryl group, a fluorenyl group, a $C_2$-$C_{60}$ heteroarylene group selected from a group consisting of O, N, S, Si and P, and a fused ring group of $C_3$-$C_{60}$ aliphatic ring and a $C_6$-$C_{60}$ aromatic ring, $X_{21}$ to $X_{24}$ are each independently carbon or nitrogen, $R_{21}$ and $R_{22}$ are each independently selected from the group consisting of deuterium, a halogen, a hydroxyl group, a cyano group, a nitro group, an amino group, an amidino group, a hydrazine group, a hydrazone group, a carboxyl group or a carboxylic acid salt, a phosphoric acid or phosphoric acid salt, —C(=O)$Q_1$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_2$-$C_{60}$ heterocycloalkyl group, a substituted or unsubstituted $C_3$-$C_{60}$ cycloalkenyl group, a substituted or unsubstituted $C_2$-$C_{60}$ heterocycloalkenyl group, a substituted or unsubstituted $C_3$-$C_{60}$ cycloalkenyl group, a substituted or unsubstituted $C_2$-$C_{60}$ heterocycloalkenyl group, $C_6$-$C_{60}$ aryl group, a substituted or unsubstituted $C_6$-$C_{60}$ aryloxy group, a substituted or unsubstituted $C_6$-$C_{60}$ arylthio group, and a substituted or unsubstituted $C_2$-$C_{60}$ heteroaryl group, wherein $Q_1$ is selected from the group consisting of a $C_1$-$C_{10}$ alkyl group, a $C_6$-$C_{10}$ aryl group and a $C_6$-$C_{60}$ aryloxy group, $a_1$ and $a_2$ are each independently an integer of 0 to 8, M is a transition metal having an atomic weight of 40 or more, L is selected from the group consisting of a monodentate organic ligand, bidentate organic ligand, tridentate organic ligand and tetradentate organic ligand, m is an integer of 0 to 4, and, n is an integer of 1 to 3.

9. The organic electric element of claim 8, wherein, in Formula 6, M is selected from the group consisting of Iridium (Ir), Platinum (Pt), Osmium (Os) and Ruthenium (Ru).

10. The organic electric element of claim 8, wherein, in Formula 6, at least one of $X_{21}$ to $X_{24}$ is nitrogen.

11. The organic electric element of claim 8, wherein, in Formula 6, A ring and B ring are each independently selected from the group consisting of cyclopentene, cyclohexene, benzene, naphthalene, indene, fluorene, pyrrol, imidazole, pyrazole, pyridine, pyrazine, pyrimidine, pyridazine, indole, quinoline, isoquinoline, benzimidazole, furan, benzofuran, thiophene, benzothiophene, thiazole, isothiazole, oxazole, isoxazole, benzothiazole and benzoxazole.

12. The organic electric element of claim 8, wherein, in Formula 6, $R_{21}$ and $R_{22}$ are each independently selected from the group consisting of deuterium, —F, —Cl, a cyano group, a nitro group, —C(=O)$Q_1$, a methyl group, a ethyl group, a tert-butyl group, a methoxy group, a tert-butoxy group and a phenyl group, wherein the methyl group, ethyl group or tert-butyl group is optionally substituted with one or more substituent selected from the group consisting of deuterium, —F, —Cl, a cyano group and a nitro group, wherein the phenyl group is optionally substituted with one or more substituent selected from the group consisting of deuterium, —F, —Cl, a cyano group, a nitro group, —C(=O)$Q_1$, a methyl group, a tert-butyl group, a methoxy group and a tert-butoxy group, and, wherein $Q_1$ is a methyl group or a phenyl group.

13. The organic electric element of claim 8, wherein, in Formula 6, L is represented by one of the following formulas:

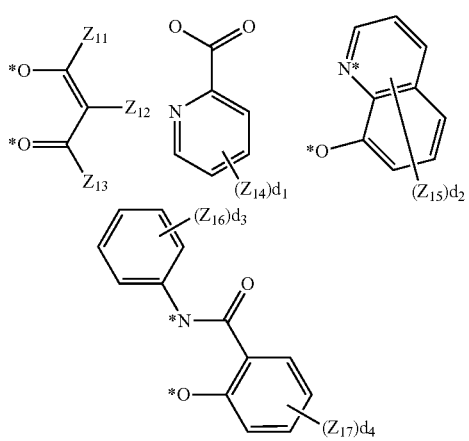

wherein, $Z_{11}$ to $Z_{17}$ are each independently selected from the group consisting of hydrogen, deuterium, halogen, a hydroxyl group, a cyano group, a nitro group, a $C_1$-$C_{60}$ alkyl group, a $C_1$-$C_{60}$ alkoxy group, a $C_6$-$C_{60}$ aryl group and a $C_2$-$C_{60}$ heteroaryl group, wherein the alkyl group or alkoxy group is optionally substituted with one or more substituent selected from the group consisting of deuterium, halogen, a hydroxy group, a cyano group and a nitro group, wherein the aryl group or heteroaryl group is optionally substituted by one or more substituent selected from the group consisting of deuterium, halogen, a hydroxy group, a cyano group, a nitro group, a $C_1$-$C_{60}$ alkyl group and a $C_1$-$C_{60}$ alkoxy group, and, $d_1$ to $d_4$ are each independently an integer of 1 to 4.

14. The organic electric element of claim 8, wherein Formula 6 is represented by one of the following formulas:

[Formula 6-1]

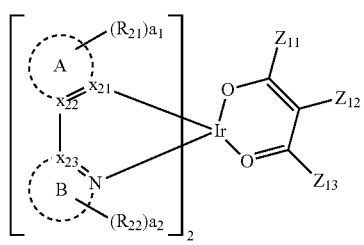

[Formula 6-2]

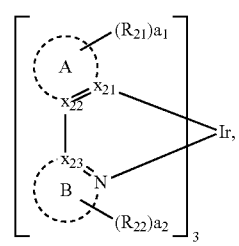

wherein,

A ring and B ring are each-independently selected from the group consisting of cyclopentene, benzene, naphthalene, fluorene, pyridine, pyridazine, quinoline, isoquinoline, benzofurane, benzothiophene, thiazole, isothiazole, and benzoxazole, $R_{21}$ and $R_{22}$ are each-independently selected from the group consisting of deuterium, —F, —Cl, a cyano group, a nitro group, —C(=O)$Q_1$, a methyl group, a ethyl group, a tert-butyl group, a methoxy group, a tert-butoxy group and a phenyl group, $a_1$ and $a_2$ are each independently an integer of 0 to 2, $Z_{11}$ to $Z_{13}$ are each independently selected from the group consisting of hydrogen, deuterium, a methyl group, an ethyl group and a tert-butyl group, wherein the methyl group, ethyl group or tert-butyl group is optionally substituted by one or more substituent selected from the group consisting of deuterium, —F, —Cl, a cyano group and a nitro group, wherein the phenyl group is optionally substituted with one or more substituent selected from the group consisting of deuterium, —F, —Cl, a cyano group, a nitro group, —C(=O)$Q_1$, a methyl group, a tert-butyl group, a methoxy group and a tert-butoxy group, and, wherein $Q_1$ is a methyl group or a phenyl group.

15. The organic electric element of claim 8, wherein the compound represented by Formula 6 is any one of the following compounds:

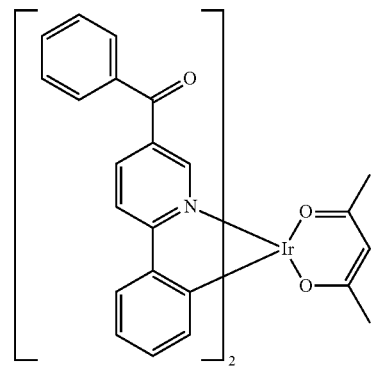

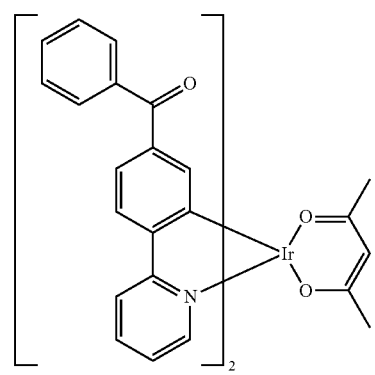

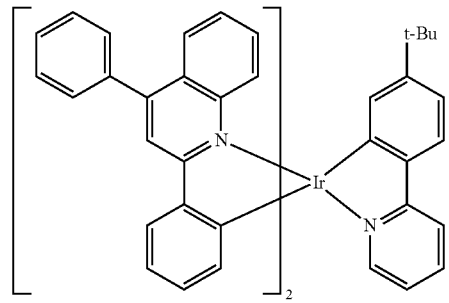

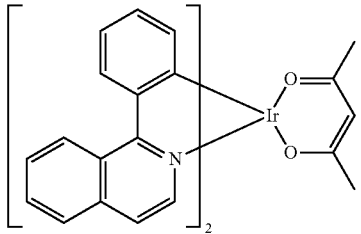
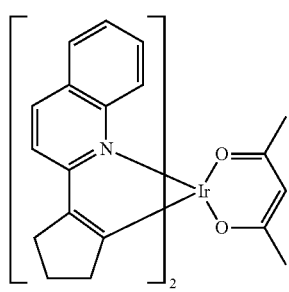
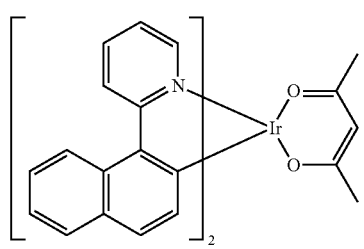
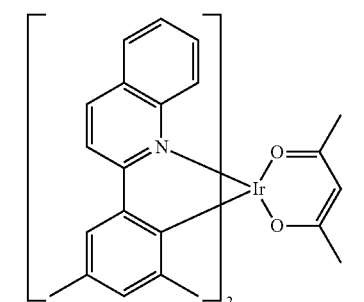
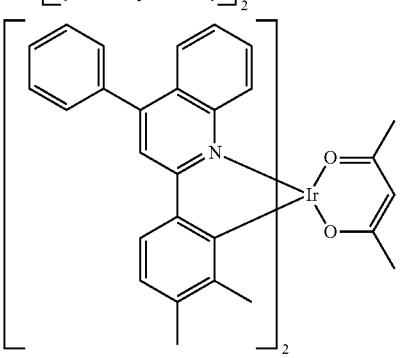
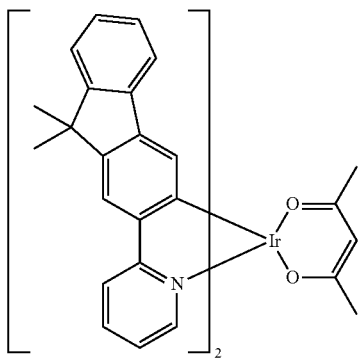
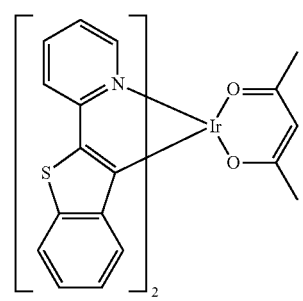
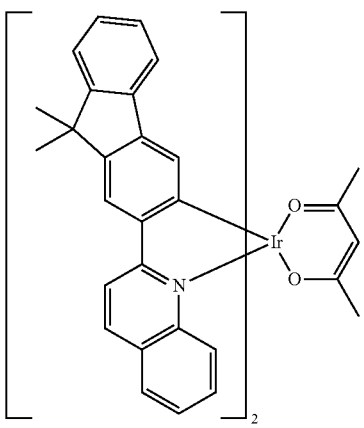
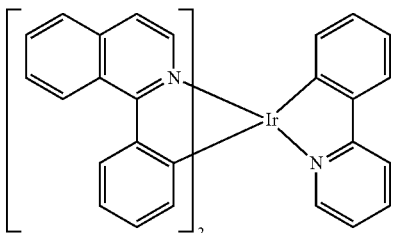
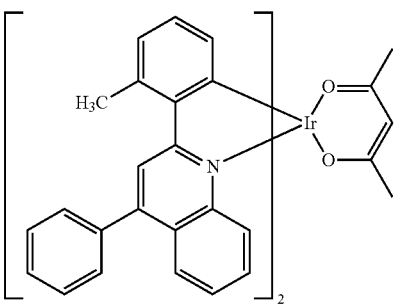

93
-continued
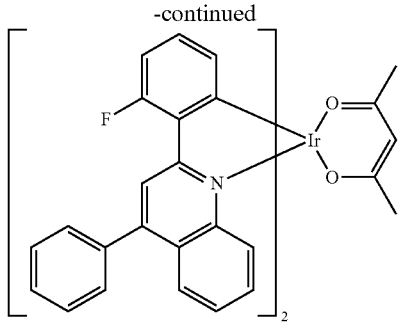
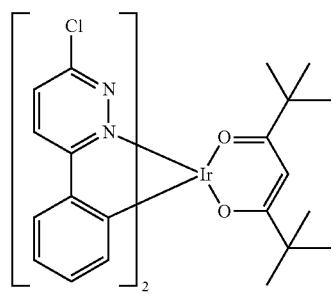
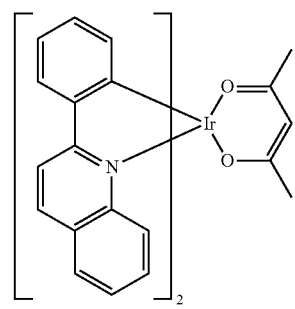
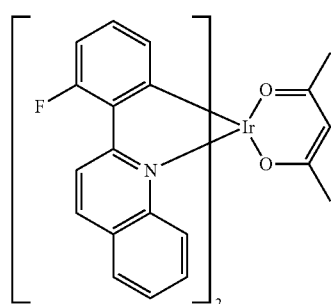
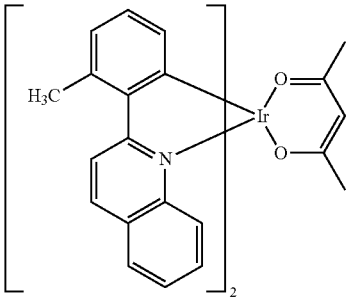
94
-continued
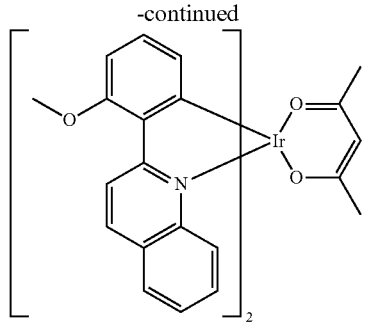
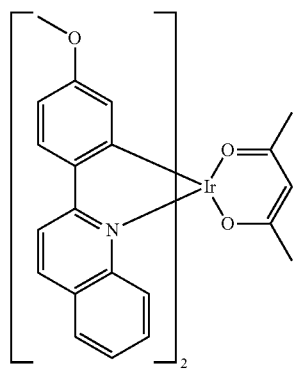
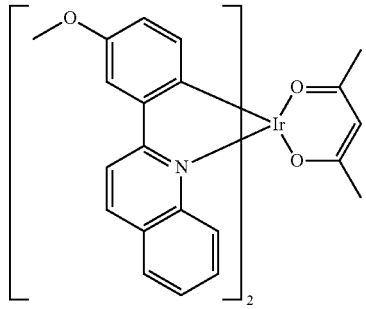
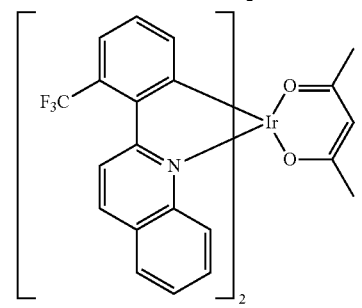
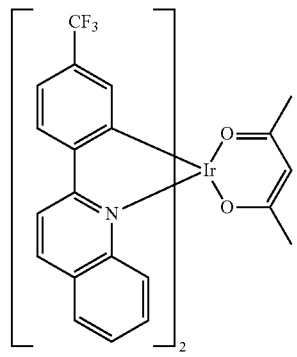

-continued

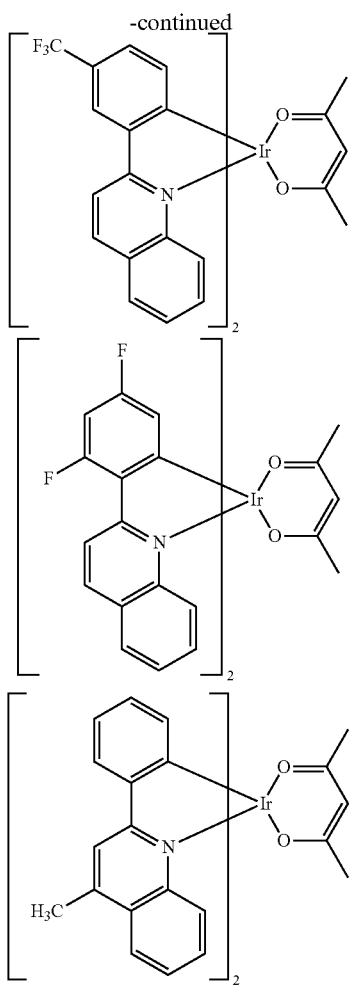

-continued

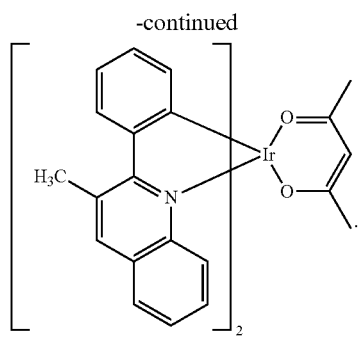

16. The organic electric element of claim 5, wherein the organic electric element further including at least one layer to improve luminous efficiency formed on at least one of the sides of the first and second electrodes, opposite to the organic material layer.

17. The organic electric element of claim 5, wherein the organic material layer is formed by one of the processes consisting of spin coating, nozzle printing, inkjet printing, slot coating, dip coating and roll-to-roll.

18. An electronic device comprising: a display device comprising the organic electric element of claim 5, and a control unit for driving the display device.

19. The electronic device of claim 18, wherein the organic electric element comprises at least one of an organic light emitting diode, an organic solar cell, an organic photo conductor, an organic transistor, and an element for monochromatic or white illumination.

* * * * *